(12) United States Patent
Whitelock et al.

(10) Patent No.: US 10,745,406 B2
(45) Date of Patent: *Aug. 18, 2020

(54) DIHYDROETORPHINES AND THEIR PREPARATION

(71) Applicant: EURO-CELTIQUE S.A., Luxembourg (LU)

(72) Inventors: Steve Whitelock, Cambridge (GB); Deborah Phyllis Harding, Cambridge (GB); Carl David Turner, Manchester (GB)

(73) Assignee: EURO-CELTIQUE S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,970

(22) Filed: Oct. 28, 2016

(65) Prior Publication Data

US 2017/0267687 A1 Sep. 21, 2017

Related U.S. Application Data

(60) Continuation of application No. 14/925,406, filed on Oct. 28, 2015, now Pat. No. 9,481,681, which is a division of application No. 14/473,751, filed on Aug. 18, 2014, now Pat. No. 9,206,190, which is a continuation of application No. 13/133,472, filed as application No. PCT/GB2009/051655 on Dec. 4, 2009, now abandoned.

(30) Foreign Application Priority Data

Dec. 8, 2008 (GB) .................................... 0822342.2
Nov. 26, 2009 (GB) .................................... 0920699.6

(51) Int. Cl.
*A61K 31/485* (2006.01)
*C07D 489/12* (2006.01)
*C07D 489/02* (2006.01)
*A61K 9/70* (2006.01)

(52) U.S. Cl.
CPC .......... *C07D 489/12* (2013.01); *A61K 9/7023* (2013.01); *A61K 31/485* (2013.01); *C07D 489/02* (2013.01)

(58) Field of Classification Search
CPC ............................ C07D 489/12; A61K 31/485
USPC .............................................. 546/39; 514/279
See application file for complete search history.

(56) References Cited

U.S. PATENT DOCUMENTS

| | | |
|---|---|---|
| 4,891,377 A | 1/1990 | Shipman, Jr. et al. |
| 5,271,940 A | 12/1993 | Cleary et al. |
| 5,624,932 A | 4/1997 | Qin et al. |
| 5,849,915 A | 12/1998 | Kim et al. |
| 5,876,746 A | 3/1999 | Jona et al. |
| 6,312,716 B1 | 11/2001 | Midha et al. |
| 6,372,252 B1 | 4/2002 | Blume et al. |
| 6,743,441 B2 | 6/2004 | Sanders et al. |
| 6,770,295 B1 | 8/2004 | Kreilgård et al. |
| D576,282 S | 9/2008 | Yanaki |
| 7,718,188 B2 | 5/2010 | Ito et al. |
| D625,017 S | 10/2010 | Iwahashi et al. |
| 8,071,125 B2 | 12/2011 | Wang et al. |
| 9,206,190 B2 | 12/2015 | Whitelock et al. |
| 9,481,681 B2 | 11/2016 | Whitelock et al. |
| 2002/0010127 A1 | 1/2002 | Oshlack et al. |
| 2003/0064099 A1 | 4/2003 | Oshlack et al. |
| 2003/0068392 A1 | 4/2003 | Sackler |
| 2003/0148941 A1 | 8/2003 | Crain et al. |
| 2003/0191147 A1 | 10/2003 | Sherman et al. |
| 2004/0024005 A1 | 2/2004 | Whistler et al. |
| 2004/0033255 A1 | 2/2004 | Baker et al. |
| 2004/0208917 A1 | 10/2004 | Fischer et al. |
| 2004/0242616 A1 | 12/2004 | Jackson et al. |
| 2005/0002997 A1 | 1/2005 | Howard et al. |
| 2005/0101622 A1 | 5/2005 | Crain et al. |

(Continued)

FOREIGN PATENT DOCUMENTS

| | | |
|---|---|---|
| CA | 2 670 290 C | 5/2016 |
| CN | 1676130 | 10/2005 |

(Continued)

OTHER PUBLICATIONS

Derrick, I., et al., "Perchloric acid induced epimerisation of the thevinones: an improved synthesis of 7β-dihydrothevinones," *Tetrahedron Letters* 41(39):7571-7576, Elsevier Science Ltd., England (2000).

(Continued)

*Primary Examiner* — Charanjit Aulakh
(74) *Attorney, Agent, or Firm* — Sterne, Kessler, Goldstein & Fox P.L.L.C.

(57) ABSTRACT

The present invention provides a process for the preparation of a compound of formula (VI), or a salt or derivative thereof,

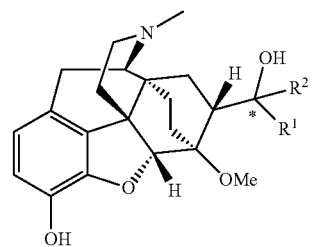

(VI)

wherein $R^1$ and $R^2$ are independently $C_{1-8}$ alkyl and * represents a stereocentre.

19 Claims, 18 Drawing Sheets

(56) References Cited

U.S. PATENT DOCUMENTS

| | | | |
|---|---|---|---|
| 2005/0113365 | A1 | 5/2005 | Lundeen |
| 2006/0039960 | A1 | 2/2006 | Cordes et al. |
| 2006/0111381 | A1 | 5/2006 | Jackson et al. |
| 2006/0111382 | A1 | 5/2006 | Shafer et al. |
| 2006/0177381 | A1 | 8/2006 | Brooks-Korn |
| 2007/0037891 | A1 | 2/2007 | Esfand et al. |
| 2007/0128263 | A1 | 6/2007 | Gargiulo et al. |
| 2008/0039775 | A1 | 2/2008 | Ameri et al. |
| 2010/0150993 | A1 | 6/2010 | Theobald et al. |
| 2011/0027345 | A1 | 2/2011 | Wang et al. |
| 2012/0082714 | A1 | 4/2012 | Bracht et al. |
| 2016/0115174 | A1 | 4/2016 | Whitelock et al. |

FOREIGN PATENT DOCUMENTS

| | | |
|---|---|---|
| CN | 1957918 | 5/2007 |
| EP | 0 418 591 A2 | 3/1991 |
| EP | 0 680 754 B1 | 9/1998 |
| EP | 1 174 137 B1 | 10/2006 |
| EP | 1 439 179 B1 | 3/2008 |
| EP | 2 286 802 A1 | 2/2011 |
| EP | 2 286 814 A1 | 2/2011 |
| EP | 2 298 277 A1 | 3/2011 |
| GB | 925723 | 5/1963 |
| GB | 937214 | 9/1963 |
| JP | 59-184182 | 10/1984 |
| JP | 62-153214 | 7/1987 |
| JP | 62-281815 | 12/1987 |
| JP | 63-201119 | 8/1988 |
| JP | 3-163083 | 7/1991 |
| JP | 8-504189 | 5/1996 |
| JP | 10-231248 | 9/1998 |
| WO | WO 94/06426 A1 | 3/1994 |
| WO | WO 97/14438 | 4/1997 |
| WO | WO 00/01377 | 1/2000 |
| WO | WO 00/51592 A1 | 9/2000 |
| WO | WO 02/05647 A1 | 1/2002 |
| WO | WO 03/070191 A1 | 8/2003 |
| WO | WO 2004/017941 A2 | 3/2004 |
| WO | WO 2004/064839 A1 | 8/2004 |
| WO | WO 2006/110642 A2 | 10/2006 |
| WO | WO 2007/011125 A1 | 1/2007 |
| WO | WO 2007/022535 A2 | 2/2007 |
| WO | WO 2007/052308 A2 | 5/2007 |
| WO | WO 2007/059445 A2 | 5/2007 |
| WO | WO 2008/061625 A2 | 5/2008 |
| WO | WO 2008/083149 A1 | 7/2008 |
| WO | 2008/109156 A2 | 9/2008 |
| WO | WO 2009/088142 A1 | 7/2009 |
| WO | WO 2010/067101 A1 | 6/2010 |

OTHER PUBLICATIONS

Office action dated Feb. 2, 2016, in U.S. Appl. No. 14/925,406, Whitelock, S., et al., filed Oct. 28, 2015.
Notice of Allowance dated Jun. 21, 2016, in U.S. Appl. No. 14/925,406, Whitelock, S., et al., filed Oct. 28, 2015.
Bentley, K.W., et at, "Novel analgesics and molecular rearrangements in the morphine-thebaine group. III. Alcohols of the 6,14-endo-ethenotetrahydrooripavine series and derived analogs of N-allylnormorphine and —norcodeine," *J Am. Chem. Soc.* 89(13):3281-3292, American Chemical Society, United States (1967).
Bentley, K.W., et al., "Novel analgesics and molecular rearrangements in the morphine-thebaine group. IV. Acid-catalyzed rearrangements of alcohols of the 6,14-endo-ethenotetrahydrothebaine series,"*J Am. Chem. Soc.* 89(13):3293-3303, American Chemical Society, United States (1967).
Casy, A.F. and Parfitt, R.T., "Diels-Alder Adducts of Thebaine," in *Opioid Analgesics: Chemistry and Receptors*, pp. 69-73, Plenum Press, United States (1986).
Chuanjin, C., et al., "To Improve the Synthesis of Dihydroetorphine," *Acta Academiae Medicinae Shanghai* 19(3):223-224, Shanghai Medical University, China (1992).

English language translation of Chuanjin, C., et al., "To Improve the Synthesis of Dihydroetorphine," *Acta Academiae Medicinae Shanghai* 19(3):223-224, Shanghai Medical University, China (1992).
Hutchins, C.W. And Rappaport, H., "Analgesics of the Orvinol Type. 19-Deoxy and 6,20-Epoxy Derivates," *J. Med. Chem*, 27:521-527, American Chemical Society, United States (1984).
Li, Y-g. and XU, C-x., "Amelioration of Demethylation to Synthetic Etorfy and Hydroetorfy,"*J. Guangxi Univ. (Nat. Sci. Ed)* 29(3):265-268, Guangxi University, China (2004).
Liu, H., et al., "Synthesis, Crystal Structural and Pharmacological Study of N-Cyclopropylmethyl-7α-[(R)-1-hydroxyl-1-methyl-3-(thien-2-yl)propyl]-6,14-endoethanotetrahydronooripavine,"*Acta Chim. Slov*, 52:80-85, Slovenian Chemical Society, Slovenia (2005).
Lewis, J., "Ring C-bridged derivatives of thebaine and oripavine," *Adv. Biochem. Psychopharmacol.* 8(0):123-36, Raven Press, United States (1974).
Ma, X., et al., "Synthesis of the Highly Effective Analgesic Etorphine," *Fine Chemical Industry* 13(1):12-15, Dalian Institute of Light Industry, China (1996).
Ohmori, S., et al., "A protective effect against undesirable increase of dihydroetorphine permeation through damaged skin by using pressure-sensitive adhesive tape with an ethylene-vinyl acetate co-polymer membrane," *Biol. Pharm. Bull.* 24(1):78-83, Pharmaceutical Society of Japan, Japan (2001).
Qin, B-Y., "Advances in Dihydroetorphine: From Analgesia to Detoxification," *Chin. Bull. Drug. Depend.* 5(4):1-5, China Academic Journal Electronic Publishing House, China (1991).
English language translation of Qin, B-Y., "Advances in Dihydroetorphine: From Analgesia to Detoxification," *Chin. Bull. Drug. Depend.* 5(4):1-5, China Academic Journal Electronic Publishing House, China (1991).
Wang, N-S., et al,, "Dihydroetorphine in Conditioned Place Preference," *Chin. Bull. Drug Depend*. 2(4):271-273, China Academic Journal Electronic Publishing House, China (1993).
English language translation of Wang, N-S., et al., "Dihydroetorphine in Conditioned Place Preference," *Chin. Bull. Drug Depend*. 2(4):271-273, China Academic Journal Electronic Publishing House, China (1993).
Xifa, S. and Li, C., "An Adjuvant Response of Dihydroetorphine in General Anesthesia and Effect on Respiration and Circulation," *Chin. Pharmacist* 5(8):490-491, China Academic Journal Electronic Publishing House, China (2002).
English language translation of Xifa, S. and Li, C., "An Adjuvant Response of Dihydroetorphine in General Anesthesia and Effect on Respiration and Circulation," *Chin. Pharmacist* 5(8):490-491, China Academic Journal Electronic Publishing House, China (2002).
Miao, Z.-C., et al., "$^1$H and $^{13}$C NMR and Stereochemistry of the Analgesic Dihydroetophine," *Chin. J. Org. Chem*. 9(4):347-352, Chinese Chemical Society, China (1989).
English language translation of Miao, Z.-C., et al., "$^1$H and $^{13}$C NMR and Stereochemistry of the Analgesic Dihydroetophine," *Chin. J. Org. Chem*. 9(4):347-352, Chinese Chemical Society, China (1989).
Xu, J.-P., et al., "Effect of dihydroetorphine, ohmefentanyl and etonitazene on immune function in mice," *Chin. J. Pharmacol. Toxicol*. 7(4):290-293, China Academic Journal Electronic Publishing House, China (1993).
English language translation of Xu, J.-P., et at, "Effect of dihydroetorphine, ohmefentanyl and etonitazene on immune function in mice," *Chin. J. Pharmacol. Toxicol.* 7(4):290-293, China Academic Journal Electronic Publishing House (1993).
Miao, H., et al., "The Analgesic Effect of Combined Administration of Dihydroetorphine and Tramadol Mice," *Zhongguo Yaolixue Yu Dulixue Zazhi* 7(4):285, China Academie Journal Electronic Publishing House, China (1993).
English language translation of Miao, H., et al., "The Analgesic Effect of Combined Administration of Dihydroetorphine and Tramadol Mice," *Zhongguo Yaolixue Yu Dulixue Zazhi* 7(4):285, China Academic Journal Electronic Publishing House, China (1993).
English language abstract of JP 62-153214, espacenet database, Worldwide, published Jul. 18, 1987.
English language abstract of JP 62-281815, espacenet database, Worldwide, published Dec. 7, 1987.

(56) References Cited

OTHER PUBLICATIONS

English language abstract of JP 63-201119, espacenet database, Worldwide, published Aug. 19, 1988.
English language abstract of JP 10-231248, espacenet database, Worldwide, published Sep. 2, 1998.
International Search Report dated Apr. 28, 2010 for International application No. PCT/GB2009/051655 by the European Patent Office, Rijswijk.
International Preliminary Report on Patentability and the Written Opinion dated Jun. 14, 2011 for International application No. PCT/G132009/051655 by the International Bureau of WIPO, Geneva.
Bentley, K.W., et al., "Novel Analgesics and Molecular Rearrangements in the Morphine-Thebaine Group. II. Alcohols Derived from 6,14-endo-Etheno- and 6,14-endo-Ethanotetrahydrothebaine," *Journal of the American Chemical Society* 89(13): 3273-3280, American Chemical Society, United States (1967).
Bentley, K.W., et al., "Novel Analgesics and Molecular Rearrangements in the Morphine-Thebaine Group. I. Ketones Derived from 6,14-endo-Ethenotetrahydrothebaine," *J. Am. Chem. Soc.* 89(13):3267-3273, American Chemical Society, United States (1967).
Coop, A., et al., "Methylation of Enolates of Thevione and some Analogues," *Tetrahedron* 51(35): 9681-9698, Elsevier Science Ltd, Great Britain (1995).
Marton, J., et al., "Herstellung von 6,14-Ethenomorphinan-Derivaten," *Monatschefte für Chemie* 125: 1229-1239, Springer-Verlag, Austria (1994).
Park, H., et al., "A highly selective κ-opioid receptor agonist with low addictive potential and dependence liability," *Bioorganic & Medicinal Chemistry Letters* 16: 3609-3613, Elsevier Ltd., Great Britain (2006).
Aceto, M.D., et al., "Dihydroetorphine: physical dependence and stereotype 2 after continuous infusion in the rat," *European Journal of Pharmacology* 387:31-37, Elsevier Science B.V., Netherlands (2000).
Aceto., M., et al., "Etorphines: μ-opiod receptor-selective antinociception and low physical dependence capacity," *European Journal of Pharmacology* 338: 215-223, Elsevier Science B.V., Netherlands (1997).
Beardsley P., and Harris, L.S.., "Evaluation of the discriminative stimulus and reinforcing effects of dihydroetorphine," *Drug and Alcohol Dependence* 48:77-84, Elsevier Science Ireland Ltd., Ireland (1997).
Chen, X.-P., et al., "Transdermal Permeation of Dihydro Etorphine Hydrochloride-Influence pH, Concentration and Surfactants on in vitro Permeation," *Journal of Chinese Pharmaceutical Sciences* 4(4):187-192, Editorial Office of Journal of Chinese Pharmaceutical Sciences, Beijing, China (1995).
Bian, C.F., et al., "Relationship between dihydroetorphine and cholinergic system in the inhibition of respiration and heart rate," *Progress in opiod research proceedings of the 1986 International Narcotics Research Conference*, 516-519, U.S. Dept. Of Health and Human Services, United States (1986).
Biyashev, D., et al., "Biochemical characterisation of newly developed β-etorphine and β-dihydroetorphine derivatives," *European Journal of Pharmacology* 442:23-27 Elsevier Science B.V., Netherlands (2002).
Cao, Y.X., et al., "A survey of 185 dihydroetorphine hydrochloride abusers," *Chin. Bull. Drug Depend.* 4(1):21-24, Gai Suo, Beijing, China (1995).
Chen, J., et al., "Application and comparison of three methods in evaluating the potency of psychological dependence," *Chinese Pharmacological Bulletin* 12(3):235-238, China Academic Journal Electronic Publishing House, China (1996).
Chen, X., et al., "Studies on transdermal delivery system of dihydroetorphine hydrochloride," *Acta. Pharm. Sin.* 31(10):770-774, China Academic Journal Electronic Publishing House, China (1996).
English language translation of Chen, X., et al., "Studies on transdermal delivery system of dihydroetorphine hydrochloride," *Acta. Pharm. Sin.* 31(10):770-774, China Academic Journal Electronic Publishing House, China (1996), 7 pages.
Choe, C.H., et al., "Sedative tolerance accompanies tolerance to the analgesic effects of fentanyl in infant rats," *Pediatric Research* 47:727-735, International Pediatric Research Foundation, Inc., United States (2000).
English language translation of Chinese package insert "Dihydroetorphine Hydrochloride Sublingual Tablets," Beijing Sihuan Science and Technology Co. Ltd., accessed at www.sihuan.com.cn, accessed on. Mar. 5, 2009.
Commission on Narcotic Drugs, Report on the forty-second Session 1999, Supplement No. 8, pp. 1-97, Economic and Social Council, United Nations, New York (2000).
English language translation of Li, E., et al., " Influence of dihydroetorphine hydrochloride and tramadol on labor pain and umbilical blood gas," *Chinese Journal of Obstetrics and Gynecology* 30:345-348, Zhonghua Yi Xue Hi, Peking, China (1995), 3 pages.
Crain, S., et al., "Etorphine Elicits Unique Inhibitory-Agonist and Excitatory-Antagonist Actions at Opioid Receptors on Sensory Neurons: New Rationale for Improved Clinical Analgesia and Treatment of Opiate Addiction," *National Institute on Drug Abuse, Research Monograph Series* 147: 234-268, U.S. Department of Health and Human Services, NIH, United States (1995).
Franz, T.J., "Percutaneous absorption on the relevance of in vitro data," *Journal of Investigative Dermatology* 6 (3):190-195, Williams and Wilkins Co., United States (1975).
English translation of GE, Y., et al., "Clinical assessment of physical dependence potential of dihydroetorphine hydrochloride (DHE)," *Acta. Pharm. Sinica.* 29 (4):256260, Shanghai Ke Xue Ji Shu Chu Ban She, Shanghai, China (1994), 6 pages.
Gerak, LR., et al., "Discriminative stimulus and antinociceptive effects of dihydroetorphine in rhesus monkeys," *Psychopharm.* 166:351-359, Springer-Verlag, Germany (2003).
English translation of Chen, J., et al., "Application and comparison three methods in evaluating the potency of psychological dependence," *Chinese Pharmacological Bulletin* 12(3):235-238, China Academic Journal Electronic Publishing House, China (1996), 7 pages.
Greaves, P., "Histopathology of Preclinical Studies," in *Interpretation and Relevance in Drug Safety Evaluation*, 3$^{rd}$ Edition, pp. 126-127, Elsevier Science B.V., Netherlands (2007).
English language translation of Wang, A., et al., "Effect of dihydroetorphine on mice parturition," *Chin. J. Obstet. Gynecol.* 31(5): 299-301 Zhonghua Yi Xue Hi, Peking, China (1996), 5 pages.
Guo, Q., et al., "Effect of vehicle pH, drug concentration and Azone on the snake skin permeation of dihydroetorphine hydrochloride," *Chin. Pharm. J.* 32(6): 349-352, Pharmaceutical Society of Republic of China, Taipei, Taiwan (1997).
English language translation of Guo, Q., et al., "Effect of vehicle pH, drug concentration and Azone on the snake skin permeation of dihydroetorphine hydrochloride," *Chin. Pharm. J.* 32(6):149-352, Pharmaceutical Society of Republic of China, Taipei, Taiwan (1997), 6 pages.
He, J., et al., "Reports of 103 cases drug addiction by dihydroetorphine," *Journal of Comprehensive Clin. Med.* 12(6):299, American Society of Comprehensive Medicine, United States (1996).
English language translation of HE, J., et al., "Reports of 103 cases drug addiction by dihydroetorphine," *Journal of Comprehensive Clin. Med.* 12(6):299, American Society of Comprehensive Medicine, United States (1996), 2 pages.
Higuchi, T., "Rate of Release of Medicaments from Ointment Bases Containing Drugs in Suspension," *Journal of Pharmaceutical Sciences* 50:874-875, American Pharmaceutical Association, United States (1961).
Zheng, J., et al, "Psychological dependence potential of dihydroetorphine hydrochloride," *Chin. Bull. Drug Depend.* 4(2):65-69, Gai Suo, Beijing, China (1995).
Huang, C., et al., "Clinical use of dihydroetorphine (M99) in department of digestive diseases," *Acta. Phys. Sin.* 2:25, Allerton Press, United States (1985).

(56) References Cited

OTHER PUBLICATIONS

English language translation of Huang, C., et al., "Clinical use of dihydroetorphine (M99) in department of digestive diseases," *Acta. Phys. Sin.* 2:25, Allerton Press, United States (1985), 1 page.

Huang, M., et al., "Pharmacodynamics and Pharmacokinetics of Dihydroetorphine Hydrochloride Administered Sublingually in Mice and Rats," *Acta Pharmacologica Sinica* 9(4):308-312, Shanghai Ke Xue Ji Shu Chu Ban She, Shanghai, China (1988).

Huang, M., et al., "Analgesic and other CNS depressive effects of dihydroetorphine," *Acta Pharmacologica Sinica* 3(1):9-13, Shanghai Ke Xue Ji Shu Chu Ban She, Shanghai, China (1982).

English language translation of Huang, M., et al,, "Analgesic and other CNS depressive effects of dihydroetorphine," *Acta Pharmacologica Sinica* 3(1):9-13, Shanghai Ke Xue ii Shu Chu Ban She, Shanghai, China (1982), 7 pages.

Huang, M., et al., "Physical dependence of dihydroetorphine in mice and monkeys," *Acta Pharmacologica Sinica* 3(2):81-84, Shanghai Ke Xue Ji Shu Chu Ban She, Shanghai, China (1982).

English language translation of Huang, M., et al., "Physical dependence of dihydroetorphine in mice and monkeys," *Acta Pharmacologica Sinica* 3(2):81-84, Shanghai Ke Xue Ji Shu Chu Ban She, Shanghai, China (1982), 3 pages.

Chinese package insert "Dihydroetorphine Hydrochloride Injection Instructions," chinapharm.com.cn, accessed at www.chinapharm. com.cn, accessed on Mar. 3, 4.2009, 4 pages.

English language translation of Chinese package insert "Dihydroetorphine Hydrochloride Injection Instructions,"chinapharm. com.cn, accessed at www.chinapharm.com.cn, accessed on Mar. 3, 2009, 6 pages.

Kamei, J., et al, "Antinociceptive effect of dihydroetorphine in diabetic mice," *European Journal of Pharmacology* 275:109-113, Elsevier Science B.V., Netherlands (1995).

Kamei, J., et al,, "Agonist and antagonist properties of dihydroetorphine for μ-opioid receptors in mice," *Neuroscience Letters* 215:87-90, Elsevier Science Ireland Ltd., Ireland (1996).

Katsumata S., et al., "Pharmacological study of dihydroetorphine in cloned μ-, δ-, and κ-opiod receptors," *European Journal of Pharmacology, Molecular Pharmacology Section* 291:367-373, Elsevier Science B.V., Netherlands (1995).

Li, E., et al., "Influence of dihydroetorphine hydrochloride and tramadol on labor pain and umbilical blood gas," *Chinese Journal of Obstetrics and Gynecology* 30:345-348, Zhonghua Yi Xue Hi, Beijing, China (1995).

Li, J., "Recent Progress in the Research Field of Neuropharmacology in China," *Cell. Mol. Neurobiol.* 28:185-204, Springer Science + Business Media, LLC, United States (2008).

Liu, Z.M., et al., "An epidemiological study on DHE abuse," *Chin. Bull. Drug Depend.* 4(4): 223-231, Gai Suo, Beijing, China (1995).

English language translation of Zheng, J., et al., "Psychological dependence potential of dihydroetorphine hydrochloride," *Chin. Bull. Drug Depend.* 4(2):65-69, Gai Suo, Beijing, China (1995), 9 pages.

Luo, Y., et al., "Monitoring of dihydroetorphine hydrochloride in biological fluid," *Acta Pharmacologica Sinica* 29(9):702-706, China Academic Journal Electronic Publishing House, China (1994).

English language translation of Luo, Y., et al., "Monitoring of dihydroetorphine hydrochloride in biological fluid," *Acta Pharmacologica Sinica* 29(9): 702-706, China Academic Journal Electronic Publishing House, China (1994), 7 pages.

Martin, T.J., et al., "Anti-allodynic actions of intravenous opioids in the nerve injured rat: potential utility of heroin and dihydroetorphine against neuropathic pain," *European Journal of Pharmacology* 357:25-32, Elsevier Science B.V., Netherlands (1998).

English language translation of Qian, J., et al, "Preliminary evaluation on the clinical application of dihydroetorphine," *Bulletin of the Academy of Military Medical Sciences* 5:527-529, Jun Shi Xue Ke Xue Yuan Yuan Kan Bian Ji Bu, Beijing, China (1983), 4 pages.

Zang, D., "A Survey on the Utilization of Narcotic Analgesic Drugs in General Hospitals of Qingdao," *Chin. J. Drug Depend.* 8(3):204-205 and 221, Beijing Da Xue, China (1999).

Ming, X., et al., "Tramadol and dihydroetorphine produce synergistic analgesic effect and postpones acute opiate tolerance in rat," *Acta Physiologica Sinica* 57: 696-704, China Academic Journal Electronic Publishing House, China (2005).

"Notice for the Management of Prescription of Stupefacient and Psychotropic Substances, " Chinese Ministry of Health, 3 pages, China (2005).

Nagatomo, N., et al., "Temperature dependence of early and late currents in human cardiac wild-type and long Q-T ΔKPQ Na$^+$channels," *Am. J.Physiol.* 275 (*Heart Circ. Physiol.* 44):H2016-H2024, American Physiological Society, United States (1998).

Niwa, M., et al., "Opioid receptor interaction and adenylyl cyclase inhibition of dihydroetorphine: direct comparison with etorphine," *Life Sciences* 56:395-400, Elsevier Sciences Ltd., England (1995).

Ohmori S., et al., "Dihydroetorphine: a potent analgesic: pharmacology, toxicology, pharmacokinetics, and clinical effects," *CNS Drug Reviews* 8:391-404, Neva Press, United States (2002).

Ohmori S., et al., "Pharmacokinetic and pharmacodynamic evaluations of a potent analgesic, dihydroetorphine, in hairless rat," *Journal of Pharmacology and Experimental Therapeutics* 296:528-536, The American Society for Pharmacology and Experimental Therapeutics, United States (2001).

Ohmori, S., et al., "Quantitative determination of dihydroetorphine in rat plasma and brain by liquid chromatography-tandem mass spectrometry," *Journal of Chromatography B* 740:253-263, Elsevier Science B.V., Netherlands (2000).

Ohmori, S., et al., "Transdermal delivery of the potent analgesic dihydroetorphine: kinetic analysis of skin permeation and analgesic effect in the hairless rat," *J Pharm. Pharmacal.* 52:1437-1449, American Scientific Publishers, United States (2000).

Qian, J., et al., "Preliminary evaluation on the clinical application of dihydroetorphine," *Bulletin of the Academy of Military Medical Sciences* 5:527-529, Jun Shi Xue Ke Xue Yuan Yuan Kan Bian Ji Bu, Beijing, China (1983).

Qin, B.-Y., "Advances In Dihydroetorphine: From Analgesia to Detoxification," *Drug Development Research* 39:131-134, Wiley-Liss, Inc., United States (1996).

English language translation of Ren., B., et al., "Clinical analgesic effect of dihydroetorphine tablet," *New Drugs and Clinical Remedies* 12(5): 299, Zhongguo Xao Xue Hui Shanghai Fen Hui, Shanghai, China (1993).

Ren., B., et at, "Clinical analgesic effect of dihydroetorphine tablet," *New Drugs and Clinical Remedies* 12(S): 299, Zhongguo Xao Xue. Hui Shanghai Fen Hui, Shanghai, China (1993).

"Notice to Strengthen the Management of the use of DHE by the SFDA," SFDA, Chinese Food and Drug Administration, 1 page, China, (1999).

English language translation of "Notice to Strengthen the Management of the use of DHE by the SFDA," SFDA, Chinese Food and Drug Administration, 1 page, China (1999).

Chinese package insert, "Dihydroetorphine Hydrochloride Sublingual Tablets," Beijing Sihuan Science and Technology Co. Ltd., accessed at www.sihuan.com.cn, accessed on Mar. 5, 2009, 5 pages.

Chinese package insert, "Dihydroetorphine Hydrochloride Sublingual Tablets," chinapharm.com.cn, accessed at www.chinapharm.com. cn, accessed on Mar. 5, 2009.

Sun, Q., "Anaesthetic Application of the Strong Analgesic Drug Dihydroetorphine," *Acta. Phys. Sin.* 2:26, Zhongguo Yao Xue Hui, Beijing, China (1982).

English language abstract of Sun, Q., "Anaesthetic Application of the Strong Analgesic Drug Dihydroetorphine," *Acta. Phys. Sin.* 2:26, Zhongguo Yao Xue Hui, Beijing, China (1982).

Tokuyama S., et al "Antinociceptive Effect of Dihydroetorphine Following Various Routes of Administration: a Comparative Study with Morphine," *Biol. Pharm. Bull.* 19:477-479, Pharmaceutical Society of Japan, Japan (1996).

Tokuyama S., et al., "Antinociceptive Effect of Dihydroetorphine and Its Tolerance/Dependence Liability in Mice," *Biol. Pharm. Bull.* 16(8):774-777, Pharmaceutical Society of Japan, Japan (1993).

Tokuyama, S., et al., "A potent mu-opioid receptor agonist, dihydroetorphine, fails to produce the conditioned place preference in mice," *Jpn. J. Pharmacol.* 71:357-360, Japan Pharmacological Society, Japan (1996).

(56) References Cited

OTHER PUBLICATIONS

Tokuyama, S., et al, "Physical dependence produced by dihydroetorphine in mice," *Biol. Pharm. Bull.* 17(8):1056-1059, Pharmaceutical Society of Japan, Japan (1994).

Van Der. Linde, Hi., et al., "The effect of changes in core body temperature on the QT interval in beagle dogs: a previously ignored phenomenon, with a method for correction," *British Journal of Pharmacology* 154:1474-1481, Nature Publishing Group, England (2008).

Wang D.-X., et al., "Experimental therapeutic effects of dihydroetorphine in morphine- dependent rats and monkeys," *Chinese Journal of Pharmacology and Toxicology* 6(1):36-40, Zhongguo Yao Li Xue Hui, Beijing, China (1992).

English language translation of Wang D., et al., "Experimental therapeutic effects of dihydroetorphine in morphine dependent rats and monkeys," *Chinese Journal of Pharmacology and Toxicology* 6(1):36-40, Zhongguo Yao Li Xue Hui, Beijing, China (1992), 10 pages.

Wang, A., et al., "Effect of dihydroetorphine on mice parturition," *Chin. J. Obstet. Gynecol.* 31(5):299-301, Zhonghua Yi Xue Hi, Beijing, China (1996).

Wang, C., et al., "An investigation on the situation of utilization of narcotic medications for cancer pain patients," *Chin. J. Drug Depend.* 8:210-213, Beijing Da Xue, Beijing, China (1999).

English language translation of "Notice for the Management of Prescription of Stupefacient and Psychotropic Substances, " Chinese Ministry of Health, 3 pages, China (2005), 4 pages.

Wang, D.-X., et al., "Dihydroetorphine is a μ-Receptor-selective Ligand," *J. Pharm. Pharmacol.* 47:669-673, Pharmaceutical Society of Great Britain, England (1995).

Wang, W., et at, "Psychological dependence potential of dihydroetorphine in Rhesus monkeys," *Chin. Bull. Drug Depend.* 6(1):8-12, Zhong Guo Yao Wu Yi Lai Xing Zo Zhi Bain Ji Bu, China (1997).

Wang, Z., et al., "Analysis of 9 mortal eases caused by dihydroetorphine hydrochloride abuse," *Chin. Bull. Drug Depend.* 3:176-178, Zhong Guo Yao Wu Yi Lai Xing Zo Zhi Bain Ji Bu, China (1994).

English language translation of Wang, Z., et al., "Analysis of 9 mortal cases caused by dihydroetorphine hydrochloride abuse," *Chin. Bull. Drug Depend.* 3:176-178, Zhong Guo Yao Wu Yi Lai Xing Zo Zhi Bain Ji Bu, China (1994), 3 pages.

Wu, G., et al., "Dihydroetorphine hydrochloride for moderate and severe cancer pain," *China Cancer Journal* 13:64-67, China National Publications Import & Export Corp., Export Dept., Beijing, China (1991).

English language translation of Wu, G., et al., "Dihydroetorphine hydrochloride for moderate and severe cancer pain," *China Cancer Journal* 13:64-67, China National Publications Import & Export Corp., Export Dept., Beijing, China (1991), 8 pages.

Wu, W.-R., et al., "Immunosuppressive effects of dihydroetorphine, a potent narcotic analgesic, in dihydroetorphine-dependent mice," *European Journal of Pharmacology* 366:261-269, Elsevier Science B.V., Netherlands (1999).

Wu, W.-R., et al., "Involvement of μ-opioid receptors and α-adrenoceptors in the immunomodulatory effects of dihydroetorphine," *European Journal of Pharmacology* 353:79-85, Elsevier Science B.V., Netherlands (1998).

English language translation of Chinese package insert "Dihydroetorphine Hydrochloride Sublingual Tablets," chinapharm.com.cn, accessed at www.chinapharm.com.cn, accessed on Mar. 5, 2009, 5 pages.

Xiao, Y.-H., "Clinical observation of dihydroetorphine on cancer patients of terminal phase," *Journal of New Drugs and Clinical Remedies* 3:40-41, Shanghai Shi Yi Yao Guan Li Ju Ke. Ji Qing Bao Yan Jiu Suo, Shanghai, China (1982).

English language translation of Xiao, Y.-H., "Clinical observation of dihydroetorphine on cancer patients of terminal phase," *Journal of New Drugs and Clinical Remedies* 3:40-41, Shanghai Shi Yi Yao Guan Li Ju Ke Ji Qing Bao Yan Jiu Suo, Shanghai, China (1982), 3 pages.

Yin, H., et al., "The effect of Dhe on neurobehavioral teratology in offsprings of mice," *Chin. Bull. Drug Depend.* 50:145-150, Gai Suo, Beijing, China (1996).

English language translation of Yin, H., et al., "The effect of DHE on neurobehavioral teratology in offsprings of mice," *Chin. Bull. Drug Depend.* 5(3):145-150, Gai Suo, Beijing, China (1996), 8 pages.

Yuan, B.-L., et al., "Distribution of [$^3$H]dihydroetorphine in rat brain observed by in vitro quantitative autoradiography," *Chinese Journal of Pharmacology and Toxicology* 9:61-64, Zhongguo Yao Li Xue Hui, Beijing, China (1995).

English language translation of Wang, W., et al., "Psychological dependence potential of dihydroetorphine in Rhesus monkeys," *Chin. Bull. Drug Depend.* 6(1):8-12, Zhong Guo Yao Wu Yi Lai Xing Zo Zhi Bain Ji Bu, China (1997), 8 pages.

Yuan, S., et al., "Metabolism of [$^3$H]dihydroetorphine in mice," *Academy of Military Med Sciences* 11:46-50, Jun Shi Xue Ke Xue Yuan Yuan Kan Bian Ji Bu, China (1987).

English translation of Huang, M., et al., "Pharmacodynamics and Pharmacokinetics of Dihydroetorphine Hydrochloride Administered Sublingually in Mice and Rats," *Acta Pharmacologica Sinica* 9(4):308-312, Shanghai Ke Xue Ji Shu Chu Ban She, Shanghai, China (1988), 8 pages.

Ge, Y., et al., "Clinical assessment of physical dependence potential of dihydroetorphine hydrochloride (DHE)," *Acta. Pharm. Sinica.* 29 (4):256-260, Shanghai Ke Xue Ji Shu Chu Ban She, Shanghai, China (1994).

Pharmacopoeia of the People's. Republic of China vol. II, "New Admissions," p. XX and XXI, "Dihydroetorphine Hydrocholoride," p. 434, and "Dihydroetorphine Hydrochloride Sublingual Tablets," p. 435, Eds. HE Hong mei and CUI Liping, China Medical Science Press, Beijing, China (2010), 8 pages.

Abel, A.M., et al., "Synthesis of potential buprenorphine intermediates by selective microbial *N*- and *O*-demethylation," *Biotechnology Letters* 24(15):1291-1294, Kluwer Academic Publishers, Netherlands (2002).

English Abstract of Japanese Patent Publication. No. JP 59-184182 (FP18), date of publication Oct. 19, 1984.

Grivas, K., et al., "Acid. Catalysed Rearrangements of the Thevinols: The Mechanism of Furanocodide Formation," *Tetrahedron Letters* 40:1795-1798, Elsevier Science Ltd., Netherlands (1999).

Husbands, S.M., et al, "Ring Constrained Analogues of the Orvinols: The Furanomorphides," *Bioorg.& Med Chem. Lett.* 9; 831-834, Elsevier Science Ltd., Netherlands (1999).

Knipmeyer, L.L. and Rapoport, H., "Analgesics of the 6,14-Ethenomorphinan Type. 6-Deoxy-7α-orvinols and 6-Deoxy-8α-orvinols," *J. Med Chem.* 28(4):461-466, American Chemical Society, United States (1985).

Sepsi, A., et al "Investigation of the Azidolysis of Tertiary Alcohols of Thebaine Derivatives with Bridged Ring C," *Arch. Pharm. (Weinheim)* 326:313-317, VCH Verlagsgesellschaft mbH, Germany (1993).

Marton, J. et al, "Studies on the synthesis of β-thevinone derivatives," *Tetrahedron* 54:9143-9152, Elsevier Science, Great Britain (1998).

Office Action dated Feb. 4, 2014, in U.S. Appl. No. 13/133,472, Whitelock, S. et al., having a 35 U.S.C. §371(c) dated Sep. 28, 2011.

Notice of Allowance dated May 30, 2014, in U.S. Appl. No. 13/133,472, Whitelock, S. et al., having a 35 U.S.C. §371(c) dated Sep. 28, 2011.

Huang, M. et al., "Dihydroetorphine, a potent opioid with low dependent potential," *Regulatory Peptides Suppl*, 1:S81-S82 (1994), accessed online at Database EMBASE, Database Accession No. EMB-1994143791, accessed on Aug. 9, 2014, 1 page.

Kamei, J., et al., "Antitussive effect of dihydroetorphine in mice," *Eur. J. Pharmacol.* 260(2-3):257-259, Elsevier Science B.V., Netherlands (1994).

Liu, F., et al., "Determination of dihydroetorphine in biological fluids by gas chromatography-mass spectrometry using selected-ion monitoring," *Journal of Chromatgraphy B* 679(1-2):113-118, Elsevier Science B.V., Netherlands (1996).

Abel, A.M., et al., "The synthesis of buprenorphine intermediates by regioselective microbial *N*- and *O*-demethylation reactions using

(56) References Cited

OTHER PUBLICATIONS

Cunninghamella echinulata NRRL 1384," *Enzyme and Microbial Technology* 33(5):743-748 (2003).
Office action dated May 1, 2015, in U.S. Appl. No. 14/473,751, Whitelock, S., et al., filed Aug. 29, 2014.
Notice of Allowance dated Aug. 6, 2015, in U.S. Appl. No. 14/473,751, Whitelock, S., et al., filed Aug. 29, 2014.
English language abstract of CN 1676130 (cited as document FP29 on accompanying form PTO/SB/08A), Espacenet database, Worldwide, published Oct. 5, 2005.
English language abstract of CN 1957918 (cited as document FP30 on accompanying form PTO/SB/08A), Espacenet database, Worldwide, published May 9, 2007.
Rennison, D., et al., "Formic Acid Catalysed Rearrangement of 5β-Methyldihydrothevinols (=3,6-Dimethoxy-5,17-dimethyl-4,5-epoxy-6,14-ethanomorphinan-7-methanols): Synthesis of New Doubly Bridged Morphinan Derivatives," *Chemistry & Biodiversity* 2(2):215-220, Verlag Helvetica Chimica Acta AG, Zurich, Switzerland (2005).
Chen, Y-J. And Chen, C., "Synthesis of deuterium-labelled etorphine and dihydroetorphine," *Journal of Labelled Compounds and Radiopharmaceuticals* 50(13):1143-1147, John Wiley & Sons Ltd., England (2007).
Kroemer, H. K., et al., "Enantioselectivity in Drug Action and Drug Metabolism: Influence on Dynamics," in *Pharmacodynamics and Drug Development, Perspectives in Clinical Pharmacology*, Chapter 6, pp. 103-114, Eds. Cutler, N. R. et al., John Wiley and Sons Ltd., England (1994).
Nguyen, L.A., et al. "Chiral Drugs: An Overview," *International Journal of Biomedical Science* 2(2)):85-100, Master Publishing Group, United States (2006).
Shi, J. and Zhuang, J., "Pharmacology and Clinical Application of Dihydroetorphine Hydrochloride," *Strait Pharmaceutical Journal* 6(4):37-38, China Academic Journal Electronic Publishing House, China (1994).
Unverified English language translation of Shi, J. and Zhuang, J., "Pharmacology and Clinical Application of Dihydroetorphine Hydrochloride," *Strait Pharmaceutical Journal* 6(4):37-38, China Academic Journal Electronic Publishing House, China (1994).

(R)-19-Pr-DHT (R)-19-Pr-DHT (S)-19-Pr-DHT (S)-DHE (Diastereisomer)    (R)-DHE

# P<0.05, ## P<0.01 when compared to vehicle (ANOVA and Dunnett's t-test).
* P<0.05,  P<0.01 and *P<0.001 when compared to vehicle (Kruskal-Wallis and Dunn's test).

# P<0.05, ## P<0.01 when compared to vehicle (ANOVA and Dunnett's t-test).
 P<0.01 and *P<0.001 when compared to vehicle (Kruskal-Wallis and Dunn's test).

* P<0.05 and P<0.01 and * P<0.001 when compared to vehicle (Kruskal-Wallis and Dunn's test).

DHE R-isomer ED50=0.2532 µg/kg
DHE S-isomer ED50=7.516 µg/kg
Fentanyl ED50=3.111 µg/kg DHE R-isomer ED50=0.4222 µg/kg
DHE S-Isomer ED50=20.95 µg/kg
Fentanyl ED50=9.681 µg/kg

## P < 0.01 when compared to vehicle group data (Kruskal-Wallis and Dunn's test).
* P < 0.05, *** P < 0.001 when compared to pre-dose data (paired 2-tailed Student's t-test).

+ P < 0.05, ++ P < 0.01 and +++ P < 0.001 when compared to pre-dose data (paired 2-tailed Student's t-test).
# P < 0.05, ## P < 0.01 and ### P < 0.001 when compared to vehicle group data (Kruskal-Wallis and Dunn's test).
** P < 0.01 when compared to vehicle group data (ANOVA and Dunnett's test).

a) Left Paw a) Right Paw

+ P < 0.05, ++ P < 0.01 when compared to pre-dose data (paired 2-tailed Student's t-test).

DIHYDROETORPHINES AND THEIR PREPARATION

This invention relates to a new process for making dihydroetorphine, to (S)-dihydroetorphine per se as well as to intermediates prepared during its synthesis.

(R)-Dihydroetorphine (shown below) is a potent analgesic drug.

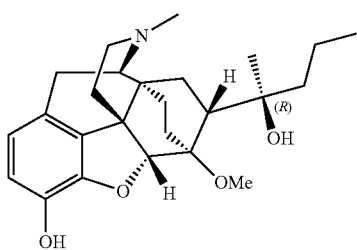

It is mainly used in China in sublingual form at doses ranging from 20 to 180 μg. Compared to other analgesics it is reported to cause strong analgesia and relatively mild side effects. The use of (R)-dihydroetorphine in transdermal patches is also disclosed in JP-10-231248. As far as the applicant is aware, however, no such patch is commercially available.

Dihydroetorphine is a variant of etorphine. (R)-Etorphine is an extremely powerful opioid used for anaesthetising animals, e.g. elephants. It was developed in the 1960s and synthetic routes for its preparation are well known. Example 12 of GB 925,723, for instance, discloses a synthesis of etorphine wherein a Grignard reagent (propyl magnesium iodide) is added to a thebaine derivative as shown below:

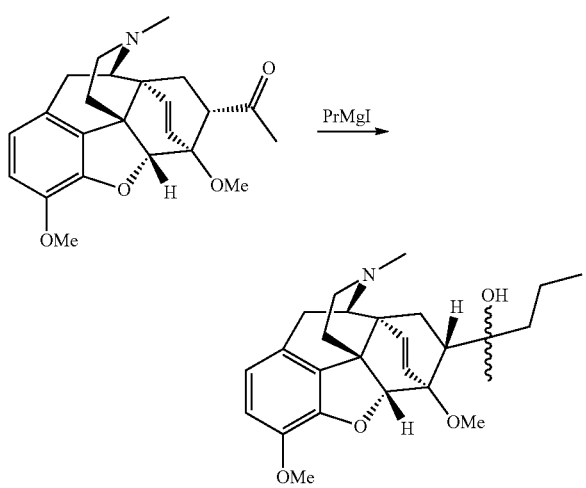

The results given in Example 12 state that the α-isomer is produced upon trituration of the crude reaction product with methanol and that the β-isomer could be crystallised from the methanolic liquors when they were diluted with water and the liquid decanted. The applicant therefore expected that the synthetic route described in GB 925,723 could be applied to dihydroetorphine and that both (R) and (S) diastereomers would result. It was found, however, that this was not the case. Rather the addition of propyl magnesium halide to the dihydro thebaine derivative occurred with unexpectedly high stereoselectivity and only (R) diastereomer was obtained.

As far as the applicants are aware, the (S) isomer of dihydroetorphine has never been prepared. There is therefore a need for an alternative synthetic route that affords (S)-dihydroetorphine and especially for a procedure that yields (S)-dihydroetophine in a high diastereomeric excess. This isomer is required to confirm the stereochemistry of the known stereoisomers.

The applicant has now found a process that satisfies these needs. Moreover applicant has found that the (S) isomer of dihydroetorphine possesses useful pharmacological properties and in particular analgesic effects.

Thus viewed from one aspect the invention relates to a process for the preparation of a compound of formula (VI), or a salt or derivative thereof,

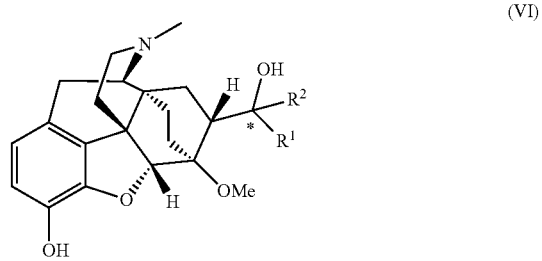

(wherein $R^1$ and $R^2$ are independently $C_{1-8}$ alkyl and * represents a stereocentre, preferably a S stereocentre) comprising hydrolysing a compound of formula (V)

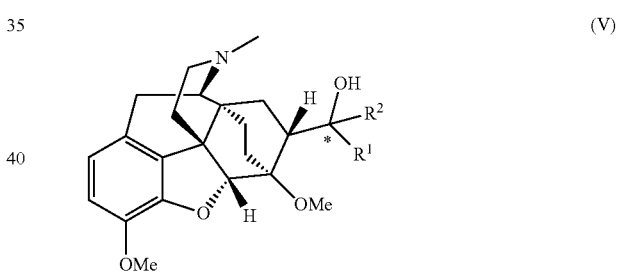

wherein $R^1$, $R^2$ and * are as hereinbefore defined.

In a preferred process of the present invention, the compound of formula (V) is prepared by reacting a compound of formula (IV)

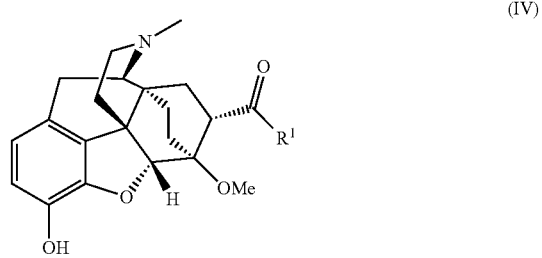

(wherein $R^1$ is as hereinbefore defined);
with a compound of formula $R^2M(X)p$, wherein $R^2$ is $C_{1-8}$ alkyl, M is metal, X is halide and p is 1 or 0).

In a further preferred process of the present invention, the compound of formula (IV) is prepared by reducing a compound of formula (III)

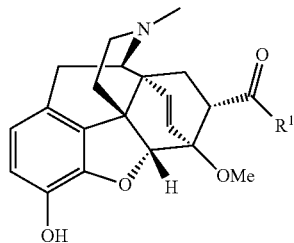
(III)

(wherein R¹ is as hereinbefore defined);

In a yet further preferred process of the present invention, the compound of formula (III) is prepared by reacting a compound of formula (I)

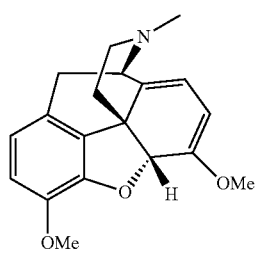
(I)

with a compound of formula (II)

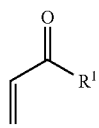
(II)

(wherein R¹ is $C_{1-8}$ alkyl).

Thus viewed from another aspect, the present invention provides a process for the preparation of a compound of formula (VI), or a salt or derivative thereof,

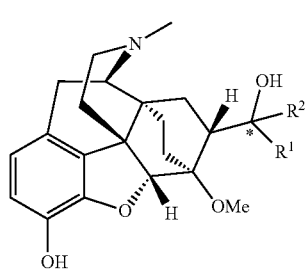
(VI)

(wherein R¹ and R² are independently $C_{1-8}$ alkyl and * represents a stereocentre, preferably a S stereocentre) comprising:

reacting a compound of formula (I)

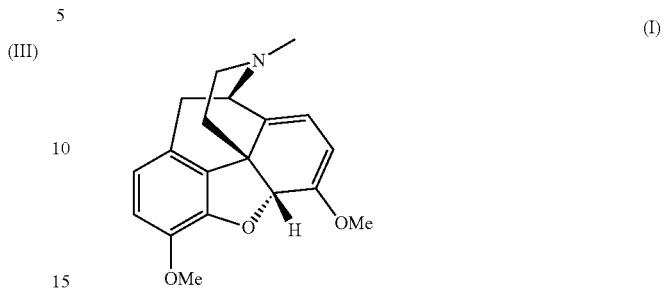
(I)

with a compound of formula (II)

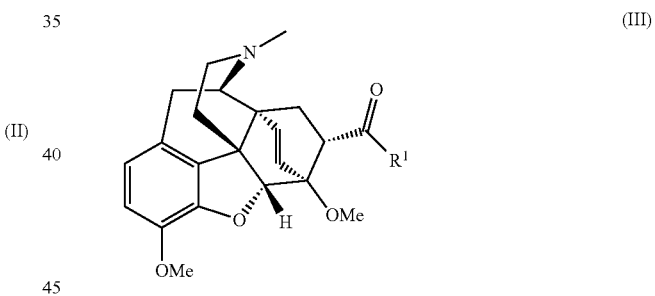
(II)

(wherein R¹ is $C_{1-8}$ alkyl) to give a compound of formula (III)

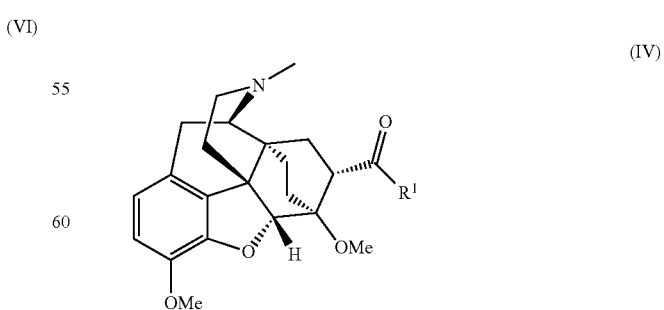
(III)

(wherein R¹ is as hereinbefore defined);

reducing said compound of formula (III) to produce a compound of formula (IV)

(IV)

(wherein R¹ is as hereinbefore defined);

reacting said compound of formula (IV) with a compound of formula R²M(X)$_p$, wherein R² is C$_{1-8}$ alkyl, M is metal, X is halide and p is 1 or 0, to give a compound of formula (V)

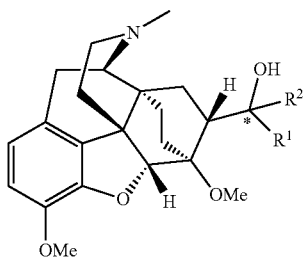

(V)

(wherein R¹, R² and * are as hereinbefore defined);

(iv) hydrolysing said compound of formula (V) to produce a compound of formula (VI).

Viewed from a further aspect the invention relates to a compound of formula (VI), or a salt or derivative thereof,

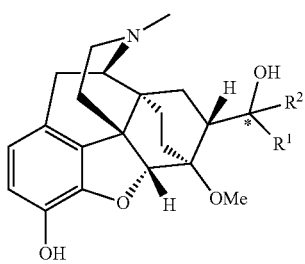

(VI)

wherein R¹ and R² are independently C$_{1-8}$ alkyl and the * represents a (S) stereocentre.

Viewed from a still further aspect the invention relates to compounds that are intermediates in the above-described process, i.e. to compounds of formulae (V), (IV) and (III), or where applicable to salts or derivatives thereof, as shown below:

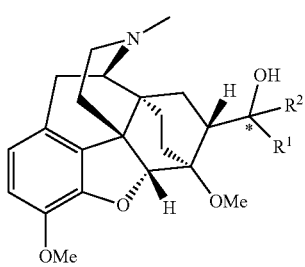

(V)

wherein R¹ and R² are independently C$_{1-8}$ alkyl and the * represents a (S) or (R) stereocentre, preferably a (S) stereocentre.

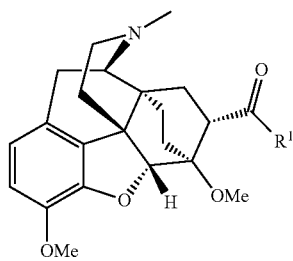

(IV)

wherein R¹ is C$_{1-8}$ alkyl.

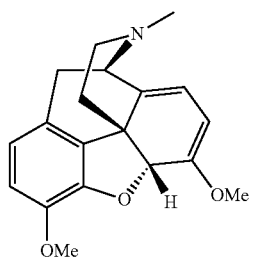

(III)

wherein R¹ is C$_{1-8}$ alkyl.

Viewed from a still further aspect the invention relates to a process for preparing a compound of formula (III) comprising reacting a compound of formula (I)

(I)

with a compound of formula (II)

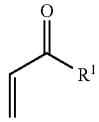

(II)

(wherein R¹ is C$_{1-8}$ alkyl).

Viewed from another aspect the invention relates to compositions, preferably pharmaceutical compositions, comprising a novel compound as hereinbefore described.

Viewed from another aspect the invention relates to compounds as hereinbefore described for use in medicine (e.g. as an analgesic).

Viewed from yet another aspect the invention relates to use of a compound as hereinbefore described for the manufacture of a medicament for the treatment of pain.

As used herein the term "alkyl" is used to refer to a straight chained, cyclic or branched, saturated, aliphatic hydrocarbon. Preferred alkyl groups present in the compounds (II)-(VI) are straight chained alkyl groups. Preferred alkyl groups are of the formula $C_nH_{2n+1}$ wherein n is 1 to 8. Typical alkyl groups include methyl, ethyl, propyl, butyl, pentyl, hexyl, heptyl and octyl. Preferred alkyl groups in the compounds (II)-(VI) are unsubstituted.

The compound of formula (I) is thebaine and is commercially available, e.g. from Tasmanian Alkaloids, Pty. Alternatively the compound of formula (I) can be prepared according to procedures described in the literature.

In a preferred process of the invention $R^1$ in the compound of formula (II) is preferably $C_{2-7}$ alkyl, more preferably $C_{3-5}$ alkyl, especially $C_3$ alkyl (e.g. n-propyl). A particularly preferred compound of formula (II) is hexen-3-one. It is commercially available, e.g. from Sigma-Aldrich.

The compound of formula (I) is reacted with a compound of formula (II) so as to produce a compound of formula (III). The reaction that these compounds undergo is typically referred to as a Diels-Alder reaction. The Diels-Alder reaction may be carried out under conventional conditions known in the art. The reaction of compounds of formulae (I) and (II) may, for instance, be carried out in any conventional solvent. Solvents having boiling points in excess of 60° C. are preferred (e.g. methanol and ethanol). Ethanol is a particularly preferred solvent.

In a typical reaction between compounds of formulae (I) and (II) the compounds are heated to reflux in excess solvent, e.g. for 10-24 hours. The process of the reaction may be monitored using, e.g. TLC and/or $^1$H NMR. In a preferred reaction 1.2-15 molar equivalents, more preferably 1.5-10 molar equivalents or 2-8 molar equivalents of the compound of formula (II) is used relative to the compound of formula (I). In a particularly preferred reaction about 1.2-2 molar equivalents, more preferably 1.3-1.8 molar equivalents, e.g. about 1.5 molar equivalents of the compound of formula (II) is used relative to the compound of formula (I).

The reaction mixture is then cooled and concentrated. The resulting product, a compound of formula (III), may be obtained by a conventional work up procedure and optionally purified. Purification may, for example, by carried out by crystallisation from methanol or isopropyl alcohol. More preferably the compound of formula (III) crystallises directly from the reaction solvent. It may optionally be recrystallised. The yield of the reaction is preferably at least 60%, more preferably at least 65%, e.g. at least 80%. The maximum yield is 100%. The purity of the compound of formula (III) is preferably at least 95%, more preferably at least 97%, still more preferably at least 99%, e.g. 99.5%. The maximum purity is 100%. Purity is preferably determined using HPLC.

In a preferred process of the invention the compound of formula (III) is of formula:

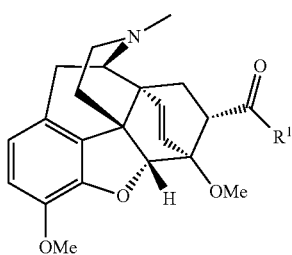

(III)

wherein $R^1$ is as hereinbefore defined, e.g. $R^1$ is $C_{2-7}$ alkyl, more preferably $C_{3-5}$ alkyl, especially $C_3$ alkyl (e.g. n-propyl).

The compound of formula (III) may be reduced by any suitable known reduction reaction but is preferably reduced using an hydrogenation reaction (e.g. using $H_2$ in a Parr vessel or hydrogen transfer). The compound of formula (III) may, for example, be hydrogenated in solvent (e.g. ethanol) with catalyst (e.g. palladium on carbon) under a pressure of hydrogen (e.g. up to 50 psi $H_2$). The volume of the reaction is preferably in the range 5-80 L, more preferably 10-20 L, e.g. about 12 L. The amount of catalyst used is preferably in the range 10-60% wt, more preferably 30-55% wt, e.g. about 50% wt. The reaction may be carried out at a temperature of 30-100° C., preferably at a temperature of 40-60° C., e.g. at 50° C. or 65° C.

At the end of the reaction, any catalyst (e.g. palladium) used therein may be removed by filtration. The product, a compound of formula (IV), may then be isolated by a conventional work up procedure. The compound of formula (IV) is optionally purified. For instance, washing with a $C_{1-8}$ alkane such as heptane removes ethanol. An advantage of the hydrogenation reaction is, however, that the compound of formula (IV) can be used without purification by chromatography and/or crystallisation. The yield of the reaction is preferably at least 50%, more preferably at least 65%, still more preferably 85%, still more preferably at least 90%. The maximum yield is 100%. The compound of formula (IV) is preferably obtained with a purity of at least 95%, more preferably at least 99%, e.g. at least 99.5%. The maximum purity is 100%. Purity is preferably determined using HPLC.

In a preferred process of the invention the compound of formula (IV) is of formula:

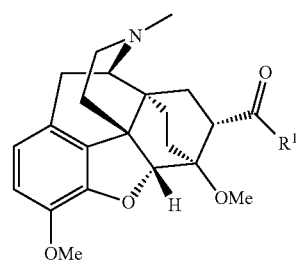

(IV)

wherein $R^1$ is as hereinbefore defined, e.g. $R^1$ is $C_{2-7}$ alkyl, more preferably $C_{3-5}$ alkyl, especially $C_3$ alkyl (e.g. n-propyl)

The compound of formula (IV) is reacted with a compound of formula $R^2M(X)_p$ wherein $R^2$ is $C_{1-8}$ alkyl, M is metal (e.g. an alkali or alkaline earth metal), X is halide and p is 1 or 0, to produce a compound of formula (V). In preferred compounds of formula $R^2M(X)_p$, $R^2$ is $C_{1-3}$ alkyl, more preferably $C_{1-2}$ alkyl, e.g. methyl.

In further preferred compounds of the formula $R^2M(X)_p$ M is magnesium or lithium, preferably magnesium. When M is Mg, p is preferably 1. When M is lithium, p is preferably 0. When present X is preferably Cl, Br or I. Methyl magnesium halide, especially methyl magnesium bromide and methyl magnesium iodide, is a preferred compound of formula $R^2M(X)_p$, especially methyl magnesium bromide.

The reaction of the compound of formula (IV) with a compound of formula $R^2M(X)_p$ is typically referred to as a nucleophilic addition reaction. When M is Mg and X is halide, the reaction is often referred to as a Grignard addition. The addition reaction may be carried out in any conventional solvent. Preferred solvents are non-aqueous (e.g. anhydrous solvents). An example of a preferred solvent is an ether, e.g. MTBE, THF or diethyl ether. MTBE or diethyl ether are preferred. Diethyl ether is a particularly preferred solvent. THF is particularly preferred when a compound of formula $R^2M(X)_p$, wherein M is Mg, X is Cl and p is 2, is used.

The addition reaction is preferably carried out at a temperature in the range 20 to 60° C., more preferably 30 to 45° C., e.g. about 35° C. An excess of the compound of formula $R^2M(X)_p$ is preferably used. In particular 1.2-4 equivalents, more preferably 1.5-3 equivalents of a compound of formula $R^2M(X)_p$ is preferably used relative to the compound of formula (IV).

The compound of formula (V) may be isolated using conventional techniques. It may optionally be triturated, e.g. with methanol. Additionally, or alternatively, the compound of formula (V) may be purified by column chromatography. The compound of formula (V) may also be crystallised. Preferably the compound of formula (V) is crystallised with methanol. The yield of the reaction is preferably at least 20%, more preferably at least 30%, e.g. 20-60%, still more preferably at least 65%. The maximum yield is 100%. The purity of the compound of formula (V) is preferably at least 95%, still more preferably at least 99%, e.g. at least 99.5%. The maximum purity is 100%. Purity is preferably determined using HPLC.

The addition reaction generates a new stereocentre in the compound of formula (V) at carbon 19. The configuration of this stereocentre depends, at least partially, on the nature of $R^1$ and $R^2$. Thus both (R) and (S) stereocentres may be generated. The process of the present invention may therefore provide a racemic mixture of compounds of formula (V). Correspondingly the present invention provides a racemic mixture of compounds of formula (VI), e.g. 19-(R) and (S)-dihydroetorphine.

In preferred processes of the invention, a (S) stereocentre is generated at carbon 19. In particularly preferred processes, a (S) stereocentre is generated at carbon 19 in a diastereomeric excess of at least 85%, more preferably at least 90%, e.g. at least 95% or at least 99%. Thus in a preferred process a compound of formula (V) is provided in the absence of, or substantial absence of, (R)-isomer. Preferably the compound of formula (V) is provided with less than 1% wt, still more preferably less than 0.5% wt of (R)-isomer.

In a particularly preferred process of the invention, $R^1$ is $C_{3-6}$ alkyl (e.g. propyl), $R^2$ is $C_{1-2}$ alkyl (e.g. methyl) and a (S) stereocentre is generated in the addition reaction at carbon 19 in a diastereomeric excess of at least 85%, more preferably at least 90%, e.g. at least 95% or at least 99%.

Thus in a preferred process of the invention the compound of formula (V) is of the formula:

(V)

wherein $R^1$ and $R^2$ are as hereinbefore described, e.g. $R^1$ is $C_{2-7}$ alkyl, more preferably $C_{3-5}$ alkyl, especially $C_3$ alkyl (e.g. n-propyl), $R^2$ is $C_{1-3}$ alkyl, more preferably $C_{1-2}$ alkyl, e.g. methyl and the (*) represents a stereocentre, preferably a S stereocentre.

In a particularly preferred process of the invention the compound of formula (V) is:

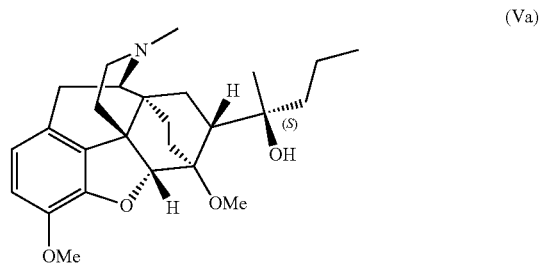

(Va)

As mentioned above, the compound of formula (V) may optionally be crystallised. In a preferred process of the invention, the compound of formula (V) is crystallised. Any conventional solvent may be used for the crystallisation process, e.g. $C_{1-4}$ alcohols, water, acetone, acetonitrile, DCM and MTBE. Methanol, ethanol, water and mixtures thereof are preferred crystallisation solvents, especially ethanol/water and ethanol. In a typical crystallisation process, an amount of the compound of formula (V) obtained from the addition reaction is dissolved in the chosen solvent, preferably a minimum amount thereof, and the solution is allowed to stand, e.g. for 3-4 days. Preferably crystallisation is carried out at −5 to 5° C., e.g. 0-4° C.

The compound of formula (V) is preferably hydrolysed with an alkali metal hydroxide to form a compound of formula (VI). A preferred alkali metal hydroxide is KOH. An excess of alkali metal hydroxide is preferably used in the hydrolysis reaction, e.g. an excess of 10-40 equivalents relative to the compound of formula (V). The reaction may be carried out in any conventional solvent. Diethylene glycol is a preferred solvent.

The hydrolysis reaction is preferably carried out at a temperature in the range 150-220° C., e.g. about 180-200° C. The progress of the reaction may be monitored by conventional techniques, e.g. TLC, but will typically take 10-20 hours, e.g. 12-18 hours. After the reaction is complete, the compound of formula (VI) may be isolated using conventional techniques. The compound of formula (VI) may be triturated. The yield of the reaction is preferably at least 40%, more preferably at least 45%, still more preferably 85%, yet more preferably at least 90%. The maximum yield is 100%. The purity of the compound of formula (VI) is preferably at least 90%, still more preferably at least 95%. The maximum purity is 100%. Purity is preferably determined using HPLC.

The compound of formula (VI) may also be crystalllised. Preferred solvents for use in crystallisation are AcCN and MTBE. More preferably the compound of formula (VI) is crystallised from a $C_{1-4}$ alcohol and/or water, e.g. ethanol and/or ethanol/water.

In a preferred hydrolysis reaction the stereochemistry of each of the stereocentres present in the compound of formula (V) is retained. Preferably the compound of formula (VI), e.g. 19-S-dihydroetorphine, is provided in the absence of or substantial absence of the (R)-isomer. Preferably less than 1% wt, more preferably less than 0.5% wt, still more preferably less than 0.01% wt (R)-isomer is present.

Thus in a preferred process the compound of formula (VI) is:

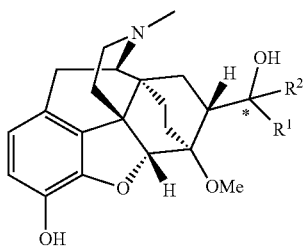

wherein $R^1$ and $R^2$ are as hereinbefore described, e.g. $R^1$ is $C_{2-7}$ alkyl, more preferably $C_{3-5}$ alkyl, especially $C_3$ alkyl (e.g. n-propyl), $R^2$ is $C_{1-3}$ alkyl, more preferably $C_{1-2}$ alkyl, e.g. methyl and the (*) represents a stereocentre, preferably a S stereocentre. Preferably the compound of formula (VI) has a purity of at least 99%, e.g. as determined by HPLC.

In a particularly preferred process the compound of formula (VI) is:

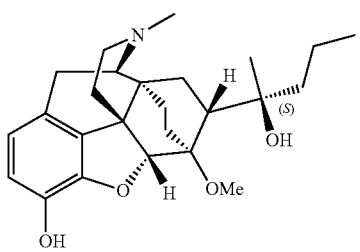

(VIa)

The compounds (V) and (VI) hereinbefore described may be converted into their salts and derivatives by techniques well known in the art. Preferred salts are pharmaceutically acceptable salts. Preferred derivatives are pharmaceutically acceptable derivatives. A derivative that sometimes occurs in small amounts (e.g. <5% wt) is the 6-hydroxy compound. This is produced if the hydrolysis reaction additionally hydrolyses the 6-methoxy group. The 6-hydroxy derivative may be isolated by recrystallisation.

Preferred salts are those that retain the biological effectiveness and properties of the compounds of the present invention and are formed from suitable non-toxic organic or inorganic acids. Adid addition salts are preferred. Representative examples of salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. The modification of a compound into a salt is a technique well known to chemists to obtain improved physical and chemical stability, hygroscopicity, flowability and solubility of compounds.

Preferred compounds of the invention are compounds of formulae (VI), (V), (IV) and (III) as described above wherein $R^1$ is preferably $C_{2-7}$ alkyl, more preferably $C_{3-5}$ alkyl, especially $C_3$ alkyl (e.g. n-propyl). In preferred compounds of formulae (VI) and (V), $R^2$ is $C_{1-3}$ alkyl, more preferably $C_{1-2}$ alkyl, e.g. methyl. In compounds (VI) and (V) of the invention, the stereocentre at carbon 19 is (S).

A preferred compound of formula (VI) is a compound of formula:

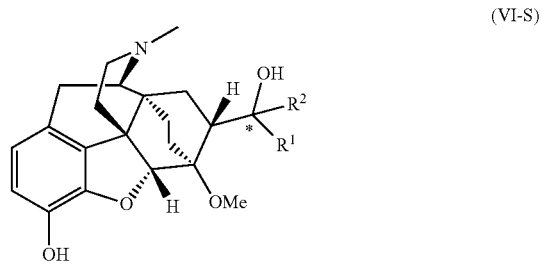

(VI-S)

wherein $R^1$ and $R^2$ are as hereinbefore described (e.g. $R^1$ is $C_{2-7}$ alkyl, more preferably $C_{3-5}$ alkyl, especially $C_3$ alkyl (e.g. n-propyl), $R^2$ is $C_{1-3}$ alkyl, more preferably $C_{1-2}$ alkyl, and the (*) represents a (S) stereocentre.

A particularly preferred compound of formula (VI) is a compound of formula:

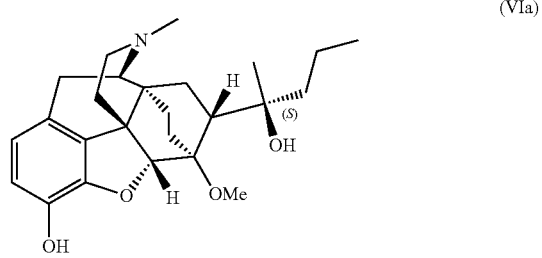

(VIa)

Further preferred compounds of the invention are those that are intermediates in the preparation of compounds of formula (VI). Thus other preferred compounds of the invention are compounds of formula (V-S):

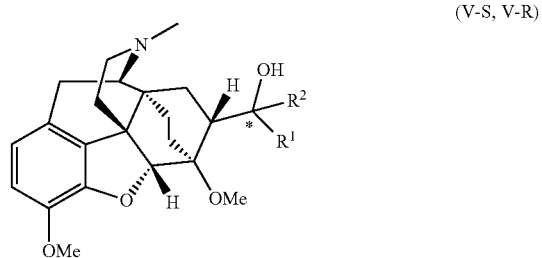

(V-S, V-R)

wherein $R^1$ and $R^2$ are as hereinbefore described (e.g. $R^1$ is $C_{2-7}$ alkyl, more preferably $C_{3-5}$ alkyl, especially $C_3$ alkyl (e.g. n-propyl), $R^2$ is $C_{1-3}$ alkyl, more preferably $C_{1-2}$ alkyl), and the (*) represents a (S) or (R) stereocentre, preferably a (S) stereocentre.

A particularly preferred compound of formula (V) is:

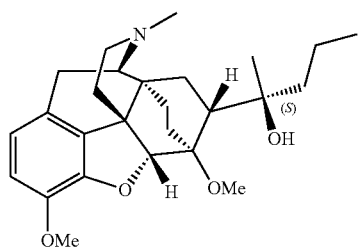

(Va)

Further preferred intermediates are compounds of the formulae (IVa) and (IIIa) as shown below:

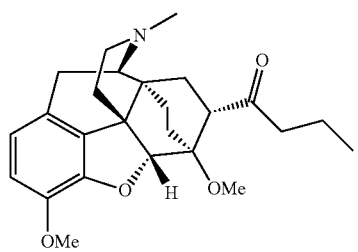

(IVa)

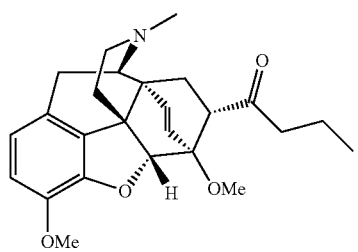

(IIIa)

As described above, the compounds of formula (III), such as (IIIa) above, may be formed by a Diels-Alder reaction with a compound of formula (II). This reaction forms a further aspect of the invention. Preferences for $R^1$ are as hereinbefore described.

The compounds of the present invention have various uses. The compounds (VI-S) can, for example, be used to confirm the (R) chirality of the known dihydroetorphine products. The use of the compounds of the invention in this way is illustrated in the examples that follow hereinafter. The compounds (III) and (IV) of the invention are also useful in the preparation of (R)-dihydroetorphine, which is known to have useful pharmaceutical properties.

Moreover the compounds of formulae (VI-S), (V-S), (V-R), (IV) and (III), especially compounds of formula (VI-S), may be incorporated into compositions, preferably pharmaceutical compositions. Thus, the present invention also includes pharmaceutical compositions comprising a compound of the invention as hereinbefore described (e.g. compounds of formulae (VI-S), (V-S), (V-R), (IV) and (III), especially (VI-S)) and one or more pharmaceutically acceptable carriers. The compounds of the invention, e.g. compounds of formula (VI-S) can be present alone or in combination with another active ingredient in a composition.

The compositions, e.g. pharmaceutical compositions, of the invention may take any conventional form. Preferably, however, the compositions of the invention are prepared in a dosage form suitable for transdermal administration. Alternative preferred compositions of the invention are prepared in a dosage form suitable for parenteral, e.g. intravenous, administration.

By "transdermal" delivery is meant administration of the compounds hereinbefore described to the skin surface of an individual so that the agent passes through the skin tissue and into the individual's blood stream. The term "transdermal" is intended to include transmucosal administration, i.e., administration of the compound to the mucosal (e.g., sublingual, buccal, vaginal, rectal) surface of an individual so that it passes through the mucosal tissue and into the individual's blood stream.

Transdermal dosage forms of the invention include, but are not limited to, mouth pastilles, sprays, aerosols, creams, lotions, ointments, gels, solutions, emulsions, suspensions, or other forms known to one of skill in the art. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g. carriers and diluents) and other materials that can be used to provide transdermal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art.

Depending on the specific tissue to be treated, additional components may be used prior to, in conjunction with, or subsequent to treatment with the compounds of the invention. For example, penetration enhancers can be used to assist in delivering the compound to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Oral gels for sublingual administration of the compounds of the invention (e.g. compounds of formulae (VI-S)) can be prepared by mixing the compound with one or more suitable excipients including flavouring agents. Suppositories for rectal administration of the compounds of the invention (e.g. compounds of formulae (VI-S)) can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition comprising the compounds of the invention can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches. Delivery in this form is particularly preferred.

By intravenous administration is meant administration of the compounds hereinbefore described in the form of a liquid directly into a vein. Dosage forms suitable for intravenous administration include, but are not limited to, solutions, emulsions and suspensions.

Thus viewed from a further aspect, the invention provides a compound as hereinbefore defined, and especially compounds of formula (VI-S), for use as an analgesic, wherein said compound is administered intravenously.

Typically, compositions for intravenous administration comprise sterile isotonic aqueous buffer. Where necessary, the compositions can also include a solubilizing agent. The ingredients may be supplied either separately or mixed together in unit dosage form. For example the ingredients may be supplied separately as a dry lyophilized powder or water free concentrate in a hermetically sealed container, e.g. an ampule or sachette indicating the quantity of active agent, and as an ampoule of sterile water or buffer for mixing prior to administration. Alternatively the composition may be supplied in a pre-mixed form.

The compounds of the invention (e.g. compounds of formulae (VI-S)) may be used in medicine, e.g. to provide analgesia. The doses of compounds required will be dependent, for example, on the subject to be treated, the severity of the pain to be treated, the compound used, the mode of administration etc but will be readily determined by those skilled in the art.

Thus viewed from a further aspect the invention provides a method of treating a subject (e.g. mammal) in need of pain relief comprising administering to said subject a therapeutically effective amount of a compound as hereinbefore described (e.g. a compound of formula (VI-S)). It has also surprisingly been found that in standard tests for nausea and vomiting in ferrets, neither R-DHE nor S-DHE induced nausea or vomiting in similar dose ranges as used in the tests described below.

The compounds of the invention are particularly useful in the treatment of nociceptive and neuropathic pain.

The invention will now be described with reference to the following non-limiting Examples and Figures wherein:

EXAMPLES

Figure 1A:
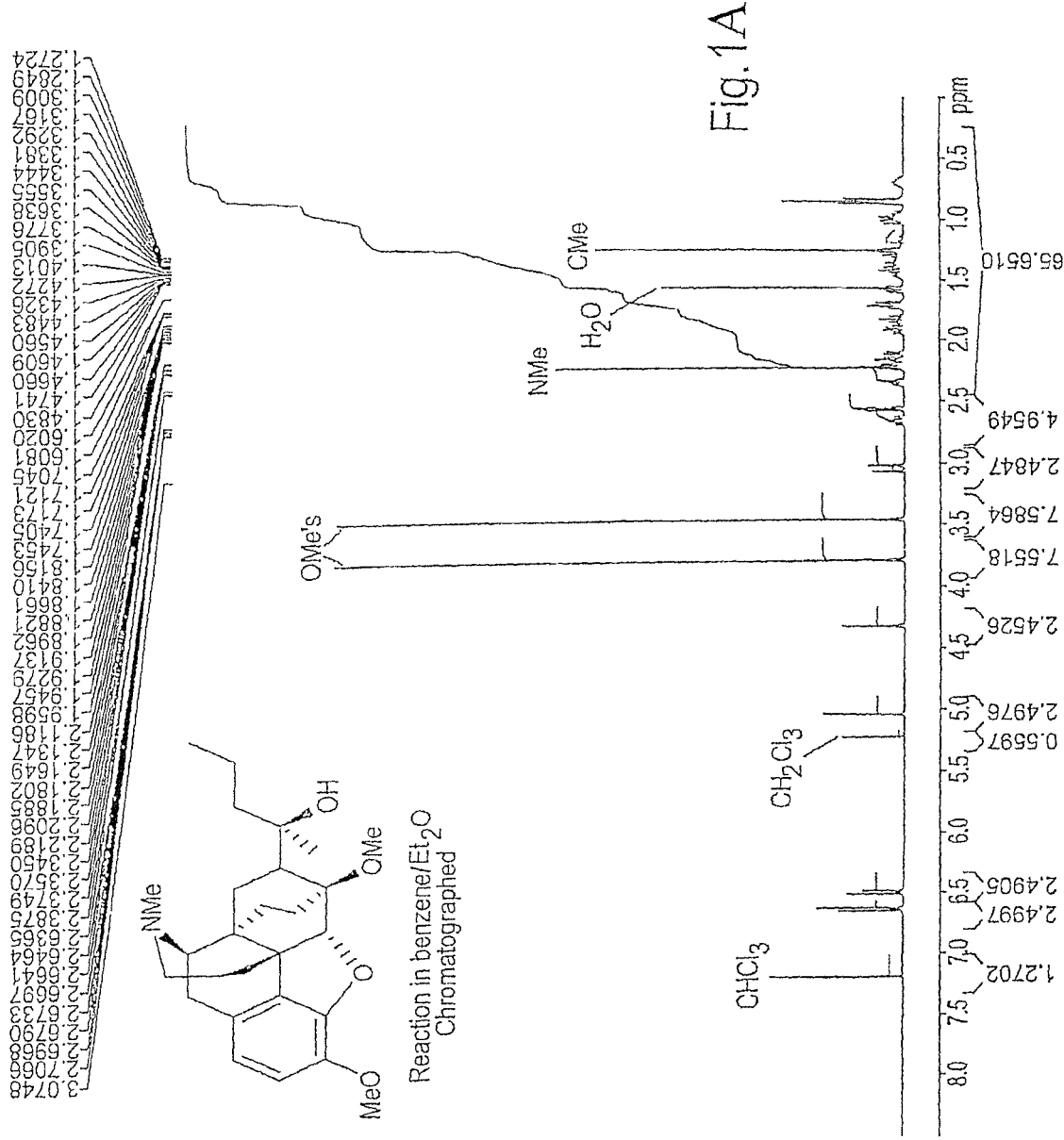
FIG. 1A shows the chemical structure and the 1H NMR spectrum for (R)-19 Propyldihydrothevinol.

Preparation of (S)-Dihydroetorphine
Stage 1—Diels-Alder Reaction

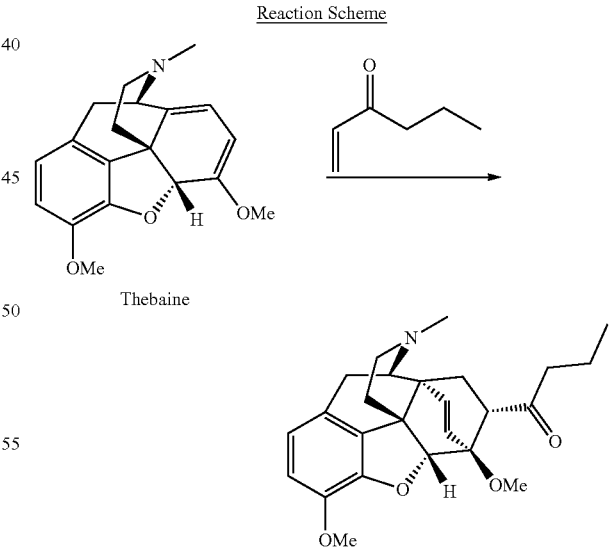

Reaction Scheme

Method

Thebaine was treated with hexen-3-one in a solvent as specified in the table below and heated to reflux. After an appropriate amount of time (overnight), the reaction was cooled and the mixture evaporated. The resulting oil was dissolved in Isopropylacetate (IPAc) and washed with 1M hydrochloric acid solution. The acidic layers were combined and washed with IPAc then basified with sodium bicarbonate solution and finally extracted into dichloromethane (DCM). The DCM layer was evaporated to give a yellow solid.

TABLE 1

Summary of Experiments, Stage 1

| Scale | Conditions | Temp (° C.) | Comments |
|---|---|---|---|
| 500 mg | Benzene (20vols) Hexen-3-one (2.0 mol eq) | Reflux | Overnight reflux gave approx 40% completion |
| 4.5 g | Methanol (10vols) Hexen-3-one (2.0 mol eq) | Reflux | 68% completion by NMR |
| 4.5 g | Ethanol (10vols) Hexen-3-one(7.5 mol eq) | Reflux | >95% completion by NMR. 70% isolated yield |

Using ethanol as the solvent, the final isolated yield of product was 70% as a light yellow solid, after work-up and the quality by $^1$H NMR looked very good.

Stage 2—Hydrogenation

Reaction Scheme

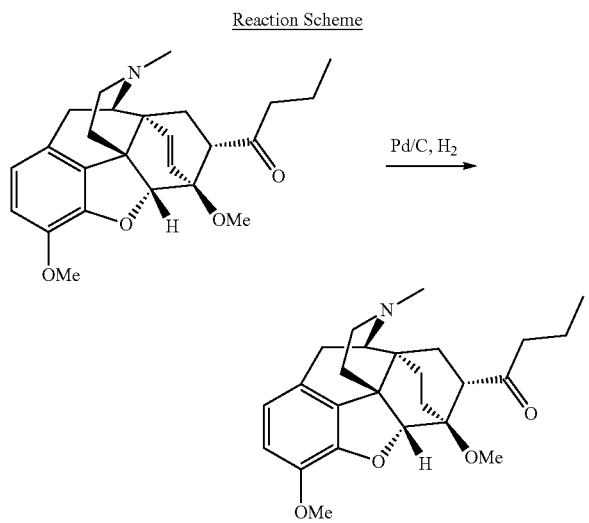

Method

The 19-propylthevinone (4.1 g) intermediate from stage 1 was hydrogenated in ethanol (60 ml) using palladium on carbon (1 g; 10%) under a pressure of hydrogen up to 50 psi. The temperature of the vessel was maintained at ~50° C. and the pressure maintained at 50 psi until no further uptake of hydrogen was noted. The catalyst was filtered and the solvent removed by distillation under vacuum. Isolated yield was 91% in total, giving a 3.8 g of product

TABLE 2

Summary of Experiments, Stage 2

| Scale | Conditions | Temp (° C.) | Comments |
|---|---|---|---|
| 4.1 g | Ethanol (60 ml) 1 g Pd/C (10%) hydrogen (50 psi) | 50° C. | ~91% isolated yield |

Stage 3—Grignard Addition

Reaction Scheme

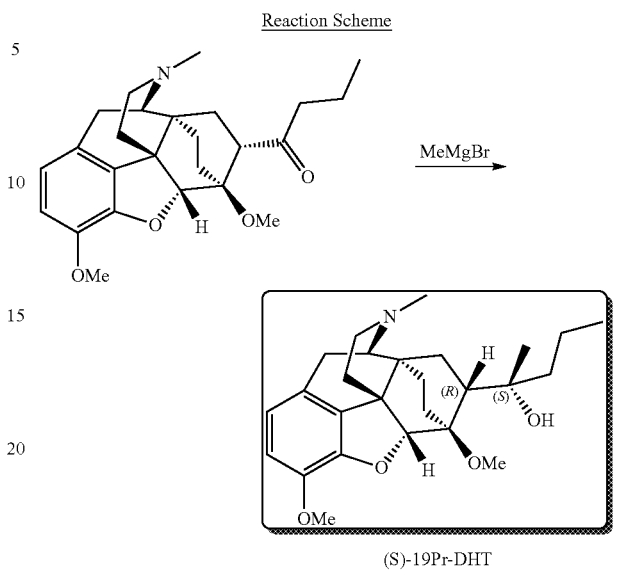

(S)-19Pr-DHT

Method 19-propyldihydrothevinone (Stage 2 product) was dissolved in diethyl ether (35 vols). Methyl magnesium bromide (92.6 mol. eq.) was added to this solution over 5 minutes at 20-25° C. (small exotherm). The resulting mixture was then heated to ~40° C. internal temperature for ~2 hours, before cooling and quenching with ammonium chloride solution. The mixture was extracted with 2-methyl THF and the organic layers evaporated in vacuo to give a viscous oil.

TABLE 3

Summary of Experiments, Stage 3

| Scale | Conditions | Temp (° C.) | Comments |
|---|---|---|---|
| 0.13 g | 2-diethyl ether (25 vols) 3M MeMgBr (1.5 eq) | 40° C. | Good quality material produced |
| 0.79 g | 2-diethyl ether (25 vols) 3M MeMgBr (1.5 eq) | 35° C. | Stirred overnight. 93% purity after work-up. Crude product triturated in methanol to give 0.32 g pure material and 0.5 g impure residues. |
| 2.2 g | 2-diethyl ether (35 vols) 3M MeMgBr (2.6 eq) | 35° C. | 2.6 g crude (~90% pure) isolated. Triturated in methanol to give 1.6 g of pure material. |

The sole product of the Grignard addition is the (S)-enantiomer. No (R)-enantiomer was detected.

Stage 4—Crystallisation of (R) and (S)-19-Propyldihydrothevinol

In order to prepare a single crystal of high quality for x-ray crystallography, a series of experiments were run in many solvents to determine the best solvent system for growing a single crystal of 19-propyldihydrothevinol. The experiments are summarized in table 4 below. The R-enantiomer was prepared using an alternative method.

In general the crystallisation method used was as follows: a small amount of solid 19-propyldihydrothevinol (obtained from Stage 3) was dissolved in just over the minimum amount of solvent. The solution was allowed to stand for up to 3-4 days and the solvent removed by filtration or decanting in order to isolate single crystals.

TABLE 4

Summary of Re-crystallisations

| Solvent | Co-solvent | Diastereoisomer | Temperature | Crystals | Comments |
|---------|-----------|-----------------|-------------|----------|----------|
| MTBE | None | (S) | RT | Yes | High quality - submitted for X-ray |
| AcCN | None | (S) | RT | Yes | High quality |
| DCM | None | (R) | Dissolved Hot | Yes | High quality - submitted for X-ray |
| Acetone | None | (R) | Dissolved Hot | Yes | High quality - submitted for X-ray |
| Ethanol | None | (R) | Dissolved Hot | Yes | High quality - submitted for X-ray |

Figure 1B:
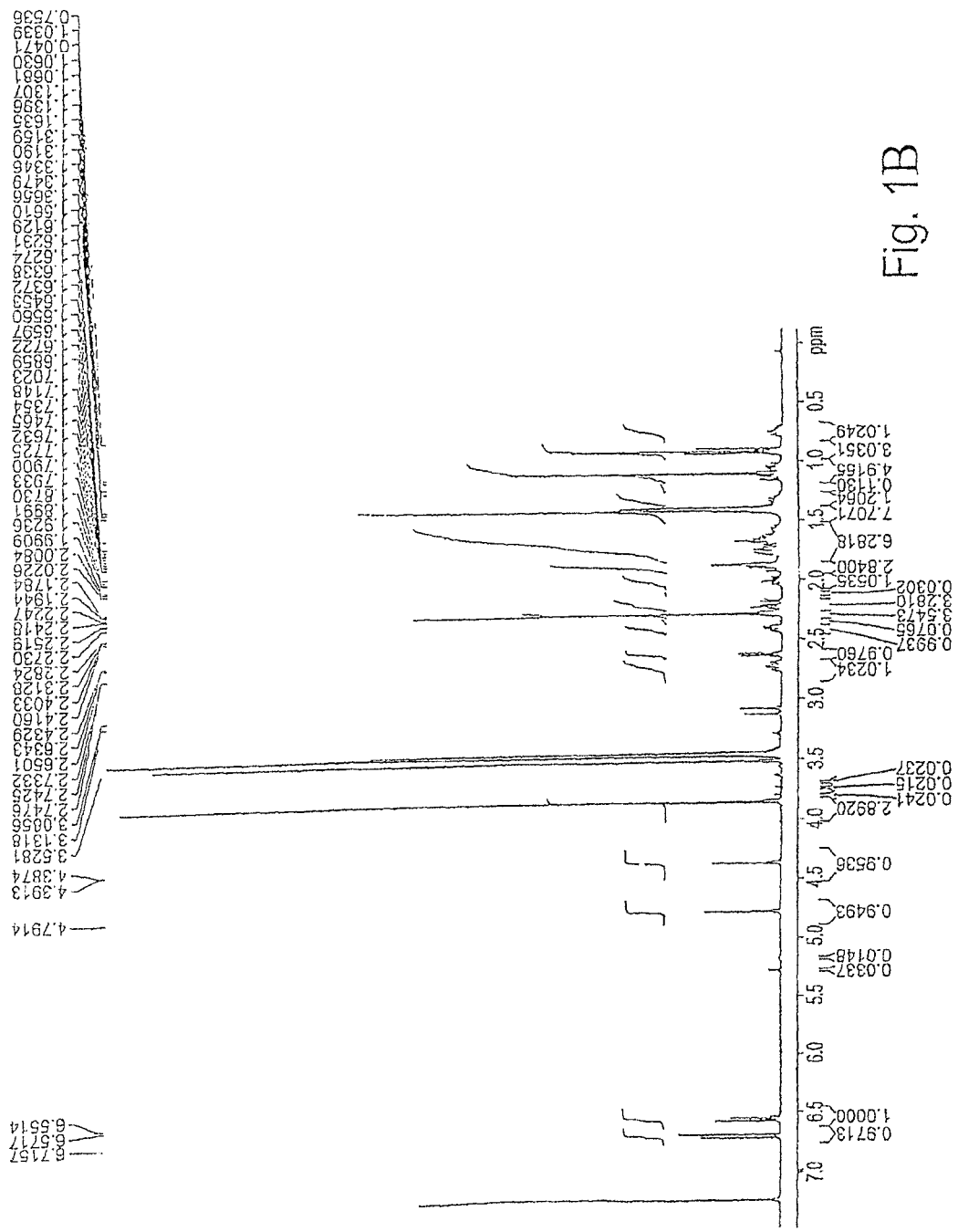
FIG. 1B shows the 1H NMR spectrum for (S)-Propyldihydrothevinol.

The $^1$H NMR spectra for each of the diastereomers are shown in FIG. 1A and FIG. 1B.

Stage 5—Hydrolysis of (S)-19-Propyldihydrothevinol

Reaction Scheme

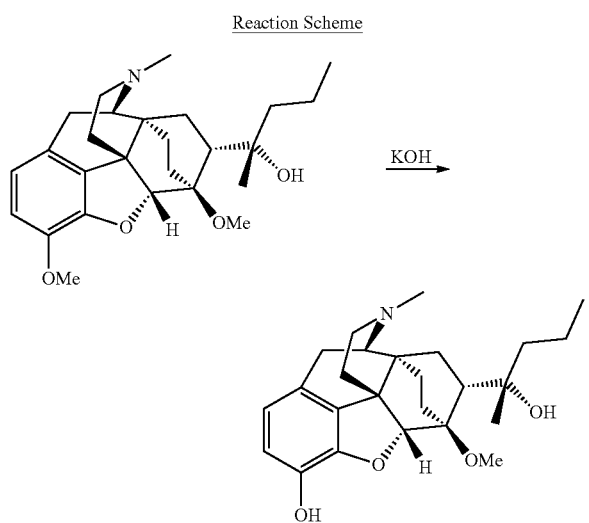

Method

The (S)-19-propyldihydrothevinol (from Stage 3) was dissolved in diethylene glycol (17 vols) and treated with potassium hydroxide (~20 eqs) and heated to ~195° C. for 12-18 hours. After this time, the reaction mixture was cooled to room temperature and quenched into water (40 vols). The resulting solution was acidified to pH 9-10 using solid ammonium chloride and the mixture extracted with DCM (3×50 vols). The combined organic extracts were evaporated in vacuo to a crude oil (approx. 40% purity). The purity was increased with repeated triturations in methanol until a yellow solid was formed and isolated in good purity (>95%).

The product was recrystallised from several solvents and crystals were obtained from acetonitrile. These were used for X-ray crystallographic studies.

R-enantiomer was obtained using an analogous reaction.

X-Ray Crystallography Studies

All X-ray crystallography experiments were carried out on an Oxford Xcalibur single crystal diffractometer or a Nonius Kappa diffractometer. Both machines were using Molybdenum K alpha X-ray sources and CCD detectors.

(R) and (S) 19-propyldihydrothevinol

Several batches of both (R) and (S) 19-propyldihydrothevinol were submitted for X-ray crystallography.

The X-ray structures are shown in FIGS. 2-5.

Figure 2:
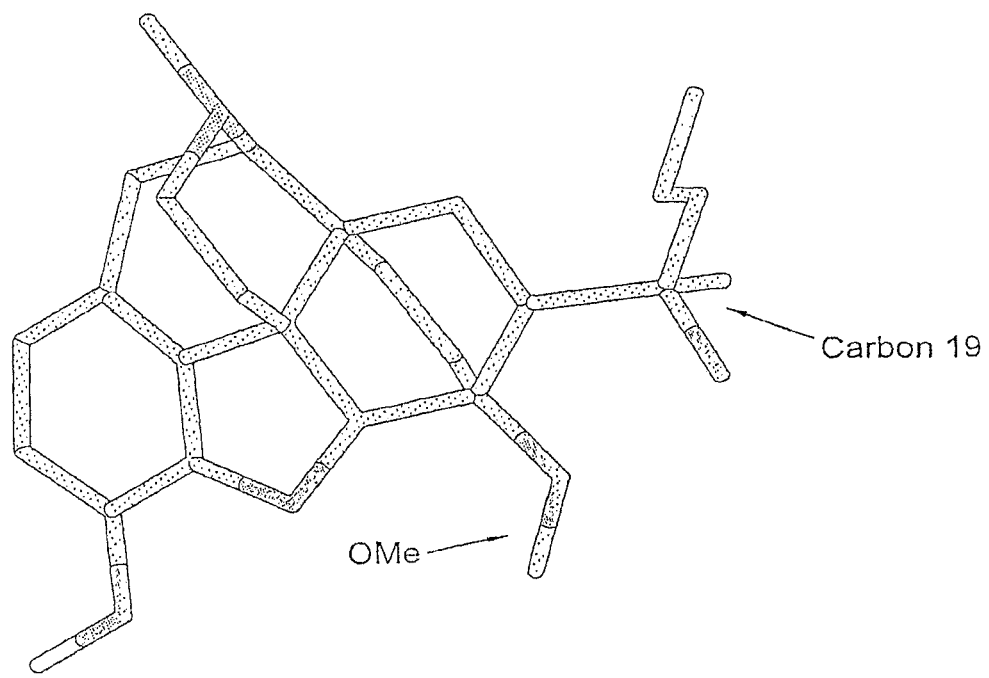
FIG. 2 shows the chemical structure and the X-ray structure of (R)-19 Propyldihydrothevinol depicting (R)-configuration at carbon 19 and (R)-configuration of the methyl ether.
Figure 2:
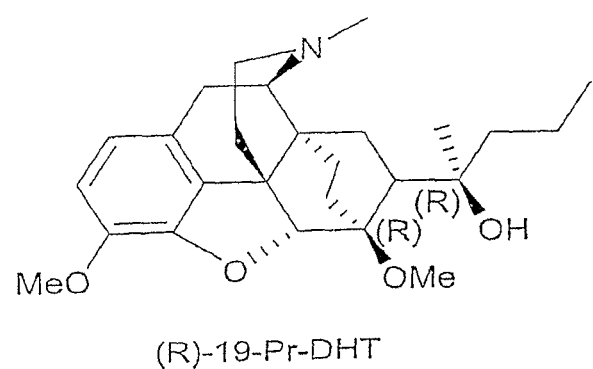
Figure 3:
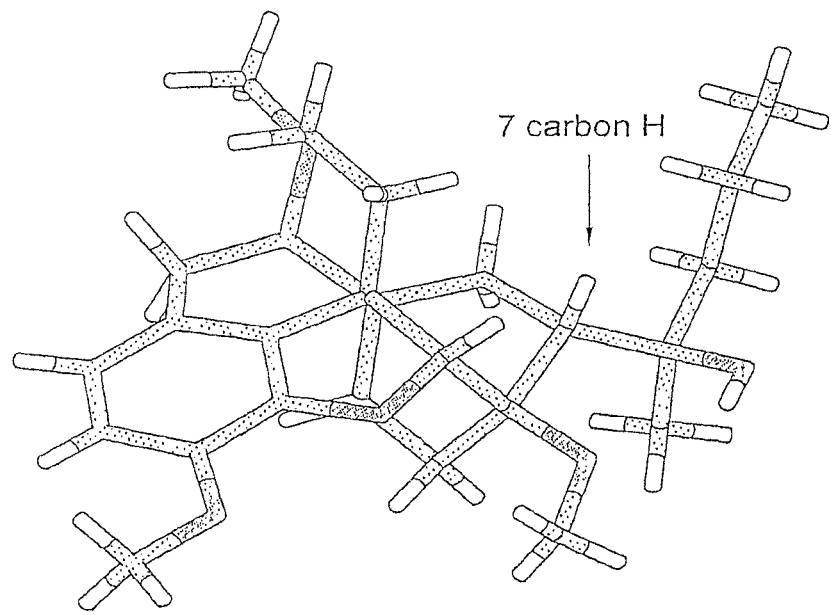
FIG. 3 shows the chemical structure and the X-ray structure of (R)-19 Propyldihydrothevinol depicting the hydrogen atoms at the 7 position and at the 5 position on the same face giving the configuration as (R).
Figure 3:
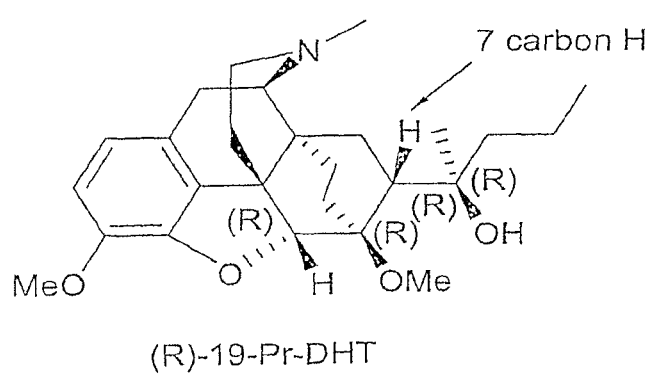

FIGS. 2 and 3 show the X-ray structure of (R)-19 Propyldihydrothevinol. From the X-ray it can be clearly seen that it has the (R)-configuration at carbon 19. This can be assigned with respect to chiral methyl ether, which retains the (R)-configuration from the thebaine starting material.

Additionally from FIG. 3, where the hydrogen atoms are showing, it can be seen that the hydrogen at the 7 position is on the same face as the hydrogen at position 5 (next to the furan ring), giving the configuration as (R).

Figure 10:
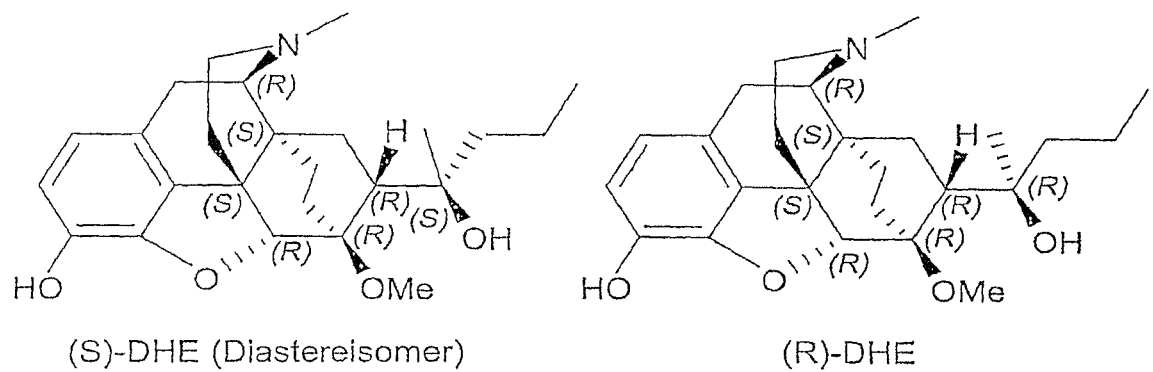
FIG. 10 shows the stereochemistry of all of the chiral carbons present in (R)- and (S)-Dihydroetorphine.

In this way all of the chiral carbons have now been assigned and are depicted in FIG. 10.

TABLE 6

Other Information (R)-19-Propyldihydrothevinol

| Property | Value |
|----------|-------|
| Symmetry cell setting | Monoclinic |
| Symmetry space group name | H-M P2(1) |
| Loop symmetry equiv pos as xyz | 'x, y, z' |
| | '-x, y + ½, -z' |
| Cell length a | 11.0464(6) |
| Cell length b | 12.4554(7) |
| Cell length c | 16.2271(7) |
| Cell angle alpha | 90.00 |
| Cell angle beta | 98.481(5) |
| Cell angle gamma | 90.00 |
| Cell volume | 2208.2(2) |

Figure 4:
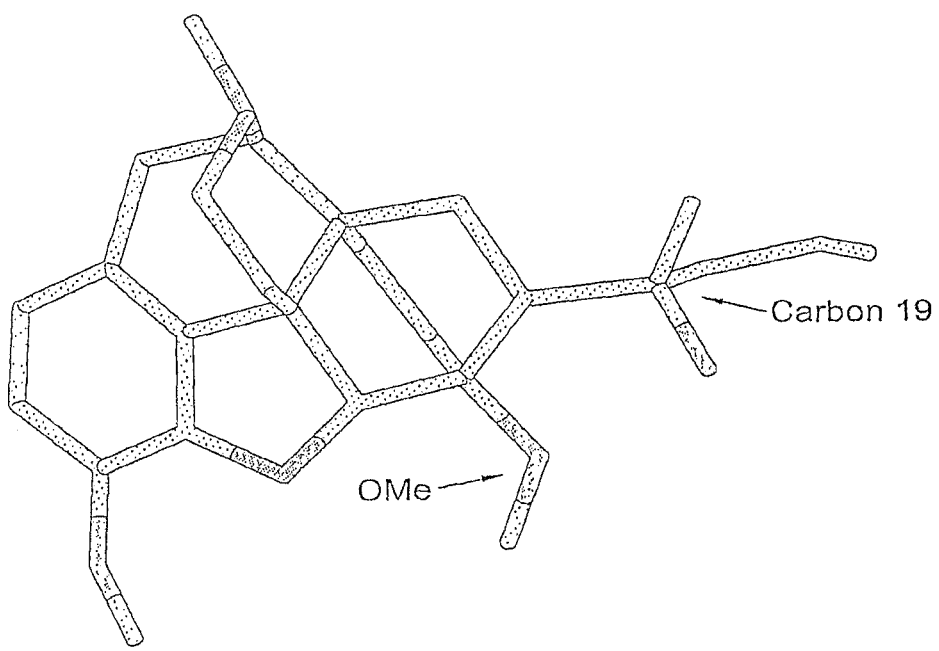
FIG. 4 shows the chemical structure and the X-ray structure of (S)-19 Propyldihydrothevinol depicting the (S) configuration at carbon 19 and (R)-configuration of the methyl ether.
Figure 4:
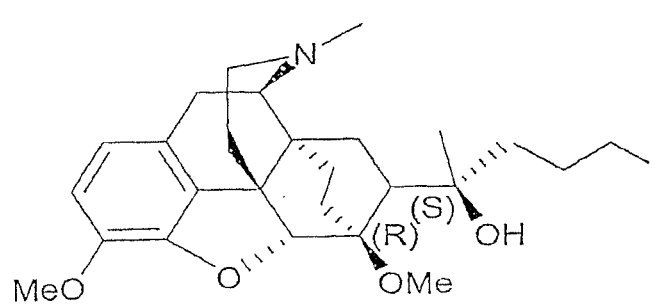
Figure 5:
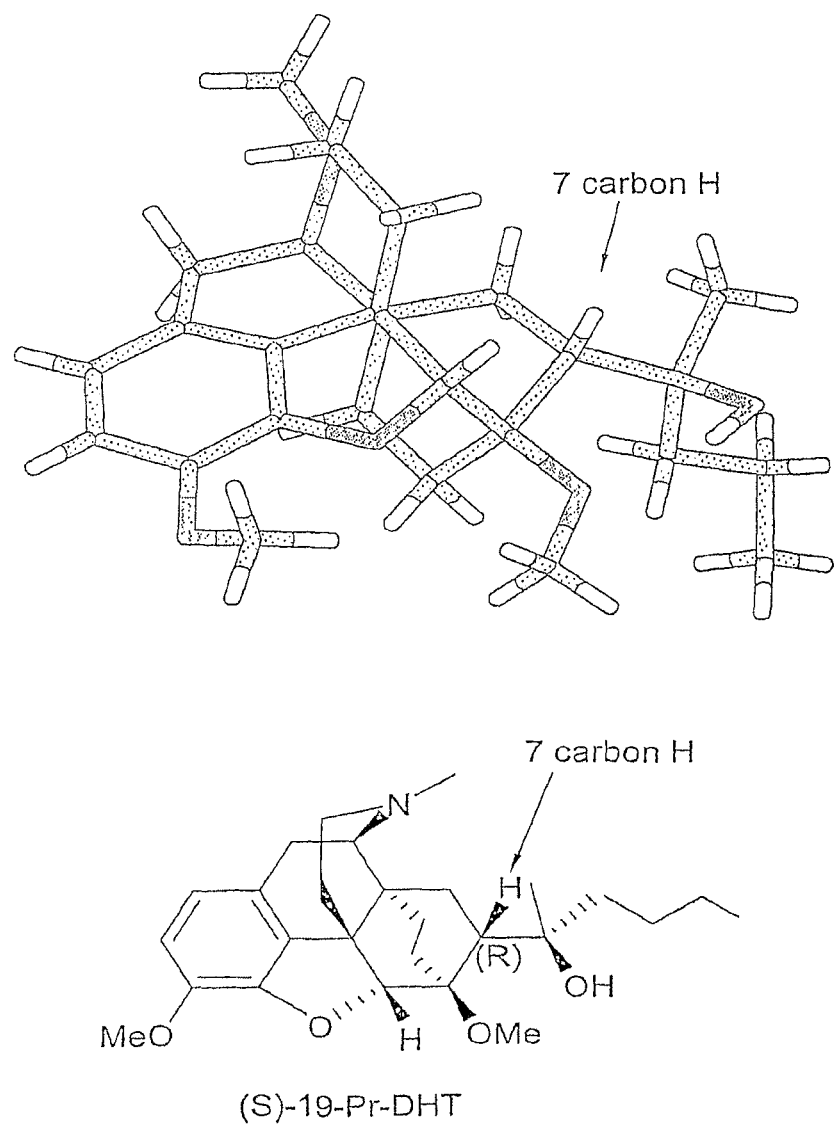
FIG. 5 shows the chemical structure and the X-ray structure of (S)-19 Propyldihydrothevinol depicting the configuration of the 7-carbon hydrogen as (R).

FIGS. 4 and 5 show the X-ray structure of (S)-19-Propyldihydrothevinol.

From FIG. 4 it can be clearly seen that it has the opposite stereochemistry of (S)-configuration at carbon 19 to the crystal shown in FIG. 3. This can be assigned with the respect to chiral methyl ether, which retains the (R)-configuration from thebaine starting material.

Again the 7-carbon hydrogen (show in FIG. 5) shows that the configuration at this carbon is also (R), as with the first diastereoisomer.

Therefore we can now safely conclude that the only difference between the 2 compounds by X-ray crystallography is the stereoconfiguration at carbon 19.

TABLE 7

Other Information (S) 19-Propyldihydrothevinol

| Property | Value |
|----------|-------|
| Symmetry cell setting | Monoclinic |
| Symmetry space group name | H-M P2(1) |
| Loop symmetry equiv pos as xyz | 'x, y, z' |
| | '-x, y + ½, -z' |
| Cell length a | 13.8650(3) |
| Cell length b | 10.8560(2) |
| Cell length c | 15.4030(4) |
| Cell angle alpha | 90.00 |
| Cell angle beta | 99.7500(8) |
| Cell angle gamma | 90.00 |
| Cell volume | 2284.95(9) |

(R) and (S)-Dihydroetorphine

The X-ray structures are shown in FIGS. 6-9.

Figure 6:
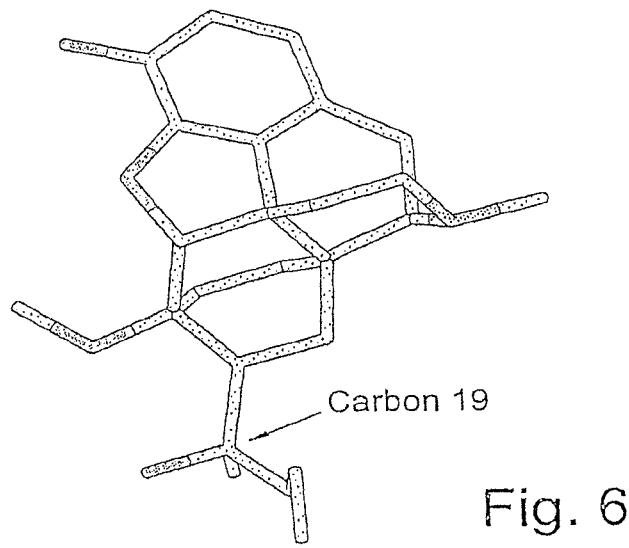
FIGS. 6 and 7 show the X-ray structure of (R)-Dihydroetorphine depicting the (R)-configuration at carbon 19.
Figure 7:
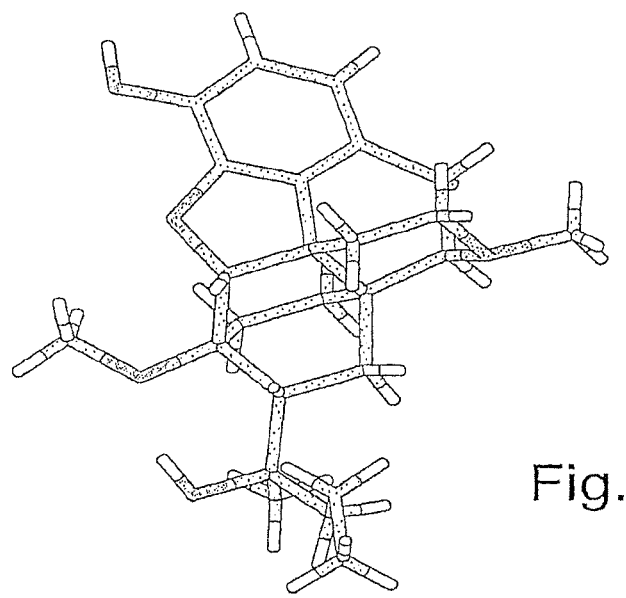

FIGS. 6 and 7 shows the X-ray structure of (R)-dihydroetorphine. It can clearly be seen from these Figures that it has the (R) configuration at carbon 19. This can be assigned with respect to the chiral methyl ether, which retains the (R)-configuration from the original starting material, thebaine.

TABLE 8

Other Information (R)-Dihydroetorphine

| Property | Value |
|---|---|
| Symmetry space group name | P 2₁ 2₁ 2 |
| Loop symmetry equiv pos as xyz | 'x, y, z ', '-x, ½ + y, -z' |
| Cell length a | 16.3405(7) |
| Cell length b | 35.605(2) |
| Cell length c | 7.5209(3) |
| Cell angle alpha | 90.00 |
| Cell angle beta | 90.00 |
| Cell angle gamma | 90.00 |
| Cell volume | 4375.69 |

Figure 8:
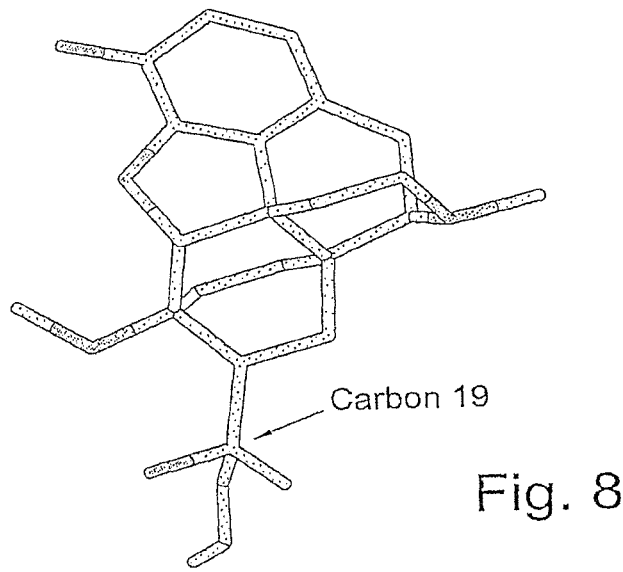
FIGS. 8 and 9 show the X-ray structure of (S)-Dihydroetorphine depicting the (S)-configuration at carbon 19.
Figure 9:
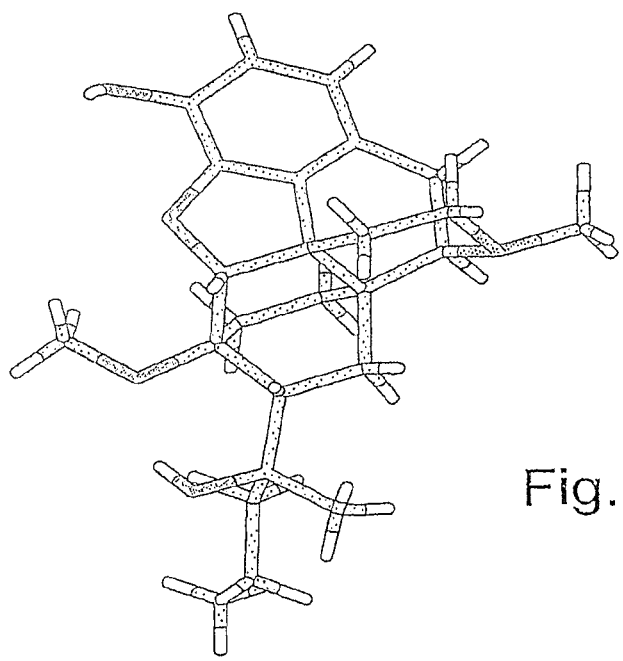

FIGS. 8 and 9 show the X-ray structure of (S)-dihydroetorphine. It can clearly be seen from these Figures that it has the (S) configuration at carbon 19. This can be assigned with respect to the chiral methyl ether, which retains the (R)-configuration from the original starting material, thebaine.

Additionally the 7-carbon hydrogen (shown in FIG. 9) shows that the configuration at this carbon is also (R), as with the first diastereoisomer.

Therefore it can be concluded that the only difference between the 2 compounds by X-ray crystallography is the stereoconfiguration at carbon 19.

TABLE 9

Other Information (S)-Dihydroetorphine

| Property | Value |
|---|---|
| Symmetry space group name | H-M P2(1) |
| Loop symmetry equiv pos as xyz | 'x, y, z ', Rotation axis (2 fold): '-x, -y, z' Screw axis (2 fold): '½ - x, ½ + y, -z' Screw axis (2 fold): '½ + x, ½ - y, -z' |
| Cell length a | 7.2310(3) |
| Cell length b | 14.0795(6) |
| Cell length c | 10.6984(5) |
| Cell angle alpha | 90.00 |
| Cell angle beta | 96.226(4) |
| Cell angle gamma | 90.00 |
| Cell volume | 1082.77 |

Optimisation of Process

The following methods and equipment were used:

Method 38XB and UFC-LC-MUN-1 are a reverse phase, gradient HPLC procedures using an Xbridge C18 column and a mobile phase consisting of acetonitrile and 0.01M ammonium acetate pH 9.2.

NMR was carried out using a Bruker Avance 400 MHz spectrometer

MS was carried out using a ZMD Micromass mass spectrometer

LC was carried out using an Agilent 1100 HPLC system

Stage 1: Diels-Alder Reaction

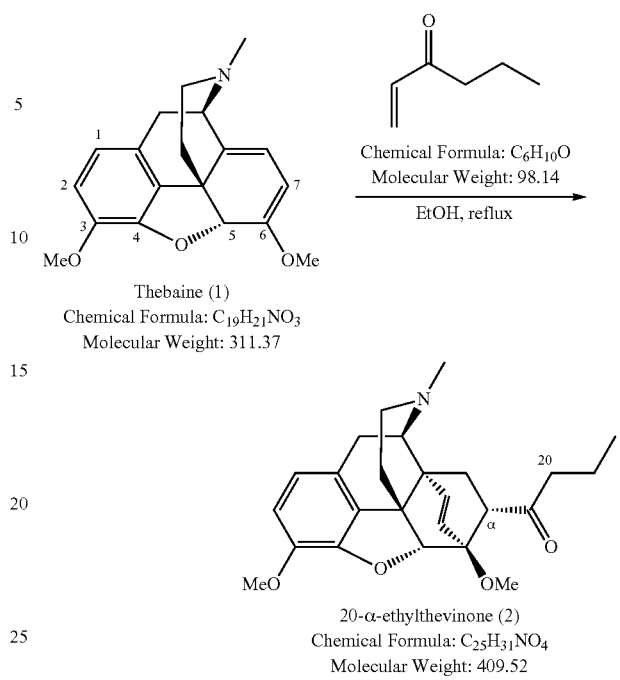

Thebaine (1)
Chemical Formula: $C_{19}H_{21}NO_3$
Molecular Weight: 311.37

20-α-ethylthevinone (2)
Chemical Formula: $C_{25}H_{31}NO_4$
Molecular Weight: 409.52

The initial method employed was as described above. The main contaminant was identified as the 7β-isomer shown below.

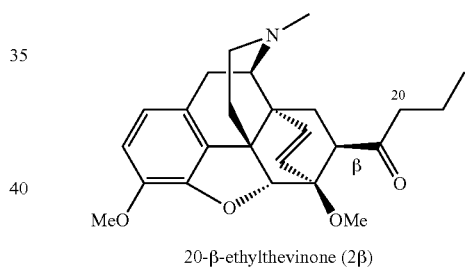

20-β-ethylthevinone (2β)

It was subsequently discovered that both the purity and recovery of 20-α-ethylthevinone could be improved by reducing the 1-hexen-3-one charge from 2.8 equivalents to 1.8 equivalents, Table 10. A further improvement was achieved by using 1.5 equivalents of 1-hexen-3-one (added in 2 portions of 1.4 eq and 0.1 eq) and upon completion of the reaction, removing 0.5 volumes of solvent via distillation. Upon cooling the resulting solution the product precipitated as a solid (aged for 1 hr) and was filtered.

Procedure: To a 1 L (3-neck) flask fitted with an overhead stirrer and reflux condenser the following were charged, thebaine (0.32M, 100 g, 1 eq), EtOH (250 mL) and 1-hexen-3-one (90%, 0.45M, 58 mL, 1.4 eq). The mixture was heated at reflux for 13 hrs and analysed by ¹H NMR and found to contain starting material (~4.5 molar %). An additional 0.1 eq of 1-hexene-3-one was added and the mixture heated for a further 2 hrs, before stirring overnight at room temperature. Analysis showed starting material (~2.8 molar %). The material was transferred to a round bottomed flask (500 mL) (flask washed with EtOH 20 mL). EtOH (~65 mL) was removed in vacuo at 50° C. and the resulting precipitated solid stirred at 5° C. for 1 hr before filtering. The solid was washed with ice-cold EtOH (4×20 mL) and pulled dry on the filter for ~1.5 hrs. White solid (105.4 g, 80%).

TABLE 10

| Scale | Conditions | Temp (° C.) | Comments |
|---|---|---|---|
| 10 g | 1 eq thebaine<br>2.8 eq 1-hexen-3-one<br>2.5 vol EtOH | Reflux<br>(bath temp<br>94° C.) | Yield 69%, 9.03 g,<br>contains 6% of 7β-isomer -<br>92% purity |
| 2 g | 1 eq thebaine<br>1.8 eq 1-hexen-3-one<br>2.5vol EtOH | Reflux<br>(bath temp<br>94° C.) | Yield 55%, 1.44 g. Material<br>precipitated on cooling -<br>>99.5% purity |
| 100 g | 1 eq thebaine<br>1.5 eq 1-hexen-3-one<br>2.5 vol EtOH | Reflux<br>(bath temp<br>101° C.) | Yield 80%, 105.4 g.<br>Material precipitated.<br>>99.5% purity |

Analytical Methods and in-Process-Checks (IPCs)

$^1$H NMR (400 MHz) was used for IPCs plus HPLC method 38XB during lab work. Reaction was deemed complete when <5 molar % starting material remained by $^1$H NMR based on the signals at δ 5.05 ppm and 5.3 ppm (CDCl$_3$)

For confirming purity and for LC-MS work method UFC-LC-MUN-1 was used in the analytical lab.

TLC (5% MeOH/95% DCM) Iodoplatinate stain: R$_f$=0.25 Thebaine, R$_f$=0.66 (7α)-20-ethylthevinone.

Analytical Summary

| Appearance | HPLC (% a/a) | | |
|---|---|---|---|
| | 7α 20-ethylthevinone | Thebaine | 7β 20-ethylthevinone |
| RT/RRT | 10.69/1.0 | 5.82/0.54 | 11.67/1.09 |
| White solid | >99.5 | none | None |

$^1$H NMR (CDCl$_3$, 400 MHz); δ=0.80 (3H, t), 1.4 (1H, m), 1.6 (3H, sext.), 1.9 (1H, d), 2.0 (1H, br), 2.4-2.6 (8H, m), 2.9 (2H, br), 3.35 (2H, d), 3.6 (3H, s), 3.85 (3H, s), 4.6 (1H, s), 5.6 (1H, d), 6.0 (1H, d), 6.55 (1H, d), 6.7 (1H, d)

$^{13}$C NMR (CDCl$_3$, 75 MHz); δ=13.71, 16.89, 22.49, 30.25, 43.26, 43.51, 45.57, 45.72, 47.40, 49.94, 53.78, 56.68, 60.06, 81.52, 95.84, 113.61, 119.36, 125.89, 134.07, 135.53, 141.87, 148.07

MS; [M+H]$^+$=410.3

LC; >99.5% purity

TLC; 5:95; MeOH:DCM; single spot rf=0.66

Advantages of Optimised Process

Increased yield to 80%

Amount of 1-hexen-3-one has been reduced to 1.5 equivalents with no decrease in conversion or yield.

Decrease in equivalents of 1-hexen-3-one allows for an improved isolation (direct crystallisation from reaction solvent), which gives material of very high purity.

Volume efficiency is very high (maximum ~4 volumes total).

Purity improved to >99% (by HPLC).

IPC shows completion at >97% conversion by $^1$H NMR (<3% thebaine).

Stage 2 Hydrogenation

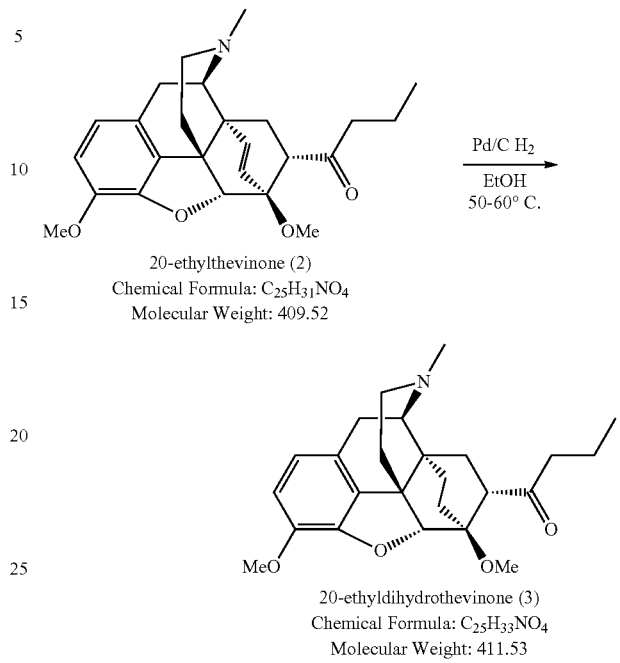

20-ethylthevinone (2)
Chemical Formula: C$_{25}$H$_{31}$NO$_4$
Molecular Weight: 409.52

20-ethyldihydrothevinone (3)
Chemical Formula: C$_{25}$H$_{33}$NO$_4$
Molecular Weight: 411.53

The results of the development work for the hydrogenation stage are outlined in Table 11 below. The reaction has been 'stressed' both in terms of catalyst loading and reaction temperature. In addition, by reducing the reaction volume from 17 vol to 12 vol, the quality of the product and isolation of the product has been improved.

Interestingly both the starting material and product are thermally stable to ~80° C. over 1-2 hours which allows for higher reaction temperature, increasing solubility of both the starting material and product, during reaction. It was found that in this case the solubility was key to good reactivity and higher temperatures were employed during scale-up to achieve completion of reaction.

In the final scale-up reaction the temperature increased out of "normal" range during the initial heating of the reaction vessel and a fast reaction was observed (hydrogen uptake). On reducing the temperature to 55° C. the reaction decreased significantly and only on further addition of catalyst and an increase in temperature to ~65° C. did the reaction achieve completion.

Isolation of the product was simplified by warming the reaction mixture to 77° C., allowing sub-reflux temperature to occur and then filtering the catalyst from the reaction mixture. The resulting solution was initially reduced in volume by distillation, however it was found that the solution could be cooled in an ice bath and high purity material was isolated by filtration of the crystallised solid in good yield (72%).

Procedure: 20-Ethylthevinone (0.244M, 100 g) was charged to a 2 L Parr hydrogenation vessel. 10% Pd/C (50% wet, 10 g) was slurried in EtOH (200 mL) and charged to the hydrogenation vessel. EtOH (1 L) was charged to the vessel, the vessel was sealed and inerted with argon (×4). The vessel was refilled with hydrogen to 50 psi (×2) and finally left at 50 psi. The temperature was set to 35° C. The internal temperature peaked at 82° C. and was allowed to cool back to room temperature overnight (pot exotherm). The vessel was refilled with $H_2$, sampled and analysed by LC and found not to be complete. The vessel was heated to an internal temperature of 55-65° C. and the reaction progress monitored by LC—the hydrogen pressure was maintained at 50 psi throughout by periodic refills. After 24 hrs an additional catalyst charge (5 g) was made and the reaction continued. After an additional 16 hrs the reaction was complete by LC and $^1$H NMR. The internal temperature was raised to 68° C. and the mixture transferred under vacuum to a 3 L rbf. The Parr vessel was flushed with hot EtOH (200 mL) and the wash transferred to the rbf. The mixture was heated to 77° C. before filtering (GF/F paper). The catalyst bed was washed with hot EtOH (1×300 mL) and the filtrate allowed to cool to room temperature. The filtrate was cooled in an ice-water bath for 50 min before filtering. The collected solid was washed with ice-cold EtOH (1×100 mL), heptane (1×300 mL) and pulled dry for 1.5 hrs. White solid (72 g, 72%).

Analysis $^1$H NMR (CDCl$_3$, 400 MHz); δ=0.75 (1H, t, t), 0.9 (1H, t), 1.35 (1H, t, d), 1.5-1.75 (7H, m), 2.1 (1H, t, d), 2.3 (5H, m), 2.5 (2H, q), 2.6-2.7 (3H, m), 3.0 (1H, q, t), 3.1 (1H, d), 3.5 (3H, s), 3.9 (3H, s), 4.5 (1H, d), 6.6 (1H, d), 6.7 (1H, d).

$^{13}$C NMR (CDCl$_3$, 75 MHz); δ=13.73, 16.99, 17.31, 21.98, 28.67, 30.70, 35.17, 35.66, 43.51, 45.24, 45.78, 48.28, 48.91, 52.26, 56.76, 61.35, 94.96, 114.01, 119.16, 128.71, 132.47, 141.76, 146.80

LC; >99%

Residual Solvent (by $^1$H NMR); No residual ethanol

Advantages of Optimised Process

Reducing the reaction volume from 17 vol to 12 vol allows the direct crystallisation of the product.

Product isolated in 72% yield with a purity >99%.

A temperature of about 65° C. would appear to be optimum for solubility and reactivity. Drying the solid on the filter bed and washing with heptane removes ethanol traces to an acceptable level ready for the next stage.

TABLE 11

| Scale | Conditions | Temp (° C.) | Comments |
|---|---|---|---|
| 4.5 g | 1 eq 20-ethylthevinone, Pd/C (50% wet, 2.71 g), 14vol EtOH, 25 psi H$_2$ | Pot temp 55° C. | After 16 hrs, 1 g sample (0.7% SM left) was removed. Reaction continued until complete. Yield 90%, 3.4 g |
| 0.680 g | 1 eq 20-ethylthevinone, Pd/C (50% wet, 0.034 g), 70vol EtOH, 50 psi H$_2$ | Pot temp 55° C. | Yield 85%, 0.580 g |
| 2.32 g | 1 eq 20-ethylthevinone (547-089-1), Pd/C (50% wet, 0.232 g), 17vol EtOH, 50 psi H$_2$ | Pot temp 55° C. | After 16 hrs reaction complete. Reaction filtered, concentrated to ~⅓ vol and ppt collected. Yield 64%, 1.494 g |
| 0.6 g | 1 eq 20-ethylthevinone (547-090-1), Pd/C (50% wet, 0.60 g), 17vol EtOH, 50 psi H$_2$ | Pot temp 55° C. | Reaction complete after 16 hrs. Workup not complete. |
| 100 g | 1 eq 20-ethylthevinone, Pd/C (50% wet, 15 g), 12 vol EtOH, 50 psi H$_2$ | Maximum pot temp 82° C. Optimal temp ~60° C. | Product crystallised from reaction mixture after removal of catalyst. Yield 72%, purity >99% |

Analytical Methods and in-Process-Checks $^1$H NMR (400 MHz) was used for IPCs plus HPLC method 38XB during lab work. Reaction progress was monitored by LC analysis: the reaction carried out on the 100 g scale showed no 20-ethylthevinone and 96% of 20-ethyldihydrothevinone.

For confirming purity and for LC-MS work method product from the 100 g scale reaction was used in the analytical lab.

Analytical Results

| Appearance | HPLC (a/a %) | Comments |
|---|---|---|
| White solid | >99 | No 20-ethylthevinone remained. No other impurity detected. |

Stages 3 and 4: Grignard and Crystallisation

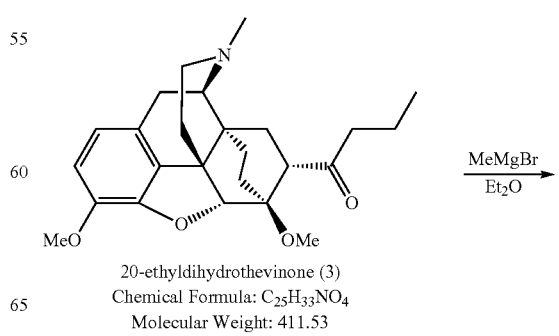

20-ethyldihydrothevinone (3)
Chemical Formula: C$_{25}$H$_{33}$NO$_4$
Molecular Weight: 411.53

-continued

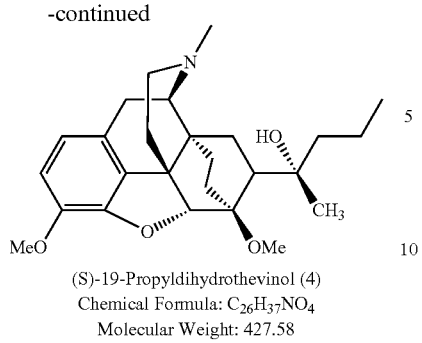

(S)-19-Propyldihydrothevinol (4)
Chemical Formula: $C_{26}H_{37}NO_4$
Molecular Weight: 427.58

The results of the work are summarised in Table 12 below. Different ethereal solvents were investigated, with diethyl ether giving the best quality material, although the difference between diethyl ether and MTBE was found to be relatively minor.

Generally, the crude material obtained from the Grignard reaction contained two main impurities (~10% of each, LC-MS). Both impurities have the same mass $[M+H]^+$ = 428.4) as the product). One of the two impurities has been tentatively assigned as the constitutional isomer, which results from the ring-closure ring-opening reaction of excess Grignard reagent on 20-ethyldihydrothevinone.

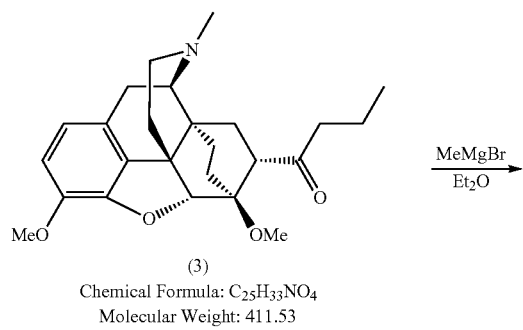

The second impurity, which has a similar retention time (LC-MS) to the product is believed to be the diastereoisomer (R)-19-propyldihydrothevinol.

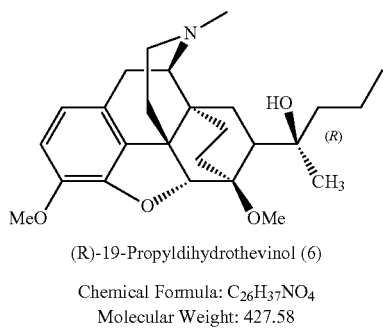

(R)-19-Propyldihydrothevinol (6)
Chemical Formula: $C_{26}H_{37}NO_4$
Molecular Weight: 427.58

Both impurities are removed efficiently by the methanol re-crystallisation.

The role of the reaction temperature was investigated with diethyl ether and it was found that the reaction profile, both in terms of reaction progress and impurities (LC analysis) were comparable at room temperature and at reflux temperature.

Thus, the observed differences in purity noted in the reactions are thought to arise from the different purification procedures (re-crystallisation using an oil bath and reflux condenser with magnetic stirrer, or trituration via rotation on a rotary evaporator with methanol).

Methylmagnesiumiodide was also utilised and gave comparable results to the bromide.

Procedure: 20-Ethyldihydrothevinone (0.073M, 30 g) was dissolved (cloudy solution) in anhydrous diethyl ether (1050 mL; 35 vols). Methylmagnesium bromide (0.189M, 63 mL) was added drop wise over 1 hr maintaining the internal temperature below 28° C. The resulting white suspension was heated at reflux for 5 hrs, cooled to room temperature and stirred under a nitrogen atmosphere overnight. An aliquot (~0.3 mL) was removed and quenched with sat. $NH_4Cl$ (~1.0 mL) and analysed by LC (upper layer from aliquot diluted with MeCN (~1 mL). The reaction was continued until the level of starting material was less than 5%. The reaction was quenched by the addition of sat. $NH_4Cl$ (138 mL) to the reaction mixture maintaining the internal temperature below 30° C. The mixture was phase separated, the aqueous phase extracted with diethyl ether (1×200 mL) and the combined organic phase dried ($MgSO_4$). The solution was concentrated in vacuo to yield a viscous oil (33.4 g). MeOH (100 mL) was added and the mixture heated to a bath temperature of 60° C., before cooling to room temperature. The solid was filtered, washed with ice cold MeOH (3×25 mL), washed with heptane (1×25 mL) and pulled dry. White solid (21 g, 68%)

TABLE 12

| Scale | Conditions | Temp (° C.) | Comments |
| --- | --- | --- | --- |
| 1.0 g | 1 eq 20-EtDHT, 1.2 eq MeMgBr 6.1vol 2-MeTHF | 60° C. | Crude material purified by column chromatography to yield two main fractions: 180 mg of impure product plus an unidentified material (140 mg) |
| 0.5 g | 1 eq 20-EtDHT, 2.6 eq MeMgBr 35vol $Et_2O$ | reflux | 0.44 g of oily gum which looks okay by $^1$H NMR. Trituration from MeOH yielded two samples: 160 mg (96%) and 150 mg (90%) |

TABLE 12-continued

| Scale | Conditions | Temp (° C.) | Comments |
|---|---|---|---|
| 0.6 g | 1 eq 20-EtDHT, 2.6 eq MeMgI 35vol Et$_2$O | reflux | 0.45 g of oily gum. Purity = 77% (by LC). Trituration yielded 110 mg of 94.1% purity. |
| 30.0 g | 1 eq 20-EtDHT 2.6 eq MeMgBr 35vol Et$_2$O | reflux | <2% SM and 81% product. After work-up and re-crystallisation from MeOH: yield 68%, 21 g, >99% purity |
| 1 g | 1 eq 20-EtDHT 2.6 eq MeMgBr 35 vol TBME | rapid. addition, then heated 45° C./4 h | After work-up and trituration with MeOH: yield 54%, 0.56 g, 96% purity |
| 1 g | 1 eq 20-EtDHT 2.6 eq MeMgBr 35 vol CPME | rapid addition, then heated 45° C./4 h | After work-up and trituration with MeOH: yield 52%, 0.54 g, 95.7% purity |
| 10 g | 1 eq 20-EtDHT 2.6 eq MeMgBr 35 vol TBME | rapid addition, then heated 35° C./4 h | After completion of MeMgBr addition: 1.2% 20-EtDHT, 85% product (HPLC). After heating, work-up and trituration with MeOH: yield 75%, 7.79 g, 96.4% purity |
| 1 g | 1 eq 20-EtDHT 2.6 eq MeMgBr 35 vol Et$_2$O | rapid addition, no heating, stirred 4 h | After completion of MeMgBr addition: 0.3% 20-EtDHT, 84% product (HPLC). After work-up and trituration with MeOH: yield 58%, 0.60 g, 94.8% purity |

Analytical Methods and in-Process-Checks

1H NMR (400 MHz) was used plus HPLC method 38XB during lab work. The reaction was monitored by LC analysis of a quenched (sat NH$_4$Cl) reaction aliquot: <2.0% 20-ethyldihydrothevinol and 71% (S)-19-propyldihydrothevinol.

For confirming purity and for LC-MS work method UFC-LC-MUN-1 was used in the analytical lab.

Analytical Results

| Appearance | HPLC (a/a %) | Comments |
|---|---|---|
| White solid | 94.1 | From MeMgI |
| White solid | >99 | Crude material had an overall purity of 81% and contained <2% starting material |

$^1$H NMR (CDCl$_3$ 400 MHz); δ=0.75 (1H, m), 0.85 (3H, t), 0.95-1.1 (6H, m), 1.3 (1H, m), 1.5-1.7 (7H, m), 1.8 (1H, t), 2.0 (1H, t, d), 2.1-2.4 (6H, m), 2.6 (1H, d), 2.7 (1H, t, d), 3.0 (1H, d), 3.5 (3H, s), 3.8 (3H, s), 4.3 (1H, s), 4.7 (1H, s), 6.5 (1H, d), 6.7 (1H, d)

$^{13}$C NMR (CDCl$_3$, 75 MHz); δ=15.12, 16.96, 18.04, 21.91, 25.55, 29.88, 31.99, 35.53, 36.05, 38.97, 43.53, 45.17, 46.19, 49.09, 50.77, 52.72, 56.93, 61.32, 80.34, 97.05, 114.21, 119.06, 128.84, 132.48, 141.63, 146.97

LC; >99%

Advantages of Optimised Process

Reaction works in a range of ethereal solvents, although diethyl ether appears to give the cleanest crude product.

Material of excellent purity is obtained following a re-crystallisation from methanol.

Stage 5: Hydrolysis

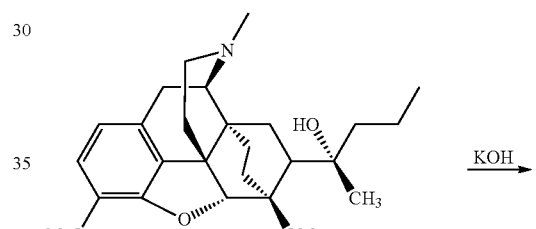

(S)-19-Propyldihydrothevinol (4)
Chemical Formula: C$_{26}$H$_{37}$NO$_4$
Molecular Weight: 427.58

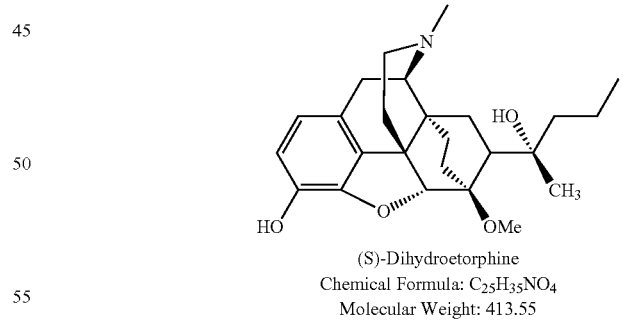

(S)-Dihydroetorphine
Chemical Formula: C$_{25}$H$_{35}$NO$_4$
Molecular Weight: 413.55

The reaction was run without significant changes (Table 13). Recrystallisation was carried out from an ethanol/water mixture then ethanol.

Procedure: (S)-DHE (10 g) was added to EtOH (60 mL) and heated at reflux until dissolved. Water (32 mL) forming a hazy solution which was allowed to cool to room temperature over ~2 hrs. The white solid was collected by filtration. (4.26 g, 42 wt % recovery). Purity 98%. Overall wt % yield=45%

TABLE 13

| Scale | Conditions | Temp (° C.) | Comments |
|---|---|---|---|
| 15 g | (S)-19 propyldihydrothevinol (1 eq), KOH (20.85 eq), diethylene glycol (16.6 vol) | 185 | Reaction heated at 185° C. for ~18 hrs with air condenser. Yield of crude 107%, purity 95% |

Analytical Methods and in-Process-Checks $^1$H NMR (400 MHz) was used plus HPLC method 38XB during lab work for IPCs. The reaction was monitored by LC analysis and quenched when no (S)-19-propyldihydrothevinol remained. The reaction was 92% complete.

For confirming purity and for LC-MS work method UFC-LC-MUN-1 was used in the analytical lab.

Analytical Results

| Appearance | HPLC (a/a %) |
|---|---|
| Tan solid | 95.0 |

$^1$NMR (CDCl$_3$, 400 MHz); δ=0.7 (1H, m), 0.8 (3H, t), 1.0-1.1 (5H, m), 1.3 (1H, m), 1.5-1.8 (6H, m), 1.85 (1H, t), 1.95 (1H, t, d), 2.1-2.3 (5H, m), 2.6 (1H, d), 2.7 (1H, t), 3.0 (1H, d), 3.5 (3H, s), 4.3 (1H, s), 4.8 (1H, s), 6.0 (1H, br), 6.4 (1H, d), 6.7 (1H, d)

$^{13}$C NMR (CDCl$_3$, 75 MHz); δ=15.10, 16.95, 18.00, 21.99, 25.37, 29.82, 31.96, 35.43, 36.15, 38.93, 43.51, 45.22, 46.50, 49.04, 52.72, 61.33, 80.42, 97.38, 116.61, 119.46, 127.92, 132.07, 137.56, 145.67

LC; 98.8%

Chiral LC; 99.44% (S)-DHE, 0.554 (R)-DHE

Advantages of Optimised Process

Significant improvement in the purity of the crude material obtained from the reaction to 95%.

Removal of the methanol trituration—material recrystallised from ethanol/water and ethanol.

Stage 6: Recrystallisation

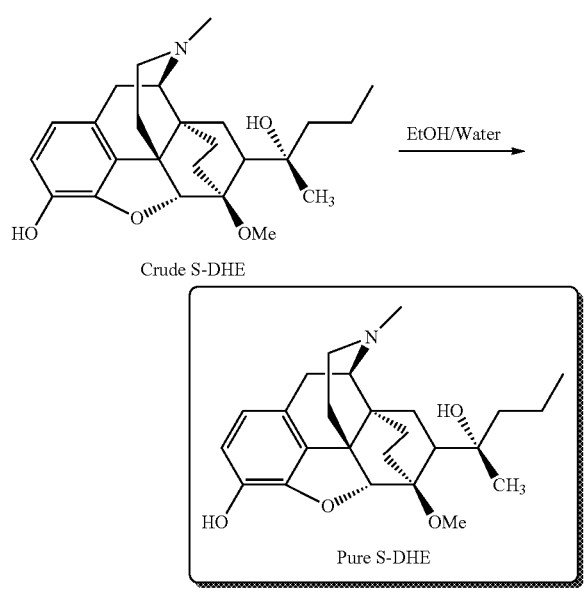

An increase in the water content to ~35% (total volume 9.2 vol) resulted in the formation of a white solid. Further recrystallisations from ethanol and ethanol/water mixtures improved the purity of the material (Table 14).

Procedure:

(1) (S)-DHE (3.0 g) was added to EtOH (10 mL) and the suspension heated at reflux producing an orange solution. The solution was allowed to cool to room temperature over 16 hrs. The resulting white solid was collected by filtration (2.1 g, 70 wt %). Purity >99%.

(2) (S)-DHE (1.8 g) was added to EtOH (7 mL) and the mixture heated at reflux until in solution. Water (2 mL) was added and the hazy solution allowed to cool to room temperature over 2 hrs. The resulting white solid was collected by filtration (1.29 g, 72 wt %).

TABLE 14

| Scale | Conditions | Temp (° C.) | Comments |
|---|---|---|---|
| 10 g | 9.2 vol of ~65/35 EtOH/water | reflux | Material heated in EtOH, then water added. White solid, 42 wt % recovery, 98% purity |
| 3.0 g | 3.3 vol (EtOH) | reflux | White solid, 70 wt % recovery, >99% purity |
| 1.8 g | 4.5 vol (20% water/ 80% EtOH) | reflux | Water added at reflux, then allowed to cool. 72 wt % recovery, >99% |

Analytical Methods and in-Process-Checks $^1$H NMR (400 MHz) was used plus HPLC method 38XB during lab work for IPCs.

For confirming purity and for LC-MS work method UFC-LC-MUN-1 was used in the analytical lab. For confirming chiral purity method UFC-LC-MUN-2 was used in the analytical lab.

Analytical Results

| Appearance | HPLC (a/a %) | Chiral % purity (HPLC) |
|---|---|---|
| White solid | >99% | 99.98 |

Advantages of Optimised Process

Recrystallisation from ethanol/water or ethanol produces material of good overall purity and <0.02% (R)-DHE.

Use of (R) and (S) Dihydroetorphine in the Treatment of Pain

Effects of (R) and (S)-Dihhydroetorphine in the Tail Flick Test of Nociception in the Rat The test model used is well known in the art and is described in J. Pharmacol Exp Ther, 1941, 72, 74-79 (D'Amour et al, A method for determining loss of pain sensation)).

The objective of this study was to assess the potential analgesic effects of R- and S-isomers of dihydroetorphine (R-DHE and S-DHE), at doses of 0.1, 0.3 and 0.5 µg/kg (R-DHE) and 3, 10 and 30 µg/kg (S-DHE), in a tail flick test designed to detect effects on nociception in rats. Morphine hydrochloride was used as a reference substance and fentanyl citrate was used as a comparator substance.

Test Substances and Materials

Test Substances, Reference Substance and Vehicle

Test substance: dihydroetorphine (R-DHE colourless liquid, used as free base) and dihydroetorphine (S-DHE liquid; used as free-base) Vehicle for test substance: Citrate buffer (citric acid monohydrate:sodium citrate:sodium chloride: water for irrigation, in the ratio, 0.03:0.10:0.86:90.01 (g:g: g:mL)) [citric acid monohydrate (white powder, Sigma, UK), sodium citrate (Sigma, UK), sodium chloride (white solid; Merck), sterile water for irrigation (clear liquid; Baxter Healthcare, UK)]

Reference substance: Morphine hydrochloride (white powder; Macfarlan Smith, Edinburgh, UK)

Comparator substance: Fentanyl citrate (white powder; Sigma, UK)

Test, Reference and Comparator Substance Storage

The test substances were stored at room temperature, protected from light, and the reference and comparator substances were stored at room temperature.

Route of Administration and Dose Levels

The route of administration of R- and S-isomer forms of DHE and the vehicle was intravenous. A possible route of administration in humans is intravenous. The doses of the R-DHE were 0.1, 0.3 and 0.5 µg/kg. The doses of the S-DHE were 3, 10 and 30 µg/kg.

The dose of morphine was 5 mg/kg. The route of administration of morphine was intravenous.

The doses of fentanyl were 0.5, 2 and 6 µg/kg. The route of administration of fentanyl was intravenous.

Animals

Species: Rat
Strain: Sprague-Dawley
Sex: Male
Number of animals: 111 animals were allocated to study; the remaining 9 animals were returned to stock
Age range: 9 to 11 weeks (based on the average body weight)
Weight range: 198 to 258 g
Acclimatisation: 6 days after delivery, before commencing the study investigation
Source: Harlan UK Ltd Animal Identification and Randomisation Each animal was arbitrarily allocated a unique identification number which appeared on the data sheets and cage cards. Animals were identified by a waterproof tail mark.

Animal Health and Welfare

All studies were conducted in accordance with the legislation under the Animals (Scientific Procedures) Act 1986, with UK Home Office Guidance on the implementation of the Act and with all applicable Codes of Practice for the care and housing of laboratory animals. The procedure adopted in this study is covered in procedure number 213N, which has a moderate severity limit.

Housing and Environment

Animals were housed in groups of up to 5 in sawdust filled solid-bottom cages. During the acclimatisation, the rooms and cages were cleaned at regular intervals to maintain hygiene. The rooms were illuminated by fluorescent lights set to give a 12 h light-dark cycle (on 07.00, off 19.00), as recommended in the Home Office Animals (Scientific Procedures) Act 1986. The rooms were air-conditioned and the air temperature and relative humidity measured. During the acclimatisation period room temperature was maintained (range 19° C. to 22° C.) and humidity levels were within the range 22% to 44%. The procedure room temperature was maintained (range 20° C. to 21° C.) and humidity levels were within the range 22% to 26%.

Diet and Water

A diet of RM1(E) SQC (Special Diets Services, Witham, UK) and mains tap water were offered ad libitum. Each batch of diet was delivered with an accompanying certificate of analysis detailing nutritional composition and levels of specified contaminants (e.g. heavy metals, aflatoxin and insecticides). The water was periodically analysed for impurities and contaminants. The criteria for acceptable levels of contaminants in stock diet and water supply were within the analytical specifications established by the diet manufacturer and water analytical service, respectively.

Health Status

The animals were examined on arrival and prior to the study; all animals were healthy and considered suitable for experimental use.

Experimental Design

Formulation of the Test, Reference, and Comparator Substances

The citrate buffer was prepared by accurately weighing the appropriate quantities of each component and dissolving them in sterile water for irrigation. When the components were fully dissolved the osmolality and pH of the solution were measured. The vehicle was deemed acceptable as the pH was 5.01, which was within the range pH 4.8 to 5.2 and the osmolality was 296 mOsmol/kg, between the range of 280 to 300 mOsmol/kg. The vehicle was then terminally filtered through a Millex GV stericup under aseptic conditions and stored at 2° C. to 8° C. prior to use.

The test substances, DHE (R- and S-isomers), were formulated for dosing as solutions in citrate buffer. The desired concentrations (0.02, 0.06 and 0.10 µg/mL for the R-DHE, and 0.6, 2 and 6 µg/mL for the S-DHE) for dosing were achieved by serial dilution of the appropriate stock solutions which were provided at an approximate concentration of 20 µg/mL. Stock solutions were passed through a Millex GV 0.22 µm Durapore sterile filter unit into glass vials and each subsequent dilution with the sterile citrate buffer was performed by sterile manipulation. Formulations were prepared within the known stability period for (R) DHE and stored refrigerated, at approximately 4° C., until required for dosing.

The reference substance, morphine hydrochloride, was formulated for dosing by dissolving a known amount in citrate buffer to give a 1 mg/mL solution. A correction factor of 1.32 was applied to enable the dose of morphine to be expressed in terms of free-base. Solutions were freshly prepared and protected from light.

The comparator substance, fentanyl citrate, was formulated for dosing by dissolving a known amount in citrate buffer to give a stock solution concentration of 0.36 mg/mL. This stock solution was then serially diluted with citrate buffer to give the final concentrations of 0.1, 0.4 and 1.2 µg/mL. A correction factor of 1.57 was applied to enable the dose of fentanyl to be expressed in terms of free-base. Solutions were freshly prepared and protected from light Group Sizes, Doses and Identification Numbers There were 11 treatment groups, with up to 10 rats per group. Each treatment group was given a letter (A to K). The rats were randomly allocated to treatment groups on the day prior to dosing based on the pre-dose baseline values for the tail flick test (see below).

| D | Vehicle | 5 mL/kg |
| F | R-DHE | 0.1 µg/kg |
| E | R-DHE | 0.3 µg/kg |
| K | R-DHE | 0.5 µg/kg |
| I | S-DHE | 3 µg/kg |
| H | S-DHE | 10 µg/kg |
| G | S-DHE | 30 µg/kg |
| J | Fentanyl | 0.5 µg/kg |
| C | Fentanyl | 2 µg/kg |
| B | Fentanyl | 6 µg/kg |
| A | Morphine | 5 mg/kg |

The vehicle was citrate buffer. The animals were dosed intravenously into a tail vein using a dose volume of 5 mL/kg and a polypropylene syringe with a Becton Dickinson 25G (0.5×16 mm) needle. The total volume of 5 mL/kg was delivered at as constant a rate as possible over a 2 min±10 s interval. The start and stop time for the slow bolus were recorded. The time of dosing was recorded in the raw data.

Treatment Blinding

Dosing solutions were encoded (A to K) so that the observer did not know the identity of the treatment groups.

Body Weights

Animals were weighed prior to testing and body weights recorded on the same day as the administration of substances.

Procedure

1. Acclimatisation

On one occasion prior to behavioural testing, each animal was subjected to routine handling and acclimatisation to the behavioural testing environment.

2. Baseline Behavioural Testing

The rats were moved to the procedure room 1 day prior to the experiment. The rats were then housed, dosed and observed in the procedure room. The tail flick test (see below) was performed on all rats on 3 separate occasions prior to dosing, to establish baseline values. Pre-dose baseline values were taken as the final test reading (the data from the first and second tests were not included but classed as part of the acclimatisation).

Tail flick test: Each rat was lightly held on the surface of the tail flick apparatus (Ugo Basile, Italy), so that its tail was positioned directly over the infrared source. The infrared source was then applied to a small area on the ventral surface of the tail. Activation of the infrared source simultaneously activated a timer, which automatically registered the time taken to deflect (withdraw or flick) the tail. The tail flick latency was noted for each animal. The infrared intensity was set at IR50 and the maximum length of exposure to the IR source was 10 s. Non-responding animals were therefore allocated a withdrawal latency of 10 s.

3. Group Allocation and Exclusion Criteria

Animals were randomly allocated to the treatment groups (A to K) on the day prior to dosing, based on the pre-dose baseline values for the tail flick test.

4. Dosing and Behavioural Testing

The animals were not fasted for this study. Tail flick tests were performed approximately 5, 10, 20, 30, 60 and 120 min post-dose (with respect to the start of dosing), to investigate treatment effect.

5. Terminations

Any animal not allocated to a treatment group was terminated by cervical dislocation at the end of the study. The remaining animals were returned to stock on conclusion of the final testing period.

Statistical Analysis

Statistical comparisons were made between DHE (R- and S-isomers), morphine, fentanyl groups with the vehicle group using parametric or non-parametric statistical procedures. The choice of parametric (one-way analysis of variance (ANOVA), Dunnett's t-test) or non-parametric (Kruskal-Wallis statistic, Dunn's test and Mann-Whitney U-test) statistical procedures was based on whether the groups to be compared satisfied the homogeneity of variance criterion (evaluated by the Levene Mean test of F-test). Statistical significance was assumed when $P<0.05$.

In addition, the data were converted to % MPE (Maximum Possible Effect), defined as 100×(test−control)/(cut-off−control) where 'control' was the vehicle group observation, 'test' was the post-dose observation and 'cut-off' was the maximum duration of the stimulus allowed (10 s for tail flick). Dose-response curves for each isomer of DHE (R- and S-isomers) and fentanyl were generated for the first 4 observation time points and the $ED_{50}$ (50% MPE dose) was calculataed. Analysis was performed on the $log_{10}$ (dose× $10^3$), using a nonlinear regression (line of best fit), sigmoidal dose-response. As post-dose data had returned to baseline at the 60 and 120 min time points, no calculations were required on these data.

Results

Figure 11:
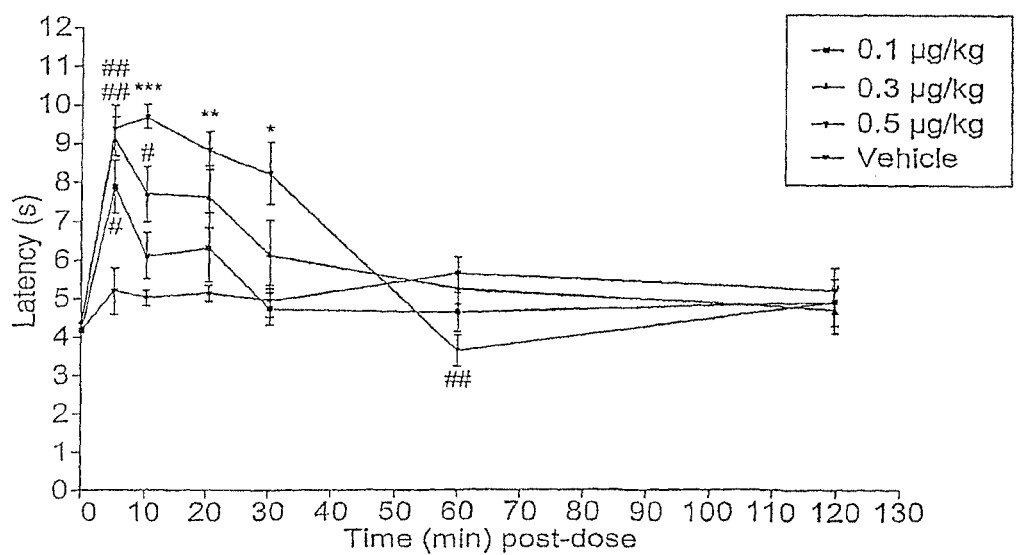
FIGS. 11 to 13 show time-course curves following intraveneous administration of (R)- or (S)-DHE or a reference or comparator substance.
Figure 12:
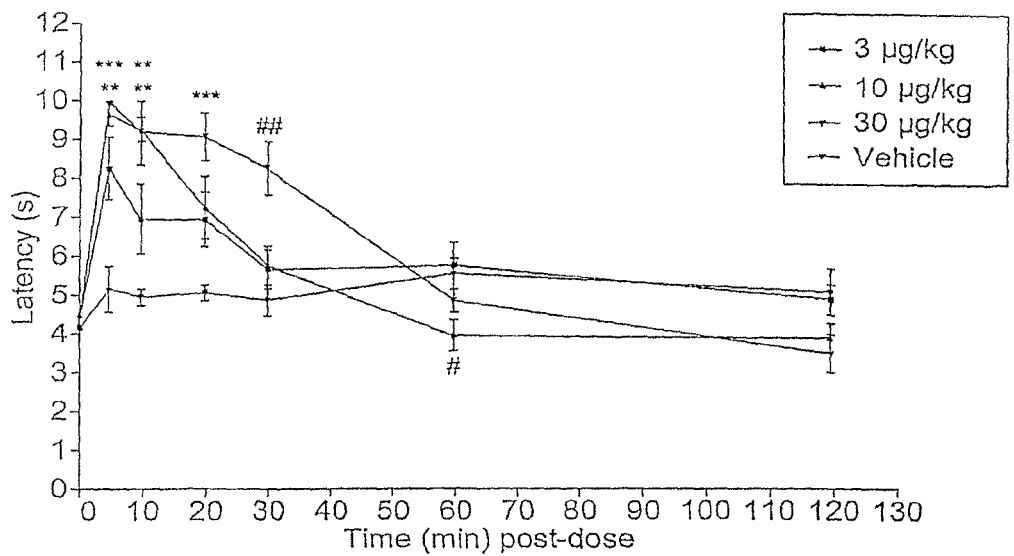

The group mean±s.e. mean data for tail flick withdrawal latency are summarised in Table 15. The $ED_{50}$ values calculated for R-DHE, S-DHE and fentanyl were compared to estimate their relative potencies (Table 11). Time-course graph plots are presented in FIG. 11 to FIG. 13 and $ED_{50}$ (50% MPE dose) dose response curves and data are presented in FIG. 14 to FIG. 17.

TABLE 15

Effects of Dihydroetorphine (R- and S-isomers), fentanyl and morphine on tail flick withdrawal latency in rats

| Treatment | Pre-dose | Tail flick latency (s) at time (min) post-dose | | | | | |
|---|---|---|---|---|---|---|---|
| | | 5 | 10 | 20 | 30 | 60 | 120 |
| Vehicle 5 mL/kg i.v. | 4.2 ± 0.3 | 5.2 ± 0.6 | 5.0 ± 0.2 | 5.1 ± 0.2 | 4.9 ± 0.4 | 5.6 ± 0.4 | 5.1 ± 0.6 (9) |
| DHE (R-isomer) 0.1 µg/kg i.v. | 4.2 ± 0.3 | 7.9 ± 0.7* | 6.1 ± 0.6 | 6.3 ± 0.9 | 4.7 ± 0.4 | 4.6 ± 0.5 | 4.8 ± 0.3 |
| DHE (R-isomer) 0.3 µg/kg i.v. | 4.2 ± 0.3 | 9.2 ± 0.5** | 7.7 ± 0.7$ | 7.6 ± 0.8 | 6.1 ± 0.9 | 5.2 ± 0.4 | 4.6 ± 0.6 |
| DHE (R-isomer) 0.5 µg/kg i.v. | 4.4 ± 0.3 | 9.4 ± 0.6** | 9.7 ± 0.3$$$ | 8.8 ± 0.5$$ | 8.2 ± 0.8$ | 3.6 ± 0.4** | 4.8 ± 0.6 (8) |
| DHE (S-isomer) 3 µg/kg i.v. | 4.2 ± 0.3 | 8.3 ± 0.8 | 7.0 ± 0.9 | 7.0 ± 0.7 | 5.7 ± 0.5 | 5.8 ± 0.6 | 4.9 ± 0.4 (9) |
| DHE (S-isomer) 10 µg/kg i.v. | 4.2 ± 0.3 | 9.7 ± 0.3$$ | 9.3 ± 0.3$$ | 7.3 ± 0.8 | 5.8 ± 0.5 | 4.0 ± 0.4* | 3.9 ± 0.4 |
| DHE (S-isomer) 30 µg/kg i.v. | 4.2 ± 0.3 | 10.0 ± 0.0$$$ | 9.2 ± 0.8$$ | 9.1 ± 0.6$$$ | 8.3 ± 0.7** | 4.9 ± 0.3 | 3.5 ± 0.5 (8) |
| Fentanyl 0.5 µg/kg i.v. | 4.2 ± 0.3 | 5.8 ± 0.6 | 5.3 ± 0.6 | 5.2 ± 0.6 | 4.6 ± 0.4 | 4.8 ± 0.4 | 4.6 ± 0.4 (9) |
| Fentanyl 2 µg/kg i.v. | 4.2 ± 0.3 | 9.0 ± 0.7$$ | 9.1 ± 0.4$$$ | 7.5 ± 0.9 | 7.1 ± 0.7 | 4.9 ± 0.7 | 4.2 ± 0.8 |

TABLE 15-continued

Effects of Dihydroetorphine (R- and S-isomers), fentanyl and morphine on tail flick withdrawal latency in rats

| Treatment | Pre-dose | Tail flick latency (s) at time (min) post-dose | | | | | |
|---|---|---|---|---|---|---|---|
| | | 5 | 10 | 20 | 30 | 60 | 120 |
| Fentanyl 6 µg/kg i.v. | 4.2 ± 0.3 | 10.0 ± 0.0$^{\$\$\$}$ | 8.4 ± 0.7$^{\$\$}$ | 8.1 ± 0.7$^{\$}$ | 6.5 ± 1.0 | 6.0 ± 1.0 | 6.3 ± 0.7 |
| Morphine 5 µg/kg i.v. | 4.2 ± 0.3 | 10.0 ± 0.0$^{\#\#\#}$ | 10.0 ± 0.0$^{\#\#\#}$ | 10.0 ± 0.0$^{\#\#\#}$ | 10.0 ± 0.0$^{\#\#\#}$ | 8.7 ± 0.9$^{\#}$ | 6.2 ± 0.9 (8) |

Vehicle was citrate buffer [citric acid monohydrate:sodium citrate:sodium chloride:water for irrigation in the ration 0.03:0.10:0.86:99.01 (g:g:g:mL)]
Data are expressed as mean ± SEM.
N = 10 animals per group, unless otherwise stated in parenthesis.
*P < 0.05 and
**P < 0.01 when compared to vehicle (ANOVA) and Dunnett's t-test).
$^{\$}$P < 0.05,
$^{\$\$}$P < 0.01 and
$^{\$\$\$}$P < 0.001 when compared to vehicle (Kruskal-Wallis and Dunn's test).
$^{\#}$P < 0.05 and
$^{\#\#\#}$P < 0.001 when compared to vehicle (Mann-Whitney U-test).

Effects of Dihydroetorphine (R-Dhe) on Tail Flick Withdrawal Latency (FIG. 11) Intravenous administration of R-DHE at a dose of 0.1 µg/kg caused a significant increase in the tail flick latency at 5 min post-dose (7.9±0.7 s; P<0.05; ANOVA and Dunnett's t-test) when compared to vehicle group data (5.2±0.6 s). Intravenous administration of R-DHE at 0.3 µg/kg caused a significant increase in the tail flick withdrawal latency at 5 and 10 min post-dose (9.2±0.5 s; P<0.01; ANOVA and Dunnett's t-test; 7.7±0.7 s; P<0.05; Kruskal-Wallis and Dunn's test, respectively) when compared to vehicle group data (5.2±0.6 and 5.0±0.2 s, respectively) but had no effect at any other time points. Intravenous administration of R-DHE at a dose of 0.5 µg/kg caused a significant increase in the tail flick withdrawal latency at 5, 10, 20 and 30 min post-dose (9.4±0.6 s; P<0.01; ANOVA and Dunnett's t-test; 9.7±0.3 s; P<0.001; 8.8±0.5 s P<0.01; 8.2±0.8 s; P<0.05; all Kruskal-Wallis and Dunn's test, respectively) when compared to vehicle group data (5.2±0.6, 5.0±0.2, 5.1±0.2 and 4.9±0.4 s, respectively). A significant decrease observed in the tail flick latency at 60 min post-dose in the 0.5 µg/kg group is not considered to be pharmacologically relevant. No effect was noted at 120 min post-dose. These data indicate an immediate analgesic onset, with peak effects at approximately 5 and 10 min post-dose, returning to baseline values (comparable to the vehicle control) by the 60 min post-dose time point.

The estimated $ED_{50}$ of R-DHE, i.e. the 50% MPE, was 0.08, 0.23, 0.25 and 0.42 µg/kg at 5, 10, 20 and 30 min post-dose, respectively. There was no dose response at the 60 and 120 min post-dose time points.

Effects of Dihydroetorphine (S-DHE) on tail flick withdrawal latency (FIG. 12) Intravenous administration of S-DHE at a dose of 3 µg/kg did not significantly affect tail flick withdrawal latency at any time point tested when compared to vehicle group data. Intravenous administration of S-DHE at 10 µg/kg caused a significant increase in the tail flick withdrawal latency at 5 and 10 min post-dose (9.7±0.3 and 9.3±0.3 s respectively; both P<0.01; Kruskal-Wallis and Dunn's test) when compared to vehicle group data (5.2±0.6 and 5.0±0.2 s, respectively). A significant decrease observed in the tail flick withdrawal latency at 60 min post-dose was not considered to be pharmacologically relevant. Intravenous administration of S-DHE at a dose of 30 µg/kg caused a significant increase in the tail flick withdrawal latency at 5, 10, 20 and 30 min post-dose (10.0±0.0 s; P<0.001; 9.2±0.8 s; P<0.01; 9.1±0.6 s; P<0.001; Kruskal-Wallis and Dunn's test and 8.3±0.7 s; P<0.01; ANOVA and Dunnett's t-test; respectively) when compared to vehicle group data (5.2±0.6, 5.0±0.2, 5.1±0.2 and 4.9±0.4 s, respectively). These data indicate an immediate analgesic onset with peak effects at the 5 min post-dose time point, returning to baseline values (comparable to the vehicle control) by the 60 min post-dose time point.

The estimated $ED_{50}$ of DHE (S-isomer), i.e. the 50% MPE, was 2.17, 3.80, 7.52 and 20.95 µg/kg at 5, 10, 20 and 30 min post-dose, respectively. There was no dose response at the 60 and 120 min post-dose time points.

Figure 13:
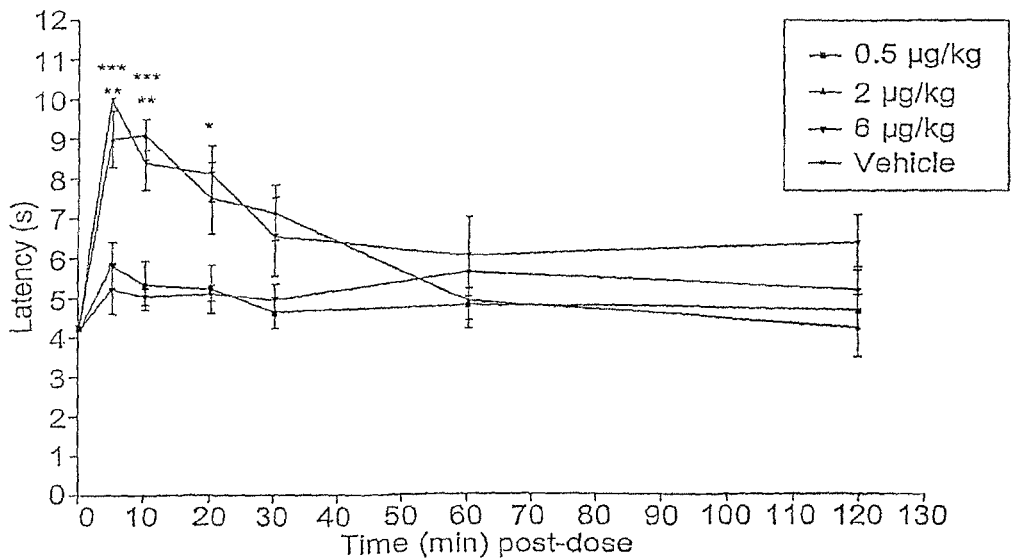
Figure 14:
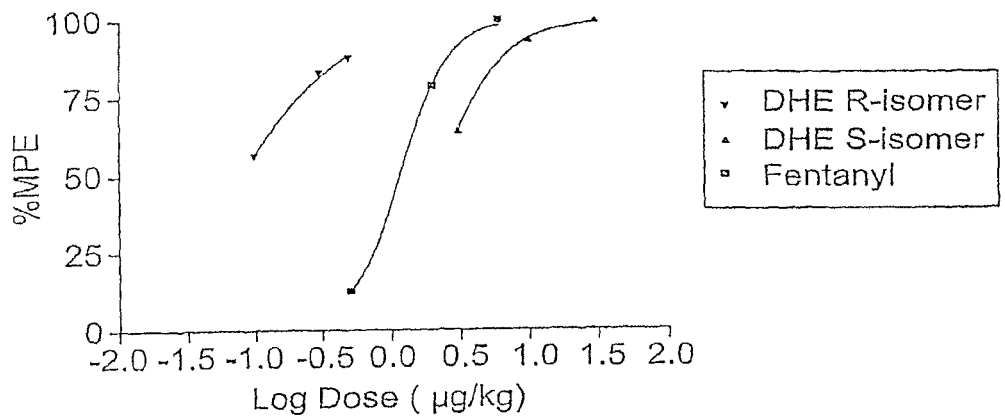
FIGS. 14 to 17 show dose response curves following intravenous administration of (R)-DHE, (S)-DHE or a reference or comparator substance.
Figure 15:
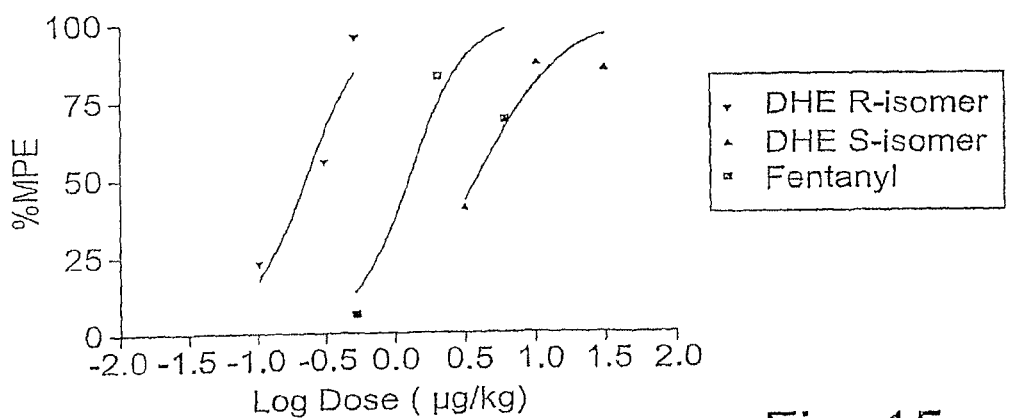
Figure 16:
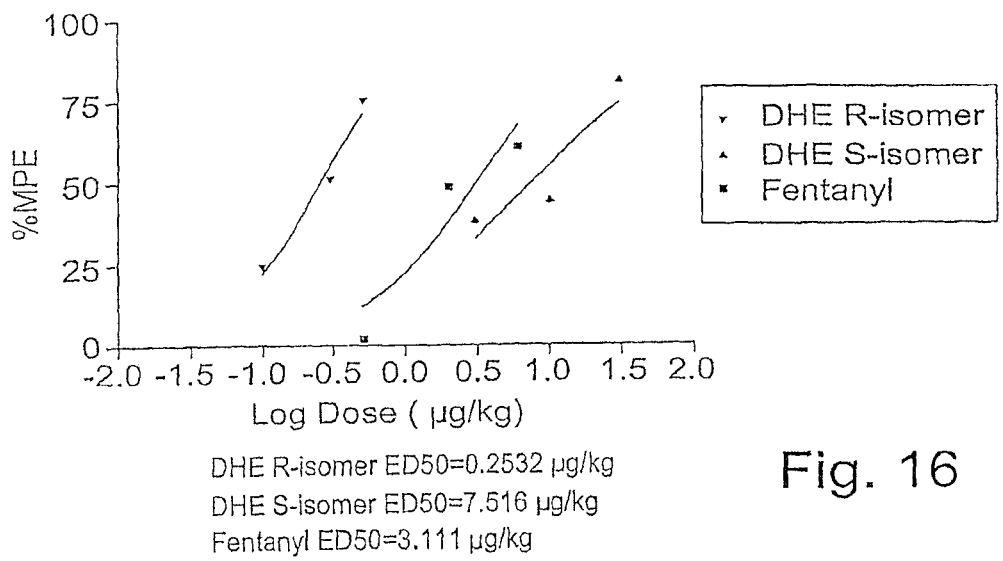
Figure 17:
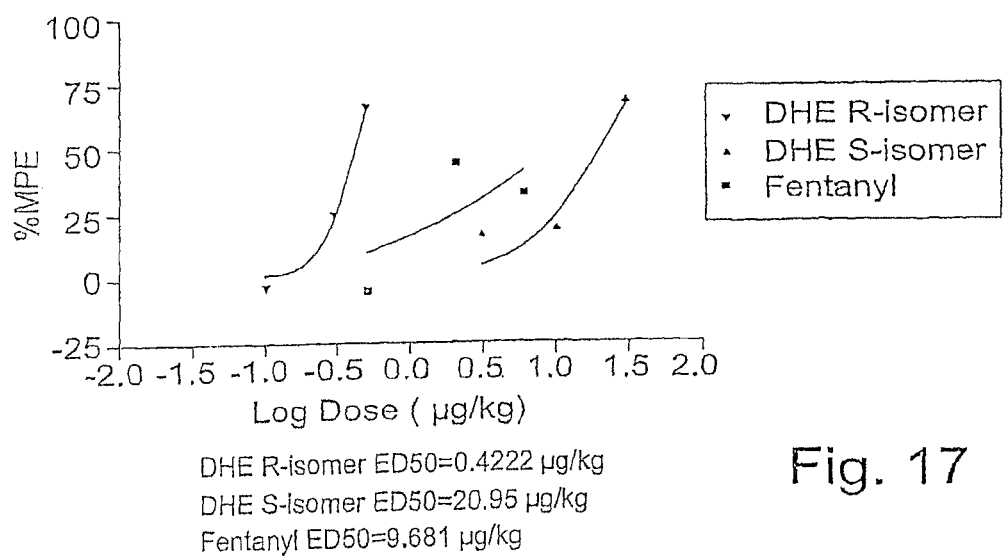

Effects of Fentanyl on Tail Flick Withdrawal Latency (FIG. 13)

Intravenous administration of fentanyl at a dose of 0.5 µg/kg did not significantly affect tail flick withdrawal latency at any time point tested when compared to vehicle group data. Intravenous administration of fentanyl at 2 µg/kg resulted in a significant increase in the tail flick withdrawal latency at 5 and 10 min post-dose (9.0±0.7 s; P<0.01 and 9.1±0.4 s; P<0.001, respectively; both Kruskal-Wallis and Dunn's test) when compared to vehicle group data (5.2±0.6 and 5.0±0.2 s, respectively). Intravenous administration of fentanyl at a dose of 6 µg/kg caused a significant increase in the tail flick withdrawal latency at 5, 10 and 20 min post-dose (10.0±0.0 s; P<0.001; 8.4±0.7 s; P<0.01; 8.1±0.7 s; P<0.05, respectively; all Kruskal-Wallis and Dunn's test) when compared to vehicle group data (5.2±0.6, 5.0±0.2 and 5.1±0.2 s, respectively). These data indicate an immediate analgesic onset with peak effects at the 5 min time point, returning to baseline values (comparable to the vehicle control) by the 60 min post-dose time point.

The estimated $ED_{50}$ of fentanyl, i.e. the 50% MPE, was 1.14, 1.25, 3.11 and 9.68 µg/kg at 5, 10, 20 and 30 min post-dose, respectively. There was no dose response at 60 and 120 min post-dose time points.

Comparative Effects of R-DHE, S-DHE and Fentanyl

The $ED_{50}$ values calculated for R-DHE, S-DHE and fentanyl were compared to estimate their relative potencies (Table 16). The data suggest that during the first 30 min, after a single intravenous administration of each compound in the male rat, R-DHE had an analgesic potency that is 5- to 23-fold that for fentanyl, S-DHE had an analgesic potency of 0.3- to 0.5-fold that of fentanyl, and that R-DHE has an analgesic potency that is 17- to 50-fold that for S-DHE.

TABLE 16

ED$_{50}$ values and comparative ratios of R-DHE, S-DHE and fentanyl

| Time Post-dose (min) | ED$_{50}$ R-DHE (µg/kg) | ED$_{50}$ S-DHE (µg/kg) | ED$_{50}$ fentanyl (µg/kg) | ED$_{50}$ ratio fentanyl/R-DHE | ED$_{50}$ ratio fentanyl/S-DHE | ED$_{50}$ ratio fentanyl/S-DHE/R-DHE |
|---|---|---|---|---|---|---|
| 5 | 0.08 | 2.17 | 1.14 | 14 | 0.5 | 28 |
| 10 | 0.23 | 3.80 | 1.24 | 5 | 0.3 | 17 |
| 20 | 0.25 | 7.52 | 3.11 | 12 | 0.4 | 30 |
| 30 | 0.42 | 20.95 | 9.68 | 23 | 0.5 | 50 |

Effects of Morphine on Tail Flick Withdrawal Latency

Intravenous administration of morphine (5 mg/kg) caused a significant increase in the tail flick withdrawal latency at 5, 10, 20, 30 (10.0±0.0 s; P<0.001; Mann-Whitney U-test, for all 4 time points) and 60 min post-dose (8.7±0.9 s; P<0.05; Mann-Whitney U-test) when compared to vehicle group data (5.2±0.6, 5.0±0.2, 5.1±0.2, 4.9±0.4 and 5.6±0.4 s, respectively).

Conclusion

A single intravenous administration of R-DHE at doses of 0.1, 0.3 and 0.5 µg/kg and S-DHE at doses of 10 and 30 µg/kg caused a significant dose-dependent increase in the tail flick withdrawal latency of male rats up to 30 min post-dose. Intravenous administration of fentanyl at doses of 2 and 6 µg/kg caused a significant dose-dependent increase in tail flick withdrawal latency up to 30 min post-dose.

The ED$_{50}$ values calculated for R-DHE, S-DHE and fentanyl were compared to estimate their relative potencies (Table 16). The data suggest that during the first 30 min after a single intravenous administration of each compound in the male rat that; R-DHE had an analgesic potency that is 5- to 23-fold that for fentanyl, S-DHE had an analgesic potency of 0.3- to 0.5-fold that of fentanyl, and that R-DHE has an analgesic potency that is 17- to 50-fold that for S-DHE.

The duration of opioid analgesic activity of R-DHE and S-DHE following intravenous administration highlights the potential benefit and therapeutic potential of these compounds in the treatment of acute pain.

The effects noted following administration of morphine are consistent with its known pharmacological activity and thus this test system was sensitive to detect nociceptive effects.

Effects of (R) and (S)-Dihydroetorphine in the Spinal Nerve Ligation Model of Neuropathic Pain The test model used is well known in the art and is described in Pain 1992; 50: 355-363 (Kim S H, Chung J M., An experimental model for peripheral neuropathy produced by segmental spinal nerve ligation in the rat).

The potential analgesic effects of dihydroetorphine following a single intravenous dose of 0.1, 0.3 and 0.5 µg/kg (R isomer) and a single intravenous dose of 3, 10 and 30 µg/kg (S-isomer) in the spinal nerve ligation model of neuropathic pain was investigated. A peripheral mononeuropathy was induced in the left hind limb of rats by tight ligation of the L5 and L6 spinal nerves. The development of mechanical allodynia and thermal hyperalgesia was monitored using established behavioural tests (Von Frey test and the Hargreaves Plantar test respectively). Morphine was used as a reference substance and Pregabalin was used as a comparator substance.

Test Substances and Materials

Test Substances, Reference Substance, Comparator Substance and Vehicles

Test Substances: Dihydroetorphine (R-Isomer) and Dihydroetorphine (S-Isomer) Vehicle for Test and Reference Substances:

Citrate buffer (citric acid monohydrate:sodium citrate: sodium chloride:sterile water, in the ratio 0.03:0.10:0.86: 99.01 (g:g:g:mL); [citric acid monohydrate (white powder; Sigma, UK), sodium citrate (Sigma, UK), sodium chloride (white solid; Merck), sterile water (clear liquid; Baxter Healthcare, UK)]

Reference substance: Morphine hydrochloride (white powder; Macfarlan Smith, Edinburgh, UK)

Comparator substance: Pregabalin (Trade name Lyrica®; white capsules; manufactured by Pfizer and supplied by Lindsay & Gilmour Chemist, Juniper Green, Edinburgh)

Vehicle for comparator substance: 1% w/v Carboxy methylcellulose (CMC, powder; Sigma, UK)

Test Reference and Comparator Substance Storage

The test substances were stored at room temperature, protected from light and the reference and comparator substances were stored at room temperature.

Route of Administration and Dose Levels

The route of administration of R- and S-isomer forms of dihydroetorphine and the vehicle (citrate buffer) was intravenous. This is a potential route of administration in humans. The doses of R-DHE were 0.1, 0.3 and 0.5 µg/kg and the doses of S-DHE were 3, 10 and 30 µg/kg.

The route of administration of morphine was intravenous. The dose of morphine was 5 mg/kg.

The route of administration of the comparator substance Pregabalin was oral. In Phase 2 of the study, the dose of Pregabalin, was 30 mg/kg. For Phase 3, the dose levels of the comparator substance, Pregabalin, were 30, 50 and 100 mg/kg.

Animals

Species: Rat
Strain: Sprague-Dawley
Sex: Male
Number of animals: 75 animals were surgically prepared.
Age range: 6 to 7 weeks (for surgery); 8 to 9 weeks (dosing Phase 1); 9 to 10 weeks (dosing Phase 2); 11 to 12 weeks (dosing Phase 3).
Weight range: 139 to 183 g (for surgery); 190 to 257 g (dosing Phase 1); 210 to 284 g (dosing Phase 2); 243 to 341 g (dosing Phase 3).
Acclimatisation: 3 days after delivery, before commencing the behavioural testing
Source: Harlan UK Ltd Animal Identification and Randomisation Each animal was arbitrarily allocated a unique identification number which appeared on the data sheets and cage cards. Animals were identified by a waterproof tail mark.

Animal Health and Welfare

All studies were conducted in accordance with the legislation under the Animals (Scientific Procedures) Act 1986, with UK Home Office Guidance on the implementation of the Act and with all applicable Codes of Practice for the care and housing of laboratory animals.

Housing and Environment

Animals were housed in groups of up to 5 in sawdust filled solid-bottom cages. During the acclimatisation, the rooms and cages were cleaned at regular intervals to maintain hygiene. The rooms were illuminated by fluorescent lights set to give a 12 h light-dark cycle (on 07.00, off 19.00), as recommended in the Home Office Animals (Scientific Procedures) Act 1986. The rooms were air-conditioned and the air temperature and relative humidity measured. During the acclimatisation period room temperature was maintained (range 20° C. to 22° C.) and humidity levels were within the range 46% to 59%. The procedure room temperature was maintained (range 19° C. to 22° C.) and humidity levels were within the range 26% to 43%.

Diet and Water

An expanded rodent diet of RM1(E) SQC (Special Diets Services, Witham, UK) and mains tap water were offered ad libitum. Each batch of diet was delivered with an accompanying certificate of analysis (C of A) detailing nutritional composition and levels of specified contaminants (e.g. heavy metals, aflatoxin and insecticides). The water was periodically analysed for impurities and contaminants. The criteria for acceptable levels of contaminants in stock diet and water supply were within the analytical specifications established by the diet manufacturer and water analytical service, respectively.

Health Status

The animals were examined on arrival and prior to the study; all animals were healthy and considered suitable for experimental use.

Experimental Design

Formulation of the test, reference and comparator substances

The citrate buffer was prepared by accurately weighing the appropriate quantities of each component and dissolving them in sterile water for injection. When the components were fully dissolved the osmolality and pH of the solution was measured. The vehicle was deemed acceptable as the pH was 5.03, which was within the range 4.8 to 5.2, and the osmolality was 295 mOsmol/kg between the range of 280 to 300 mOsmol/kg. The vehicle was then terminally filtered through a Millex GV stericup (0.22 µm filter) under aseptic conditions and stored at 2° C. to 8° C. prior to use.

The test substances, dihydroetorphine (R- and S-isomers), were formulated for dosing as solutions in citrate buffer. The desired concentrations (0.02, 0.06 and 0.10 µg/mL for the R isomer and 0.6, 2 and 6 µg/mL for the S-isomer) for dosing were achieved by serial dilution of the appropriate stock solutions which were provided at an approximate concentration of 20 µg/mL. The actual concentration of the stock solutions was noted in the raw data. Prior to serial dilution, stock solutions were passed through a Millex GV 0.22 µm Durapore sterile filter unit into glass vials and each subsequent dilution with the sterile citrate buffer was performed by sterile manipulation. No correction factor was applied and formulations were prepared as the free base. Formulations were prepared in advance of the study dosing dates and were used (1-2 days following preparation) within the known stability for R-DHE which was 11 days. S-DHE was used 1-2 days following preparation. Dosing solutions of dihydroetorphine (R- and S-isomers) were stored refrigerated, at approximately 4° C., until they were required for dosing.

The reference substance, morphine hydrochloride, was formulated for dosing by dissolving a known amount in citrate buffer to give a 1 mg/mL solution. A correction factor of 1.32 was applied to enable the dose of morphine to be expressed in terms of free base. Solutions were freshly prepared and protected from light.

The comparator substance, Pregabalin, was formulated for dosing by suspending a known amount in 1% w/v CMC to give a 3 mg/mL suspension for Phase 2 and 3, 5 and 10 mg/mL suspensions were prepared for Phase 3. No correction factor was required therefore the Pregabalin was dosed as a free-base. Suspensions were freshly prepared and protected from light.

Group Sizes, Doses and Identification Numbers

There were 5 treatment groups, with a maximum of 10 rats per group. Each treatment group was given a letter (Phase 1: A to E, Phase 2: F to J and Phase 3: K to O). The rats were randomly allocated to treatment groups on the day prior to dosing based on the pre dose baseline values for the thermal hyperalgesia test (see below).

Phase 1:

| C | Vehicle | 5 mL/kg, i.v. |
| B | R-DHE | 0.1 µg/kg, i.v. |
| A | R-DHE | 0.3 µg/kg, i.v. |
| E | R-DHE | 0.5 µg/kg, i.v. |
| D | Morphine | 5 mg/kg, i.v. |

Phase 2:

| I | Vehicle | 5 mL/kg, i.v. |
| F | S-DHE | 3 µg/kg, i.v. |
| G | S-DHE | 10 µg/kg, i.v. |
| J | S-DHE | 30 µg/kg, i.v. |
| H | Pregabalin | 30 mg/kg, p.o. |

Phase 3:

| N | Vehicle | 10 mL/kg, p.o. |
| M | Pregabalin | 30 mg/kg, p.o. |
| L | Pregabalin | 50 mg/kg, p.o. |
| K | Pregabalin | 100 mg/kg, p.o. |
| O | Morphine | 5 mg/kg, i.v. |

The intravenous vehicle, citrate buffer, was used for Phases 1 and 2 and the oral vehicle, 1% w/v CMC, was used for Phase 3. Animals allocated to intravenous treatment groups were dosed into a tail vein using a dose volume of 5 mL/kg and a polypropylene syringe with a Becton Dickinson 25G (0.5×16 mm) needle. The total intravenous volume of 5 mL/kg was delivered at as constant a rate as possible over a 2 min±10 s interval. The start and stop time for the slow intravenous bolus was recorded. Animals allocated to oral treatment groups were dosed by oral gavage, using a dose volume of 10 mL/kg. The time of dosing was recorded in the raw data.

Treatment Blinding

Dosing solutions were encoded (Phase 1: A to E, Phase 2: F to J and Phase 3: K to O) so that the observers were not aware of the identity of the treatment groups. As the comparator substance in Phase 2 of the study was administered by a different dose route, this group was not blinded to the person performing the dosing and was encoded H. Also, as the morphine control in Phase 3 was adminstered intravenously, and this was a different route to the vehicle and comparator substance groups (oral dosing), the morphine group was not blinded, and was therefore encoded O.

Body Weights

Animals were weighed prior to surgery, on Day 1 post-operatively (PO), and on each day of dosing prior to administration of substances, and body weights were recorded.

Daily Observations

General observations were made on all animals on a daily basis from Day 0 PO onwards, with particular attention being paid to the condition of the animal's left and right hind paws.

Procedure

1 Acclimatisation

Prior to behavioural testing, the animals were subjected to routine handling and acclimatisation to the behavioural testing environment.

2 Baseline Behavioural Testing

The rats were moved to the procedure room 1 day prior to the experiment. The rats were then housed, dosed and observed in the procedure room. The behavioural tests (see below) were performed on all rats on 2 separate occasions prior to surgery, to establish baseline values. Pre-surgery baseline values were taken as the data from the final (second) day of testing (the data from the first day of testing was classified as part of the acclimatisation). The sequence of tests was mechanical allodynia followed by thermal hyperalgesia, with a minimum 5 min period allowed between the tests. Mechanical allodynia (Von Frey test): Each animal was placed in a wire mesh cage and a series of Von Frey filaments applied to the plantar surface of the hind paw, from below. The filaments were applied in ascending order (starting with the weakest force), and the withdrawal threshold for both the left and right hind paws was evaluated. Each filament was indented on the mid-plantar surface of the foot to the point where it just started to bend; this was repeated approximately 8 to 10 times per filament at a frequency of approximately 1 Hz. The withdrawal threshold was defined as being the lowest force of two or more consecutive Von Frey filaments to elicit a reflex withdrawal response (i.e. a brief paw flick).

Thermal hyperalgesia (Hargreaves Plantar test): Each rat was placed in a clear plastic chamber with a glass floor and allowed a short period to acclimatise to their environment prior to testing (approximately 1 min). The animals were then challenged with a radiant infrared (IR) heat source, directed at the plantar surface of their hind paw from below, and the withdrawal latency calculated for both the left and right hind paws. The infrared intensity was set at IR50 (setting designed to deliver a heat flux reading of 250 mW $cm^3$) and the maximum length of exposure to the IR source was 18 s. Non responding animals were therefore allocated a withdrawal latency of 18 s.

3 Surgical Procedure

The animals were surgically prepared over 3 days. Each rat was anaesthetised as necessary with isofluorane in 1% to 3% oxygen. Each rat was placed in a prone position and the surface around the incision site was shaved and sterlised with surgical spirit. Under aseptic conditions, the left paraspinal muscles were separated from the spinous processes at L4 S2 levels. The L6 transverse process was then carefully removed with a small rongeur and the L4 L6 spinal nerves identified. The left L5 and L6 spinal nerves were isolated, and tightly ligated using 6-0 silk thread (as viewed under ×40 magnification). The overlying muscle and skin were closed in layers using appropriate suture material, and once complete, the anaesthesia was discontinued. On recovery from anaesthesia, rats were re-housed with their cage-mates, initially on soft padded bedding overnight to reduce the risk of infection, and subsequently on sawdust bedding following full recovery. The animals were allowed to recover for a minimum of 4 days before the behavioural testing was recommenced.

4 Developmental Testing

Following surgery, behavioural testing was conducted twice prior to the dosing day, to monitor the development of allodynia/hyperalgesia. Additional discretionary testing days were also included to ensure that a sufficient number of animals had developed allodynia/hyperalgesia prior to each dosing phase.

5 Group Allocation and Exclusion Criteria

Animals were randomly allocated to the treatment groups on the day prior to dosing based on the pre dose baseline values for the thermal hyperalgesia test. Only animals which developed both mechanical allodynia and thermal hyperalgesia were included in the study. Animals were deemed to have developed mechanical allodynia if their left paw withdrawal threshold to Von Frey filaments was ≤5 g of force (which corresponds to monofilament number 4.56 or less). Animals were deemed to have developed thermal hyperalgesia if their left paw withdrawal latency to the thermal plantar device showed ≥30% difference from the left paw pre-surgery value, prior to dosing.

6 Dosing and Behavioural Testing

The animals were not fasted for this study. On each day of dosing, the allocated animals each received a single intravenous dose of test substance, reference substance or vehicle; or an oral dose of comparator substance or vehicle. There were 3 phases to the study. The dosing of each phase was split over 2 days and animals from a minimum of 3 treatment groups were dosed on each dosing day. Following completion of each phase, the animals were allowed a minimum washout period of 1 week before commencing the subsequent phase of the study.

In Phases 1 and 2 of the study, following dosing (approximately 5 min from the start of dosing) and at approximately 25, 50 and 120 min post-dose, the left and right hind paw of each rat was assessed for mechanical allodynia using the Von Frey test. At approximately 15, 35, 60 and 130 min post-dose, the left and right hind paw of each rat was assessed for thermal hyperalgesia using the Hargreaves Plantar test, to investigate treatment effect. All time points were with respect to the start of dosing. In Phase 3 of the study, at approximately 60, 120, 180 and 240 min post-dose the left and right hind limb of each rat were assessed for mechanical allodynia using the Von Frey test. At approximately 70, 130, 190 and 250 min post-dose, the left and right hind limb of each rat were assessed for thermal hyperalgesia using the Hargreaves Plantar test, to investigate treatment effect.

7 Terminations

All study animals were terminated by cervical dislocation following conclusion of the final testing period.

Statistical Analysis

Statistical comparisons were made between treatment groups using parametric (e.g. one way analysis of variance, Dunnett's t-test, Student's t-test) or non-parametric (e.g. Kruskal-Wallis statistic, Dunn's test, Mann-Whitney U-test) statistical procedures. The choice of parametric or non-parametric test was based on whether the groups to be compared satisfy the homogeneity of variance criterion (evaluated by the Levene Mean test or F-test). The Von Frey data was logarithmically transformed (log 10 of (force in grams×10 000)) prior to analysis. In Phase 2 of the study, as the comparator substance, Pregabalin was administered by a different dose route, the data for Pregabalin were compared to the pre-dose values using a paired Student's t test. In Phase 3 of the study, as the reference substance, Morphine was administered by a different dose route to the vehicle and test substance, the Morphine data were compared to the pre-dose values using a paired Student's t-test. For all tests, statistical significance was assumed when $P<0.05$. The statistical significance for the von Frey test, although performed on the logarithmically transformed data, was expressed with respect to the grams force in the results section for illustration purposes. Full details of the analysis are given in the raw data.

Results

The group mean±s.e. mean data for withdrawal thresholds and withdrawal latency are summarised in Table 17 to Table 22.

Development of Neuropathic Pain States

Two different components of neuropathic pain were investigated using established behavioural tests, namely Von Frey filaments to test for the presence of mechanical allodynia, and the Hargreaves Plantar test to test for the presence of thermal hyperalgesia. The majority of animals which underwent a spinal nerve ligation, exhibited a marked increase in sensitivity of the left hind paw to the two behavioural tests in the days post-injury, indicative of the development of a peripheral mononeuropathy. The right hind paw showed no increase in sensitivity post surgery. In each Phase of the study, all animals dosed were deemed to have neuropathy in the left hind paw as assessed using the established behavioural tests the day prior to dosing.

Effects of R-DHE on Behavioural Test Responses (Phase 1)

Figure 18:
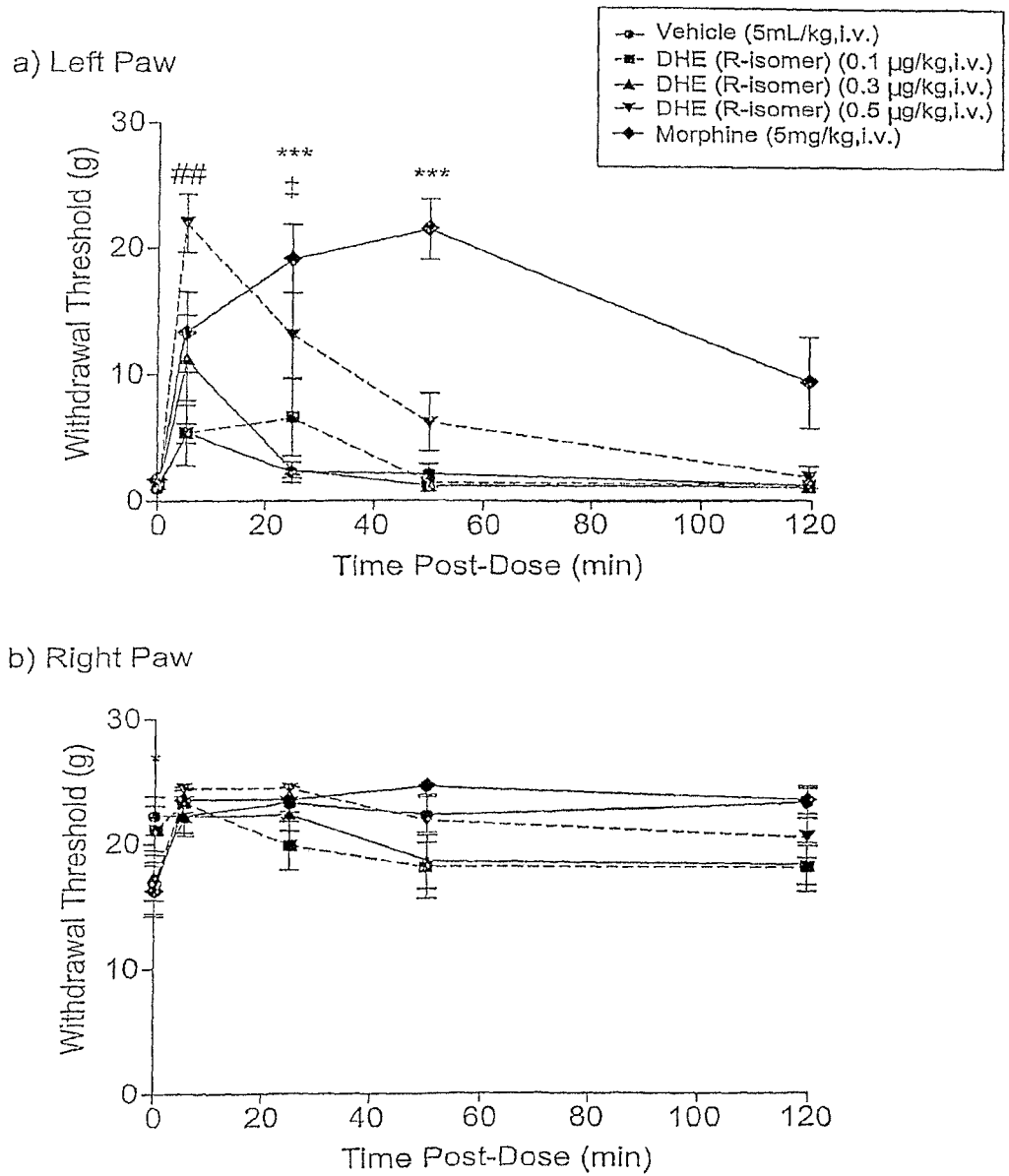
FIGS. 18 to 23 show the effects of intravenous administration of (R)- or (S)-DHE or a reference or comparator substance in the spinal nerve ligation model of neuropathic pain.

Mechanical allodynia: In Phase 1, intravenous administration of R-DHE at 0.1 and 0.3 µg/kg did not produce any significant changes in left or right paw withdrawal thresholds to Von Frey filaments. However, intravenous administration of R-DHE at 0.5 µg/kg, caused a significant increase in the left paw withdrawal threshold at approximately 5 min post-dose (21.97±2.30 g; P<0.01; Kruskal-Wallis and Dunn's test) when compared to vehicle group values of 5.43±2.58 g, and also at approximately 25 min post-dose (13.12±3.41 g; P<0.05; ANOVA and Dunnett's t-test) when compared to vehicle group values of 2.25±0.75 g (Table 17, FIG. 18).

Figure 19:
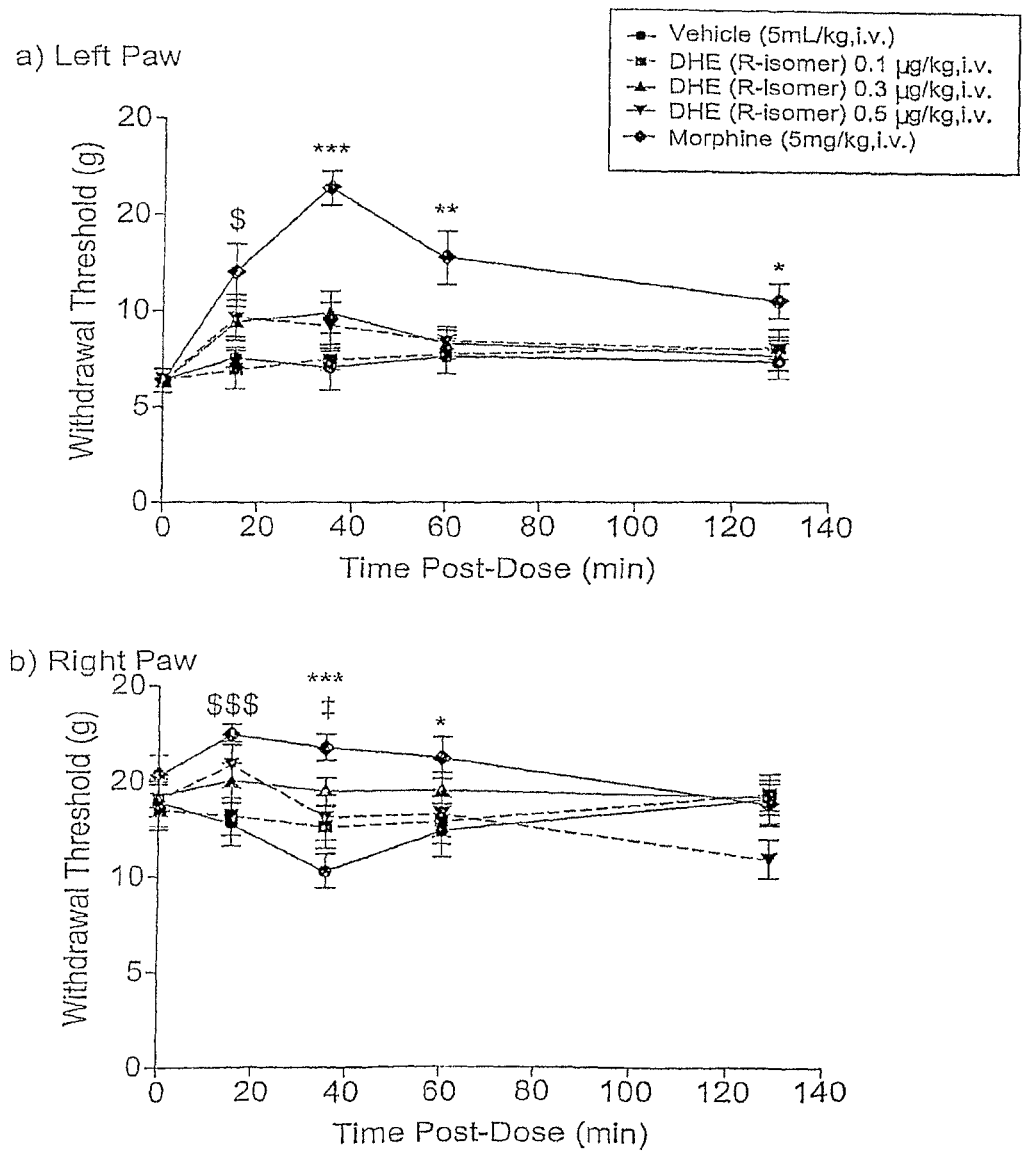

Thermal hyperalgesia: Intravenous administration of R-DHE failed to have a significant effect on left paw withdrawal latencies when compared to vehicle. Intravenous administration of R-DHE at a dose of 0.3 µg/kg caused a significant increase in the right paw withdrawal latency at approximately 35 min post-dose (14.5±0.7 s; P<0.05; ANOVA and Dunnett's t-test) when compared to vehicle values (10.3±0.9 s); however, this is physiologically irrelevant as the withdrawal threshold in the right paw was similar to the pre dose values for the right paw (14.3±0.6 s) (Table 18, FIG. 19).

Effects of S-DHE on Behavioural Test Responses (Phase 2)

Figure 20:
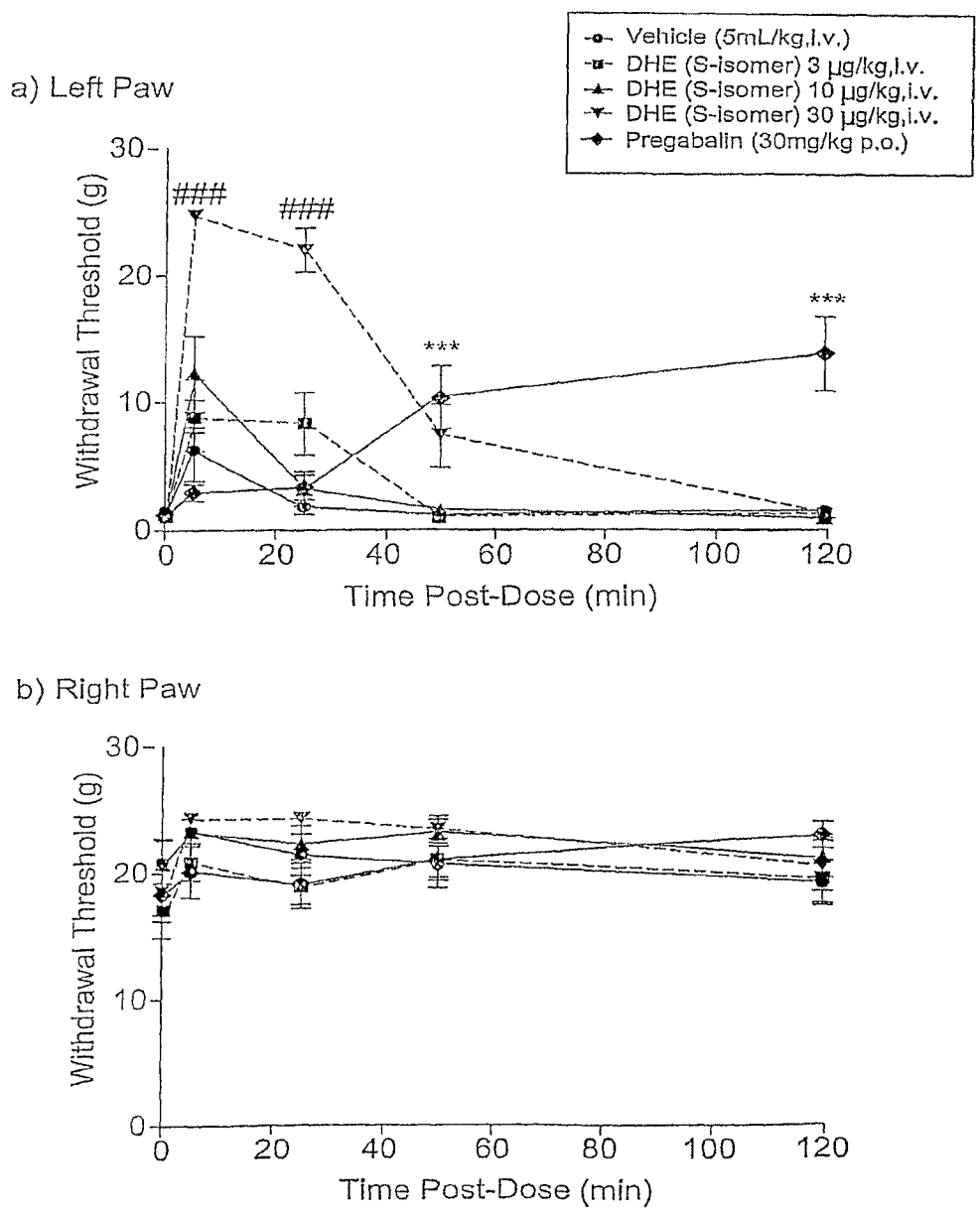

Mechanical allodynia: In Phase 2, intravenous administration of S-DHE at 3 and 10 µg/kg did not produce any significant changes in left or right paw withdrawal thresholds to Von Frey filaments. However, intravenous administration at 30 µg/kg caused a significant increase in the left paw withdrawal threshold at approximately 5 min post-dose (24.56±0.33 g; P≤0.001; Kruskal-Wallis and Dunn's test) when compared to vehicle group values of 6.11±2.39 g, and also at approximately 25 min post-dose (21.92±1.70 g; P<0.001; Kruskal Wallis and Dunn's test) when compared to vehicle group values of 1.66±0.47 g (Table 19, FIG. 20).

Figure 21:
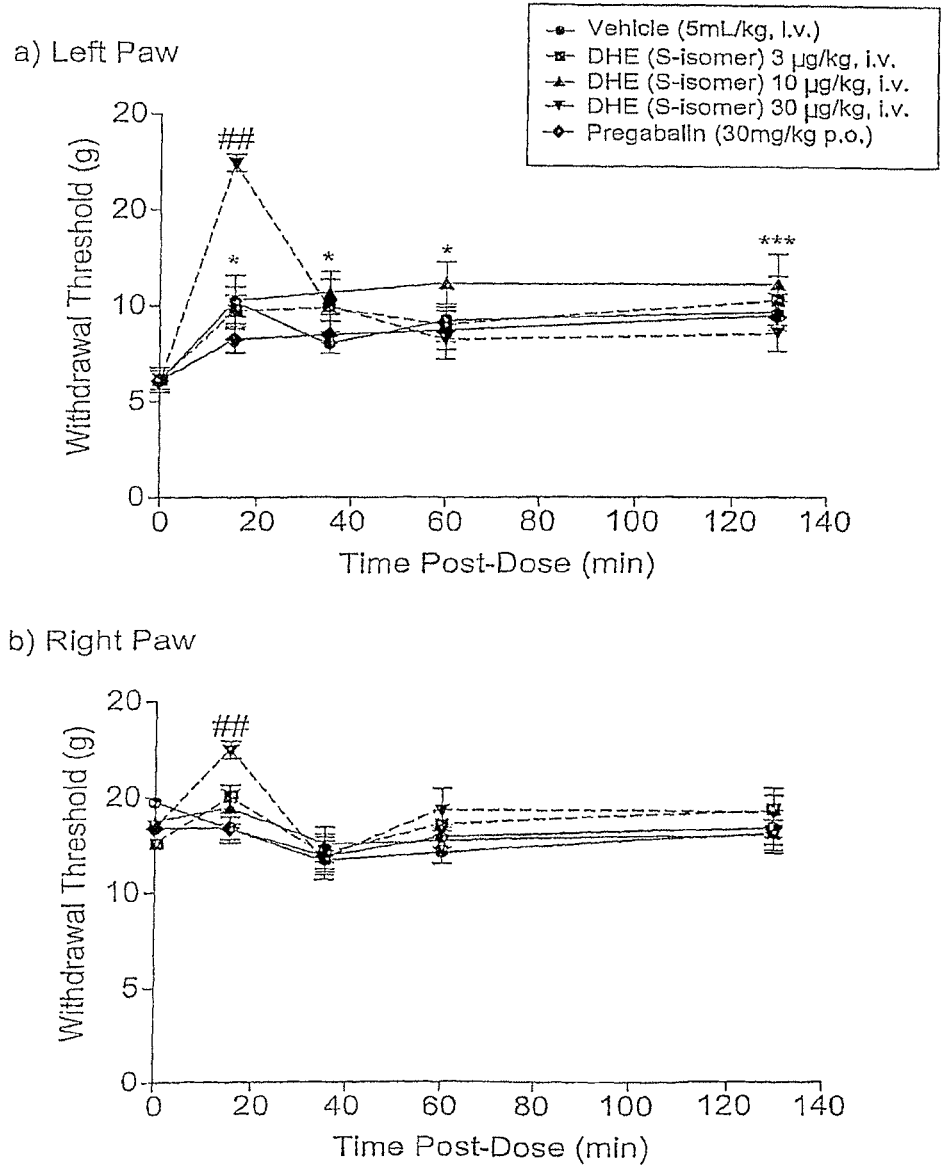

Thermal hyperalgesia: Intravenous administration of S-DHE failed to have a significant effect on left and right paw withdrawal latencies at doses of 3 and 10 µg/kg when compared to the vehicle group values. Intravenous administration of S-DHE at a dose of 30 µg/kg, however, did produce a significant increase in the paw withdrawal latencies at approximately 15 min post-dose in both left (17.6±0.4 s; P<0.01; Kruskal-Wallis and Dunn's test) and right (17.5±0.4 s; P<0.01; Kruskal-Wallis and Dunn's test) hind paws, when compared to vehicle values of 10.3±0.8 s and 13.4±0.8 s, respectively. The increase in right paw latency may be indicative of the central effects of dihydroetophine (S-isomer) at the 30 µg/kg dose level (Table 20, FIG. 21).

Effects of Morphine on Behavioural Test Responses (Phases 1 and 3)

In Phase 1, the morphine reference was compared to vehicle as both were administered orally. In Phase 3, the morphine reference was compared to pre-dose as it was not be relevant to compare this to an oral vehicle).

Mechanical allodynia: Following intravenous administration of morphine at 5 mg/kg (Phase 1), the left hind paw withdrawal threshold significantly increased at approximately 25 min post-dose (19.23±2.73 g; P<0.001; unpaired 2-tailed Student's t-test) and approximately 50 min post-dose (21.55±2.40 g; P<0.001; unpaired 2-tailed Student's t test) when compared to vehicle values of 2.25±0.75 and 2.11±0.82 g. There was a significant decrease observed in the right paw pre dose data (16.37±2.20 g; P<0.05; unpaired 2-tailed Student's t-test) when compared to vehicle values (22.26±1.52 g). This was unavoidable, as the allocation to treatment groups was based on the pre-dose values from the thermal hyperalgesia test (Table 17, FIG. 18). No other significant effects were noted in the right hind paw.

Figure 22:
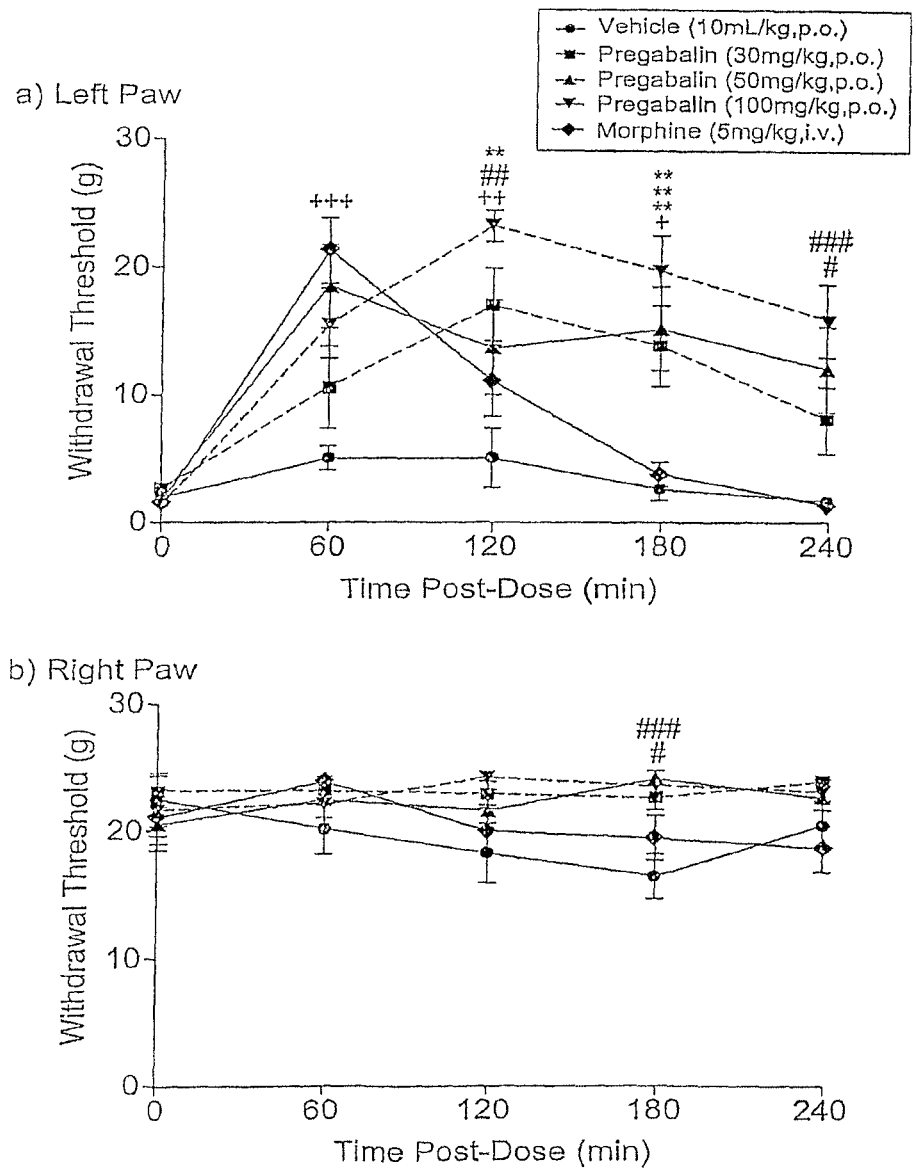

In Phase 3, intravenous administration of morphine (5 mg/kg) significantly increased the left paw withdrawal thresholds at approximately 60 min (21.32±2.56 g; P<0.001; paired 2 tailed Student's t-test), 120 min (11.08±2.85 g; P<0.01; paired 2-tailed Student's t-test) and approximately 180 min post-dose (3.68±0.97 g; P<0.05; paired 2-tailed Student's t test) compared to pre-dose values 1.46±0.37 g (Table 21, FIG. 22).

Thermal hyperalgesia: In Phase 1, intravenous administration of morphine at 5 mg/kg caused a significant increase in the withdrawal latencies in the left paw across all of the time points tested and in the right paw at approximately 15, 35 and 60 min post-dose. At approximately 15 min post-dose; (left; 12.0±1.5 s; P<0.05; Mann-Whitney U-test), (right; 17.5±0.5 s; P<0.001; Mann-Whitney U-test), at 35 min post-dose (left; 16.4±0.9 s; P<0.001; unpaired 2-tailed Student's t-test), (right; 16.8±0.7 s; P<0.001; unpaired 2-tailed Student's t-test) and at approximately 60 min post-dose in both paws (left; 12.8±1.3 s; P<0.01; unpaired 2 tailed Student's t-test), (right; 16.3±1.1 s; P<0.05; unpaired 2-tailed Student's t-test) and approximately 130 min post-dose in the left paw (10.6±0.9 s; P<0.05; unpaired 2-tailed Student's t-test) when compared to vehicle values (7.5±0.5, 12.8±1.1, 7.0±1.2, 10.3±0.9, 7.6±0.9, 12.4±1.4 and 7.4±0.9 s, respectively) (Table 18, FIG. 19).

Figure 23:
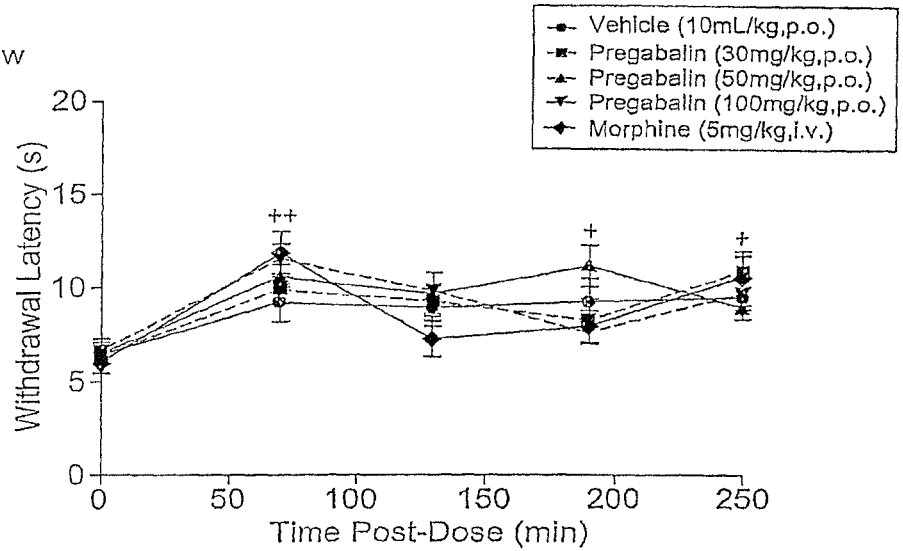
Figure 23:
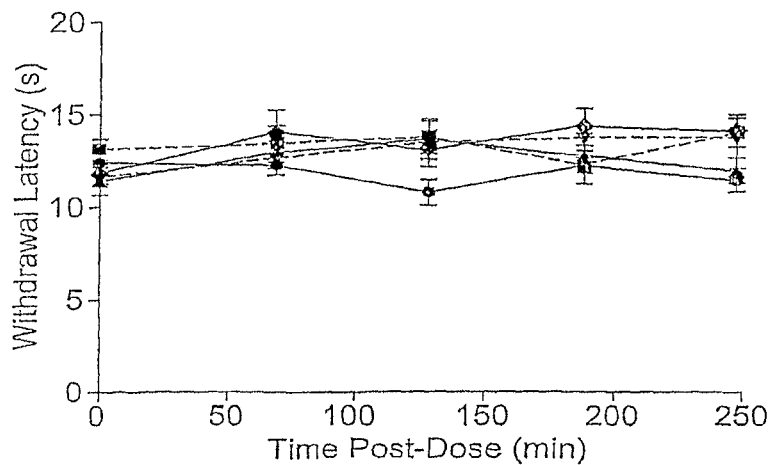

In Phase 3 of the study, intravenous administration of morphine caused a significant increase in left paw withdrawal latency at approximately 70 min post-dose (11.8±1.2 s; P<0.01; paired 2-tailed Student's t-test), approximately 190 min post-dose (8.0±0.8 s; P<0.05; paired 2-tailed Student's t-test) and approximately 250 min post-dose (10.6±1.4 s; P<0.05; paired 2-tailed Student's t-test) when compared to pre-dose values of 6.0±0.5 s (Table 22, FIG. 23).

Effects of Pregabalin on Behavioural Test Responses (Phases 2 and 3)

Pregabalin was compared to pre-dose in Phase 2 but compared to vehicle in Phase 3 of the study. In Phase 2 of the study the Pregabalin was administered by a different route (oral) to the vehicle (iv), so a comparison with vehicle was not appropriate. In Phase 3 of the study the dose response to Pregabalin, using 3 dose levels was compared to vehicle rather than pre dose.

Mechanical allodynia: In Phase 2, oral administration of Pregabalin (30 mg/kg) caused a significant increase in the left paw withdrawal threshold at approximately 50 min post-dose (10.35±2.51 g; P<0.001; paired 2-tailed Student's t-test) and approximately 120 min post dose (13.90±3.00 g; P<0.001; paired 2-tailed Student's t-test) when compared to pre dose values of 1.09±0.35 g. (Table 19, FIG. 20).

In Phase 3, Pregabalin, administered orally, at a dose of 30 mg/kg caused a significant increase in the left paw withdrawal threshold at approximately 120 min post-dose (17.06±2.88 g; P<0.01; Kruskal-Wallis and Dunn's test) and approximately 180 min post dose (13.86±3.21 g; P<0.01; ANOVA and Dunnett's test) when compared to vehicle values of 5.00±2.34 g and 2.57±0.92 g, respectively. Oral administration of Pregabalin at a dose of 50 mg/kg caused a significant increase and both left and right paw withdrawal thresholds at approximately 180 min post-dose (left paw: 15.20±3.31 g; P<0.01; ANOVA and Dunnett's test and right paw: 24.20±0.39 g; P<0.05; Kruskal-Wallis and Dunn's test) when compared to vehicle values of 2.57±0.92 g and 16.57±1.75 g, respectively, and on the left paw withdrawal threshold at approximately 240 min post-dose (12.05±3.41 g; P<0.05; Kruskal-Wallis and Dunn's test) when compared to vehicle values (1.48±0.30 g). Oral administration of Pregabalin at a dose of 100 mg/kg caused a significant increase in left paw withdrawal threshold at approximately 120 min post-dose (23.29±1.19 g; P<0.01; ANOVA and Dunnett's test), in left and right paws at approximately 180 min post-dose (left paw: 19.77±2.70 g; P<0.01; ANOVA and Dunnett's test and right paw: 23.70±1.04 g; P<0.01; Kruskal-Wallis and Dunn's test) when compared to vehicle values of 2.57±0.92 and 16.57±1.75 g. respectively, and at approximately 240 min post-dose in the left paw withdrawal threshold (15.91±2.86 g; P<0.001; Kruskal-Wallis and Dunn's test) when compared to vehicle values (1.48±0.30 g). The increase in the right paw withdrawal thresholds following administration of Pregabalin at 50 and 100 mg/kg, was indicative of the central effects of Pregabalin at these dose levels. This was consistent with the animals displaying a dose-dependant increase in the level of sedative clinical symptoms. (Table 21, FIG. 22).

Thermal hyperalgesia: In Phase 2, oral administration of Pregabalin (30 mg/kg) caused a significant increase in the left paw withdrawal latency at approximately 15, 35, 60 and 130 min post-dose (8.3±0.7 s P<0.05; 8.6±1.0 s P<0.05; 8.8±1.0 s P<0.05; 9.6±0.8 s P<0.001; all paired 2-tailed Student's t-test) when compared to the pre dose value of 6.2±0.5 s. These significant increases were not deemed to be pharmacologically relevant, as there were similar increases in the values for withdrawal latencies in the vehicle control group (iv administration) in Phase 2 (approximately 15, 35, 60 and 130 min post-dose (10.3±0.8 s P<0.01; 8.1±0.5 s P<0.05; 9.3±0.7 s P<0.001; 9.8±1.0 s P<0.01; all paired 2-tailed Student's t-test) when compared to the pre dose value of 6.2±0.5 s), and in Phase 3 of the study, oral administration of Pregabalin failed to have a significant effect in left and right paw withdrawal latencies, at all of the doses tested (30, 50 and 100 mg/kg) and across all post-dose time points (60, 120, 180 and 240 min), when compared to the vehicle control. (Table 20, FIG. 21 and Table 22, FIG. 23).

Conclusion

A peripheral mononeuropathy was induced in the left hind limb of rats by tight ligation of the L5 and L6 spinal nerves. The development of mechanical allodynia and thermal hyperalgesia was monitored using established behavioural tests (Von Frey test and the Hargreaves Plantar test, respectively). Response threshold and latency was assessed for both the left (affected) and right (unaffected) hind paws. In each Phase of the study, all animals dosed were deemed to have neuropathy in the left hind paw as assessed using the established behavioural tests the day prior to dosing.

Intravenous administration of R-DHE at 0.5 µg/kg caused an increase in withdrawal threshold (mechanical allodynia) of up to 25 min post-dose with peak effects at approximately 5 min post-dose. There were no effects of R-DHE at 0.5 µg/kg on withdrawal latency (thermal hyperalgesia) at any of the time points tested. There were also no effects on either mechanical allodynia or thermal hyperalgesia at the lower doses of 0.1 and 0.3 µg/kg of R-DHE.

Intravenous administration of S-DHE at a dose of 30 µg/kg caused significant analgesic effects in both withdrawal threshold (mechanical allodynia), with peak effects at approximately 5 to 25 min post-dose and withdrawal latency (thermal hyperalgesia), with peak effect at approximately 15 min post dose. No effects on mechanical allodynia or thermal hyperalgesia were noted at 3 and 10 µg/kg of S-DHE.

Intravenous administration of the opioid compounds, R-DHE and S-DHE demonstrated analgesic activity in both the mechanical allodynia and thermal hyperalgesia test in the rat. This highlights the therapeutic potential of these compounds in the treatment of neuropathic pain.

Following administration of Pregabalin (in Phase 3) at doses up to 100 mg/kg, there was a dose dependent increase in withdrawal threshold with peak effects between approximately 180 and 240 min post-dose. There were no effects of pregabalin in the thermal hyperalgesia test. The effects noted following administration of Pregabalin were consistent with its known pharmacological activity (based on literature data) with significant effects on mechanical allodynia, but a limited effect on thermal hyperalgesia.

The effects noted following intravenous administration of morphine were consistent with its known pharmacological activity with significant effects on mechanical allodynia and thermal hyperalgesia. This test system was therefore sensitive to detect nociceptive effects in both the mechanical allodynia and the thermal hyperalgesia test in the rat.

TABLE 17

Effects of intravenous R-DHE on the left (L) and right (R) paw withdrawal thresholds to Von Frey monofilament challenges in rats (Phase 1)

(a) Raw Data

Withdrawal Threshold (g) at Time (min) Post-Dose

| | Pre-Dose | | Phase 1 | | | |
|---|---|---|---|---|---|---|
| | | | 5 | | 25 | |
| Treatment | L | R | L | R | L | R |
| Vehicle† 5 mL/kg, i.v. | 0.95 ± 0.09 (9) | 22.26 ± 1.52 (9) | 5.43 ± 2.58 (9) | 22.26 ± 1.52 (9) | 2.25 ± 0.75 (9) | 23.25 ± 1.16 (9) |
| Dihydroetorphine (R) 0.1 µg/kg, i.v. | 1.37 ± 0.31 | 21.07 ± 1.99 | 5.35 ± 0.79 | 23.30 ± 1.00 | 6.55 ± 3.04 | 19.81 ± 1.97 |
| Dihydroetorphine (R) 0.3 µg/kg, i.v. | 1.27 ± 0.33 | 17.45 ± 2.01 | 11.13 ± 3.54 | 22.20 ± 1.30 | 2.41 ± 0.59 | 22.37 ± 1.36 |
| Dihydroetorphine (R) 0.5 µg/kg, i.v. | 1.05 ± 0.18 | 16.32 ± 1.99 | 21.97 ± 2.30 | 24.36 ± 0.34 | 13.12 ± 3.41 | 24.36 ± 0.34 |
| Morphine 5 mg/kg, i.v. | 1.69 ± 0.53 | 16.37 ± 2.20 | 13.38 ± 3.14 | 23.50 ± 1.02 | 19.23 ± 2.73 | 23.50 ± 1.02 |

(a) Raw Data

Withdrawal Threshold (g) at Time (min) Post-Dose
Phase 1

| | 50 | | 120 | |
|---|---|---|---|---|
| Treatment | L | R | L | R |
| Vehicle† 5 mL/kg, i.v. | 2.11 ± 0.82 (9) | 22.26 ± 1.52 (9) | 1.09 ± 0.23 (9) | 23.25 ± 1.16 (9) |
| Dihydroetorphine (R) 0.1 µg/kg, i.v. | 1.35 ± 0.32 | 18.11 ± 2.52 | 1.07 ± 0.16 | 18.05 ± 1.94 |
| Dihydroetorphine (R) 0.3 µg/kg, i.v. | 1.14 ± 0.31 | 18.55 ± 2.25 | 0.95 ± 0.10 | 18.25 ± 1.54 |
| Dihydroetorphine (R) 0.5 µg/kg, i.v. | 6.17 ± 2.33 | 21.84 ± 1.77 | 1.80 ± 0.88 | 20.41 ± 1.63 |
| Morphine 5 mg/kg, i.v. | 21.55 ± 2.40 | 24.56 ± 0.33 | 9.37 ± 3.60 | 23.46 ± 1.06 |

(b) Log Data

Withdrawal Threshold (Log 10 (force (g) × 10 000)) at Time (min) Post-Dose

| | Pre-Dose | | Phase 1 | | | |
|---|---|---|---|---|---|---|
| | | | 5 | | 25 | |
| Treatment | L | R | L | R | L | R |
| Vehicle† 5 mL/kg, i.v. | 3.96 ± 0.04 (9) | 5.34 ± 0.03 (9) | 4.48 ± 0.16 (9) $ | 5.34 ± 0.03 (9) | 4.21 ± 0.12 (9) | 5.36 ± 0.03 (9) |
| Dihydroetorphine (R) 0.1 µg/kg, i.v. | 4.06 ± 0.08 | 5.30 ± 0.05 | 4.65 ± 0.10 | 5.36 ± 0.02 | 4.42 ± 0.19 | 5.27 ± 0.05 |
| Dihydroetorphine (R) 0.3 µg/kg, i.v. | 4.01 ± 0.09 | 5.21 ± 0.05 | 4.71 ± 0.20 | 5.34 ± 0.03 | 4.26 ± 0.10 | 5.34 ± 0.03 |
| Dihydroetorphine (R) 0.5 µg/kg, i.v. | 3.96 ± 0.07 | 5.18 ± 0.05 | 5.26 ± 0.12 ## | 5.39 ± 0.01 | 4.89 ± 0.17 ‡ | 5.39 ± 0.01 |
| Morphine 5 mg/kg, i.v. | 4.08 ± 0.11 | 5.17 ± 0.06 * | 4.93 ± 0.16 | 5.37 ± 0.02 | 5.20 ± 0.11 *** | 5.37 ± 0.02 |

(b) Log Data

Withdrawal Threshold (Log 10 (force (g) × 10 000)) at Time (min) Post-Dose
Phase 1

| | 50 | | 120 | |
|---|---|---|---|---|
| Treatment | L | R | L | R |
| Vehicle† 5 mL/kg, i.v. | 4.12 ± 0.14 (9) | 5.34 ± 0.03 (9) | 3.96 ± 0.08 (9) | 5.36 ± 0.03 (9) |
| Dihydroetorphine (R) 0.1 µg/kg, i.v. | 4.05 ± 0.08 | 5.21 ± 0.07 | 3.99 ± 0.06 | 5.23 ± 0.05 |
| Dihydroetorphine (R) 0.3 µg/kg, i.v. | 3.97 ± 0.08 | 5.23 ± 0.06 | 3.95 ± 0.05 | 5.25 ± 0.04 |

TABLE 17-continued

Effects of intravenous R-DHE on the left (L) and right (R) paw withdrawal thresholds to Von Frey monofilament challenges in rats (Phase 1)

| | | | | |
|---|---|---|---|---|
| Dihydroetorphine (R) 0.5 µg/kg, i.v. | 4.50 ± 0.17 | 5.32 ± 0.05 | 4.03 ± 0.12 | 5.30 ± 0.03 |
| Morphine 5 mg/kg, i.v. | 5.26 ± 0.11 *** | 5.39 ± 0.00 | 4.49 ± 0.23 | 5.36 ± 0.02 |

Data are expressed as Mean ± SEM.
n = 10 animals per group, unless stated in parenthesis.
Statistical analysis only performed on log data.
†Vehicle = citrate buffer (citric acid monohydrate:sodium citrate:sodium chloride:water for injection, in the ratio, 0.03:0.10:0.86:99.01 (g:g:g:mL).
* $P < 0.05$ when compared to vehicle group data (unpaired 2-tailed Student's t-test).
*** $P < 0.001$ when compared to vehicle group data (unpaired 2-tailed Student's t-test).
$P < 0.01$ when compared to vehicle group data (Kruskal-Wallis and Dunn's test).
‡ $P < 0.05$ when compared to vehicle group data (ANOVA and Dunnett's t-test).
$ $P < 0.05$ when compared to pre-dose data (paired 2-tailed Student's t-test).

TABLE 18

Effects of intravenous R-DHE on the left (L) and right (R) paw withdrawal latency to a thermal plantar stimulus in rats (Phase 1)

| | Withdrawal Latency (s) at Time (min) Post-Dose | | | | | |
|---|---|---|---|---|---|---|
| | Pre-Dose | | Phase 1 | | | |
| | | | 15 | | 35 | |
| Treatment | L | R | L | R | L | R |
| Vehicle† 5 mL/kg, i.v. | 6.4 ± 0.5 (9) | 13.9 ± 1.2 (9) | 7.5 ± 0.5 (9) | 12.8 ± 1.1 (9) | 7.0 ± 1.2 (9) | 10.3 ± 0.9 (9) |
| Dihydroetorphine (R) 0.1 µg/kg, i.v. | 6.4 ± 0.5 | 13.5 ± 1.0 | 6.9 ± 1.0 | 13.2 ± 1.0 | 7.4 ± 0.5 | 12.6 ± 1.1 |
| Dihydroetorphine (R) 0.3 µg/kg, i.v. | 6.3 ± 0.6 | 14.3 ± 0.6 | 9.4 ± 0.8 | 15.1 ± 0.9 | 9.9 ± 1.1 | 14.5 ± 0.7 ‡ |
| Dihydroetorphine (R) 0.5 µg/kg, i.v. | 6.4 ± 0.4 | 14.1 ± 0.9 | 9.6 ± 1.2 | 15.9 ± 1.2 | 9.2 ± 1.2 | 13.1 ± 1.2 |
| Morphine 5 mg/kg, i.v. | 6.4 ± 0.4 | 15.4 ± 1.0 | 12.0 ± 1.5 $ | 17.5 ± 0.5 $$$ | 16.4 ± 0.9 *** | 16.8 ± 0.7 *** |

| | Withdrawal Latency (s) at Time (min) Post-Dose | | | |
|---|---|---|---|---|
| | Phase 1 | | | |
| | 60 | | 130 | |
| Treatment | L | R | L | R |
| Vehicle† 5 mL/kg, i.v. | 7.6 ± 0.9 (9) | 12.4 ± 1.4 (9) | 7.4 ± 0.9 (9) | 14.1 ± 1.3 (9) |
| Dihydroetorphine (R) 0.1 µg/kg, i.v. | 7.7 ± 1.0 | 12.9 ± 1.2 | 8.1 ± 0.6 | 14.3 ± 0.8 |
| Dihydroetorphine (R) 0.3 µg/kg, i.v. | 8.3 ± 0.8 | 14.6 ± 0.9 | 7.7 ± 0.8 | 14.2 ± 0.9 |
| Dihydroetorphine (R) 0.5 µg/kg, i.v. | 8.4 ± 0.6 | 13.3 ± 1.2 | 8.0 ± 1.1 | 10.9 ± 1.0 |
| Morphine 5 mg/kg, i.v. | 12.8 ± 1.3 ** | 16.3 ± 1.1 * | 10.6 ± 0.9 * | 13.8 ± 1.1 |

Data are expressed as Mean ± SEM.
n = 10 animals per group, unless stated in parenthesis.
†Vehicle = citrate buffer (citric acid monohydrate:sodium citrate:sodium chloride:water for injection, in the ratio, 0.03:0.10:0.86:99.01 (g:g:g:mL).
$ $P < 0.05$ when compared to vehicle group data (Mann-Whitney U-test).
$$$ $P < 0.001$ when compared to vehicle group data (Mann-Whitney U-test).
* $P < 0.05$ when compared to vehicle group data (unpaired 2-tailed Student's t-test).
** $P < 0.01$ when compared to vehicle group data (unpaired 2-tailed Student's t-test).
*** $P < 0.001$ when compared to vehicle group data (unpaired 2-tailed Student's t-test).
‡ $P < 0.05$ when compared to vehicle group data (ANOVA and Dunnett's t-test).

TABLE 19

Effects of intravenous S-DHE on the left (L) and right (R) paw withdrawal thresholds to Von Frey monofilament challenges in rats (Phase 2)

(a) Raw Data

| | Withdrawal Threshold (g) at Time (min) Post-Dose | | | | | |
|---|---|---|---|---|---|---|
| | | | Phase 2 | | | |
| | Pre-Dose | | 5 | | 25 | |
| Treatment | L | R | L | R | L | R |
| Vehicle† 5 mL/kg, i.v. | 1.37 ± 0.31 | 21.03 ± 1.84 | 6.11 ± 2.39 | 23.46 ± 1.06 | 1.66 ± 0.47 | 21.67 ± 1.61 |
| Dihydroetorphine (S) 3 μg/kg, i.v. | 0.94 ± 0.11 | 17.27 ± 2.12 | 8.69 ± 2.98 | 21.10 ± 1.46 | 8.28 ± 2.48 | 19.15 ± 1.55 |
| Dihydroetorphine (S) 10 μg/kg, i.v. | 1.19 ± 0.31 | 20.94 ± 1.90 | 12.15 ± 2.99 | 23.46 ± 1.06 | 3.09 ± 1.35 | 22.57 ± 1.39 |
| Dihydroetorphine (S) 30 μg/kg, i.v. | 0.84 ± 0.10 | 18.78 ± 1.89 | 24.56 ± 0.33 | 24.56 ± 0.33 | 21.92 ± 1.70 | 24.56 ± 0.33 |
| Pregabalin 30 mg/kg, p.o. | 1.09 ± 0.35 | 18.63 ± 2.21 | 2.83 ± 0.62 | 20.42 ± 2.14 | 3.27 ± 0.97 | 19.39 ± 1.61 |

(a) Raw Data

| | Withdrawal Threshold (g) at Time (min) Post-Dose Phase 2 | | | |
|---|---|---|---|---|
| | 50 | | 120 | |
| Treatment | L | R | L | R |
| Vehicle† 5 mL/kg, i.v. | 1.11 ± 0.15 | 20.94 ± 1.90 | 1.35 ± 0.28 | 19.55 ± 1.69 |
| Dihydroetorphine (S) 3 μg/kg, i.v. | 0.99 ± 0.12 | 21.27 ± 1.53 | 1.19 ± 0.20 | 19.84 ± 1.94 |
| Dihydroetorphine (S) 10 μg/kg, i.v. | 1.48 ± 0.42 | 23.46 ± 1.06 | 0.83 ± 0.10 | 21.51 ± 1.55 |
| Dihydroetorphine (S) 30 μg/kg, i.v. | 7.34 ± 2.47 | 23.67 ± 1.07 | 1.20 ± 0.34 | 20.83 ± 1.99 |
| Pregabalin 30 mg/kg, p.o. | 10.35 ± 2.51 | 21.34 ± 1.49 | 13.90 ± 3.00 | 23.26 ± 1.04 |

(b) Log Data

| | Withdrawal Threshold (Log 10 (force (g) × 10 000)) at Time (min) Post-Dose | | | | | |
|---|---|---|---|---|---|---|
| | | | Phase 2 | | | |
| | Pre-Dose | | 5 | | 25 | |
| Treatment | L | R | L | R | L | R |
| Vehicle† 5 mL/kg, i.v. | 4.07 ± 0.07 | 5.30 ± 0.05 | 4.50 ± 0.16 $ | 5.36 ± 0.02 | 4.11 ± 0.10 | 5.32 ± 0.04 |
| Dihydroetorphine (S) 3 μg/kg, i.v. | 3.95 ± 0.05 | 5.20 ± 0.06 | 4.60 ± 0.20 | 5.31 ± 0.03 | 4.69 ± 0.17 | 5.27 ± 0.04 |
| Dihydroetorphine (S) 10 μg/kg, i.v. | 3.99 ± 0.08 | 5.30 ± 0.05 | 4.90 ± 0.16 | 5.36 ± 0.02 | 4.26 ± 0.13 | 5.34 ± 0.03 |
| Dihydroetorphine (S) 30 μg/kg, i.v. | 3.90 ± 0.05 | 5.25 ± 0.05 | 5.39 ± 0.00 ### | 5.39 ± 0.00 | 5.32 ± 0.04 ### | 5.39 ± 0.00 |
| Pregabalin 30 mg/kg, p.o. | 3.92 ± 0.09 | 5.24 ± 0.06 | 4.31 ± 0.13 | 5.28 ± 0.06 | 4.35 ± 0.13 | 5.27 ± 0.04 |

(b) Log Data

| | Withdrawal Threshold (Log 10 (force (g) × 10 000)) at Time (min) Post-Dose Phase 2 | | | |
|---|---|---|---|---|
| | 50 | | 120 | |
| Treatment | L | R | L | R |
| Vehicle† 5 mL/kg, i.v. | 4.01 ± 0.06 | 5.30 ± 0.05 | 4.08 ± 0.06 | 5.28 ± 0.04 |
| Dihydroetorphine (S) 3 μg/kg, i.v. | 3.96 ± 0.06 | 5.32 ± 0.03 | 4.02 ± 0.07 | 5.27 ± 0.05 |
| Dihydroetorphine (S) 10 μg/kg, i.v. | 4.05 ± 0.10 | 5.36 ± 0.02 | 3.89 ± 0.05 | 5.32 ± 0.03 |

TABLE 19-continued

Effects of intravenous S-DHE on the left (L) and right (R) paw withdrawal thresholds to Von Frey monofilament challenges in rats (Phase 2)

| | | | | |
|---|---|---|---|---|
| Dihydroetorphine (S) 30 μg/kg, i.v. | 4.60 ± 0.17 | 5.37 ± 0.02 | 3.97 ± 0.09 | 5.29 ± 0.05 |
| Pregabalin 30 mg/kg, p.o. | 4.87 ± 0.14 *** | 5.32 ± 0.03 | 5.03 ± 0.11 *** | 5.36 ± 0.02 |

Data are expressed as Mean ± SEM.
n = 10 animals per group.
Statistical analysis only performed on log data.
†Vehicle = citrate buffer (citric acid monohydrate:sodium citrate:sodium chloride:water for injection, in the ratio, 0.03:0.10:0.86:99.01 (g:g:g:mL)).
*** P < 0.001 when compared to pre-dose data (paired 2-tailed Student's t-test).
### P < 0.001 when compared to vehicle group data (Kruskal-Wallis and Dunn's test).
$ P < 0.05 when compared to pre-dose data (paired 2-tailed Student's t-test).

TABLE 20

Effects of intravenous S-DHE on the left (L) and right (R) paw withdrawal latency to a thermal plantar stimulus in rats (Phase 2)

| | Withdrawal Latency (s) at Time (min) Post-Dose Phase 2 | | | | | |
|---|---|---|---|---|---|---|
| | Pre-Dose | | 15 | | 35 | |
| Treatment | L | R | L | R | L | R |
| Vehicle† 5 mL/kg, i.v. | 6.2 ± 0.5 | 14.8 ± 0.6 | 10.3 ± 0.8$$ | 13.4 ± 0.8 | 8.1 ± 0.5$ | 11.7 ± 0.7$ |
| Dihydroetorphine (S) 3 μg/kg, i.v. | 6.2 ± 0.6 | 12.6 ± 0.7 | 9.8 ± 0.9 | 15.0 ± 0.7 | 10.0 ± 0.7 | 12.1 ± 0.9 |
| Dihydroetorphine (S) 10 μg/kg, i.v. | 6.2 ± 0.6 | 13.8 ± 0.8 | 10.4 ± 1.3 | 14.5 ± 0.9 | 10.8 ± 1.1 | 12.5 ± 0.9 |
| Dihydroetorphine (S) 30 μg/kg, i.v. | 6.2 ± 0.5 | 13.5 ± 0.9 | 17.6 ± 0.4 ## | 17.5 ± 0.4 ## | 10.1 ± 1.4 | 11.8 ± 1.1 |
| Pregabalin 30 mg/kg, p.o. | 6.2 ± 0.5 | 13.4 ± 0.9 | 8.3 ± 0.7 * | 13.4 ± 0.6 | 8.6 ± 1.0 * | 11.9 ± 0.8 |

| | Withdrawal Latency (s) at Time (min) Post-Dose Phase 2 | | | |
|---|---|---|---|---|
| | 60 | | 130 | |
| Treatment | L | R | L | R |
| Vehicle† 5 mL/kg, i.v. | 9.3 ± 0.7$$$ | 12.1 ± 0.6$ | 9.8 ± 1.0$$ | 13.1 ± 1.0 |
| Dihydroetorphine (S) 3 μg/kg, i.v. | 9.1 ± 0.9 | 13.5 ± 0.8 | 10.4 ± 1.3 | 14.3 ± 0.8 |
| Dihydroetorphine (S) 10 μg/kg, i.v. | 11.3 ± 1.1 | 12.7 ± 0.6 | 11.3 ± 1.6 | 13.0 ± 0.8 |
| Dihydroetorphine (S) 30 μg/kg, i.v. | 8.3 ± 1.0 | 14.3 ± 1.1 | 8.7 ± 0.9 | 14.2 ± 1.3 |
| Pregabalin 30 mg/kg, p.o. | 8.8 ± 1.0 * | 12.9 ± 0.6 | 9.6 ± 0.8 *** | 13.4 ± 0.9 |

Data are expressed as Mean ± SEM.
n = 10 animals per group.
†Vehicle = citrate buffer (citric acid monohydrate:sodium citrate:sodium chloride:water for injection, in the ratio, 0.03:0.10:0.86:99.01 (g:g:g:mL)).
## P < 0.01 when compared to vehicle group data (Kruskal-Wallis and Dunn's test).
* P < 0.05 when compared to pre-dose data (paired 2-tailed Student's t-test).
*** P < 0.001 when compared to pre-dose data (paired 2-tailed Student's t-test).
$P < 0.05,
$$P < 0.01 and
$$$P < 0.001 when compared to pre-dose data (paired 2-tailed Student's t-test).

TABLE 21

Effects of oral Pregabalin and intravenous morphine on the left (L) and right (R) paw withdrawal thresholds to Von Frey monofilament challenges in neuropathic rats (Phase 3)

(a) Raw Data

| | Withdrawal Threshold (g) at Time (min) Post-Dose | | | | | |
|---|---|---|---|---|---|---|
| | Phase 3 | | | | | |
| | Pre-Dose | | 60 | | 120 | |
| Treatment | L | R | L | R | L | R |
| Vehicle† 10 mL/kg, p.o. | 1.87 ± 0.38 | 22.53 ± 1.97 | 4.95 ± 0.95 | 20.30 ± 1.99 | 5.00 ± 2.34 | 18.36 ± 2.34 |
| Pregabalin 30 mg/kg, p.o. | 2.59 ± 0.63 | 23.25 ± 1.41 | 10.53 ± 3.25 | 23.26 ± 1.04 | 17.06 ± 2.88 | 23.02 ± 1.01 |
| Pregabalin 50 mg/kg, p.o. | 2.02 ± 0.35 | 20.61 ± 2.00 | 18.48 ± 3.27 | 22.57 ± 1.39 | 13.69 ± 3.68 | 21.67 ± 1.61 |
| Pregabalin 100 mg/kg, p.o. | 1.31 ± 0.18 | 21.67 ± 1.93 | 15.53 ± 2.78 | 22.24 ± 1.82 | 23.29 ± 1.19 | 24.28 ± 0.37 |
| Morphine 5 mg/kg, i.v. | 1.46 ± 0.37 (9) | 21.26 ± 2.11 (9) | 21.32 ± 2.56 (9) | 24.02 ± 0.34 (9) | 11.08 ± 2.85 (9) | 20.04 ± 1.81 (9) |

(a) Raw Data

| | Withdrawal Threshold (g) at Time (min) Post-Dose Phase 3 | | | |
|---|---|---|---|---|
| | 180 | | 240 | |
| Treatment | L | R | L | R |
| Vehicle† 10 mL/kg, p.o. | 2.57 ± 0.92 | 16.57 ± 1.75 | 1.48 ± 0.30 | 20.54 ± 1.93 |
| Pregabalin 30 mg/kg, p.o. | 13.86 ± 3.21 | 22.74 ± 0.97 | 8.02 ± 2.65 | 23.99 ± 0.38 |
| Pregabalin 50 mg/kg, p.o. | 15.20 ± 3.31 | 24.20 ± 0.39 | 12.05 ± 3.41 | 22.74 ± 0.97 |
| Pregabalin 100 mg/kg, p.o. | 19.77 ± 2.70 | 23.70 ± 1.04 | 15.91 ± 2.86 | 23.18 ± 1.00 |
| Morphine 5 mg/kg, i.v. | 3.68 ± 0.97 (9) | 19.57 ± 1.75 (9) | 1.29 ± 0.20 (9) | 18.71 ± 1.81 (9) |

(b) Log Data

| | Withdrawal Threshold (Log 10 (force (g) × 10 000)) at Time (min) Post-Dose | | | | | |
|---|---|---|---|---|---|---|
| | Phase 3 | | | | | |
| | Pre-Dose | | 60 | | 120 | |
| Treatment | L | R | L | R | L | R |
| Vehicle† 10 mL/kg, p.o. | 4.20 ± 0.08 | 5.33 ± 0.05 | 4.57 ± 0.13 $$ | 5.28 ± 0.05 | 4.43 ± 0.15 | 5.22 ± 0.07 |
| Pregabalin 30 mg/kg, p.o. | 4.29 ± 0.11 | 5.35 ± 0.03 | 4.70 ± 0.20 | 5.36 ± 0.02 | 5.13 ± 0.11 ## | 5.36 ± 0.02 |
| Pregabalin 50 mg/kg, p.o. | 4.25 ± 0.07 | 5.29 ± 0.05 | 5.10 ± 0.16 | 5.34 ± 0.03 | 4.85 ± 0.19 | 5.32 ± 0.04 |
| Pregabalin 100 mg/kg, p.o. | 4.07 ± 0.06 | 5.31 ± 0.05 | 5.08 ± 0.12 | 5.33 ± 0.05 | 5.36 ± 0.03 ** | 5.38 ± 0.01 |
| Morphine 5 mg/kg, i.v. | 4.08 ± 0.09 (9) | 5.30 ± 0.05 (9) | 5.22 ± 0.15 +++ (9) | 5.38 ± 0.01 (9) | 4.89 ± 0.14 ++ (9) | 5.29 ± 0.04 (9) |

(b) Log Data

| | Withdrawal Threshold (Log 10 (force (g) × 10 000)) at Time (min) Post-Dose Phase 3 | | | |
|---|---|---|---|---|
| | 180 | | 240 | |
| Treatment | L | R | L | R |
| Vehicle† 10 mL/kg, p.o. | 4.23 ± 0.12 | 5.20 ± 0.05 | 4.11 ± 0.07 | 5.29 ± 0.05 |
| Pregabalin 30 mg/kg, p.o. | 4.95 ± 0.16 ** | 5.35 ± 0.02 | 4.68 ± 0.16 | 5.38 ± 0.01 |
| Pregabalin 50 mg/kg, p.o. | 5.00 ± 0.15 ** | 5.38 ± 0.01 # | 4.83 ± 0.18 # | 5.35 ± 0.02 |

TABLE 21-continued

Effects of oral Pregabalin and intravenous morphine on the left (L) and right (R) paw withdrawal thresholds to Von Frey monofilament challenges in neuropathic rats (Phase 3)

| | | | | |
|---|---|---|---|---|
| Pregabalin 100 mg/kg, p.o. | 5.23 ± 0.09 ** | 5.37 ± 0.02 ## | 5.11 ± 0.10 ### | 5.36 ± 0.02 |
| Morphine 5 mg/kg, i.v. | 4.45 ± 0.11 + (9) | 5.28 ± 0.04 (9) | 4.07 ± 0.07 (9) | 5.26 ± 0.04 (9) |

Data are expressed as Mean ± SEM.
n = 10 animals per group, unless stated in parenthesis.
Statistical analysis only performed on log data.
†Vehicle = 1% carboxymethylcellulose.
+ $P < 0.05$,
++ $P < 0.01$ and
+++ $P < 0.001$ when compared to pre-dose data (paired 2-tailed Student's t-test).
$P < 0.05$,
$P < 0.01$ and
$P < 0.001$ when compared to vehicle group data (Kruskal-Wallis and Dunn's test).
** $P < 0.01$ when compared to vehicle group data (ANOVA and Dunnett's test).
$$ $P < 0.01$ when compared to pre-dose data (paired 2-tailed Student's t-test).

TABLE 22

Effects of oral Pregabalin and intravenous morphine on the left (L) and right (R) paw withdrawal latency to a thermal plantar stimulus in neuropathic rats (Phase 3)

| | Withdrawal Latency (s) at Time (min) Post-Dose | | | | | |
|---|---|---|---|---|---|---|
| | | | Phase 3 | | | |
| | Pre-Dose | | 70 | | 130 | |
| Treatment | L | R | L | R | L | R |
| Vehicle† 10 mL/kg, p.o. | 6.5 ± 0.5 | 12.4 ± 0.8 | 9.2 ± 1.0 | 12.2 ± 0.5 | 9.0 ± 1.0 | 10.7 ± 0.7 |
| Pregabalin 30 mg/kg, p.o. | 6.5 ± 0.5 | 13.1 ± 0.6 | 9.9 ± 0.8 | 13.4 ± 1.0 | 9.3 ± 0.8 | 13.7 ± 0.9 |
| Pregabalin 50 mg/kg, p.o. | 6.5 ± 0.6 | 11.4 ± 0.8 | 10.6 ± 0.6 | 12.9 ± 0.9 | 9.7 ± 1.1 | 13.6 ± 1.1 |
| Pregabalin 100 mg/kg, p.o. | 6.6 ± 0.7 | 11.6 ± 0.5 | 11.5 ± 0.8 | 12.6 ± 0.9 | 9.9 ± 0.9 | 13.4 ± 1.3 |
| Morphine 5 mg/kg, i.v. | 6.0 ± 0.5 (9) | 11.8 ± 0.6 (9) | 11.8 ± 1.2 ++ (9) | 14.0 ± 1.2 (9) | 7.3 ± 0.9 (9) | 13.1 ± 1.0 (9) |

| | Withdrawal Latency (s) at Time (min) Post-Dose Phase 3 | | | |
|---|---|---|---|---|
| | 190 | | 250 | |
| Treatment | L | R | L | R |
| Vehicle† 10 mL/kg, p.o. | 9.3 ± 1.2 | 12.2 ± 1.0 | 9.5 ± 0.8 $$ | 11.4 ± 0.6 |
| Pregabalin 30 mg/kg, p.o. | 8.3 ± 1.1 | 12.2 ± 0.4 | 10.9 ± 0.8 | 14.0 ± 0.8 |
| Pregabalin 50 mg/kg, p.o. | 11.2 ± 1.1 | 12.7 ± 0.5 | 9.0 ± 0.7 | 11.9 ± 0.7 |
| Pregabalin 100 mg/kg, p.o. | 7.6 ± 0.5 | 13.7 ± 0.7 | 9.7 ± 0.8 | 13.7 ± 1.1 |
| Morphine 5 mg/kg, i.v. | 8.0 ± 0.8 + (9) | 14.3 ± 1.0 (9) | 10.6 ± 1.4 + (9) | 14.1 ± 0.9 (9) |

Data are expressed as Mean ± SEM.
n = 10 animals per group, unless stated in parenthesis
†Vehicle = 1% carboxymethylcellulose.
+ $P < 0.05$ and
++ $P < 0.01$ when compared to pre-dose data (paired 2-tailed Student's t-test).
$$ $P < 0.01$ when compared to pre-dose data (paired 2-tailed Student's t-test

The invention claimed is:

1. A pharmaceutical composition comprising a compound of formula (VI), or a salt thereof,

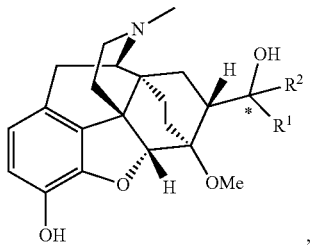

(VI)

wherein $R^1$ is n-propyl and $R^2$ is methyl, and * represents a (S) stereocentre, in a dosage form suitable for transdermal administration to a human subject,
wherein said dosage form is selected from mouth pastilles, sprays, aerosols, creams, lotions, ointments, gels, solutions, emulsions, suspensions, mouthwashes, oral gels reservoir type patches or matrix type patches.

2. The pharmaceutical composition as claimed in claim 1, wherein said dosage form suitable for transdermal administration is a reservoir type patch.

3. The pharmaceutical composition as claimed in claim 1, wherein said dosage form suitable for transdermal administration is a matrix type patch.

4. The pharmaceutical composition as claimed in claim 1, wherein said dosage form suitable for transdermal administration further comprises at least one pharmaceutically acceptable excipient.

5. The pharmaceutical composition as claimed in claim 1, wherein said dosage form suitable for transdermal administration further comprises water, acetone, ethanol, ethylene glycol, propylene glycol, butane-1,3-diol, isopropyl myristate, isopropyl palmitate, mineral oil, or mixtures thereof.

6. The pharmaceutical composition as claimed in claim 1, wherein said dosage form suitable for transdermal administration further comprises a moisturizer or humectant.

7. The pharmaceutical composition as claimed in claim 1, wherein said dosage form suitable for transdermal administration further comprises a penetration enhancer.

8. The pharmaceutical composition as claimed in claim 7, wherein said penetration enhancer is selected from the group consisting of acetone, alcohol, alkyl sulfoxide, dimethyl acetamide, dimethyl formamide, polyethylene glycol, pyrrolidone, urea, and a water-soluble or insoluble sugar ester.

9. A pharmaceutical composition comprising a compound of formula (VI), or a salt thereof,

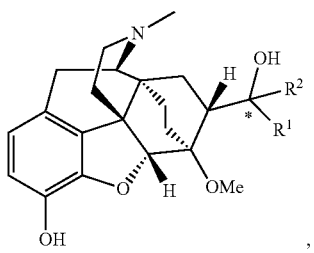

(VI)

wherein $R^1$ is n-propyl and $R^2$ is methyl, and * represents a (S) stereocentre, in a dosage form suitable for parenteral administration to a human subject.

10. The pharmaceutical composition as claimed in claim 9, wherein said dosage form is suitable for intravenous administration and is a solution, emulsion or suspension.

11. The pharmaceutical composition as claimed in claim 10, wherein said dosage form suitable for intravenous administration comprises sterile isotonic aqueous buffer.

12. The pharmaceutical composition as claimed in claim 10, wherein said dosage form suitable for intravenous administration comprises a solubilizing agent.

13. A compound of formula (VI),

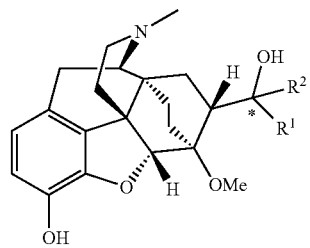

(VI)

wherein $R^1$ is n-propyl and $R^2$ is methyl, and the * represents a (S) stereocentre, wherein the compound is in the form of a salt derived from hydrochloric acid, hydrobromic acid, hydroiodic acid, sulfuric acid, sulfamic acid, phosphoric acid, nitric acid, p-toluenesulfonic acid, salicylic acid, methanesulfonic acid, oxalic acid, succinic acid, citric acid, malic acid, lactic acid, fumaric acid, and trifluoro acetic acid.

14. A pharmaceutical composition comprising a compound as claimed in claim 13.

15. A method of treating a human subject in need of pain relief, comprising administering to said subject a therapeutically effective amount of a compound as claimed in claim 13.

16. A method of treating a human subject in need of nociceptive or neuropathic pain relief, comprising administering to said subject a therapeutically effective amount of a compound as claimed in claim 13.

17. A method of treating a human subject in need of nociceptive or neuropathic pain relief, comprising administering to said subject a therapeutically effective amount of a compound of formula (VI), or a salt thereof,

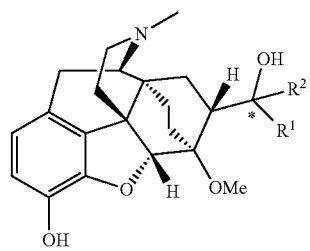

(VI)

wherein $R^1$ is n-propyl and $R^2$ is methyl, and the * represents a (S) stereocentre.

18. The pharmaceutical composition as claimed in claim 8, wherein said alcohol is ethanol, oleyl, or tetrahydrofuryl; said alkyl sulfoxide is dimethyl sulfoxide; and said pyrrolidone is polyvinylpyrrolidone; and said water-soluble or insoluble sugar ester is polysorbate 80 or sorbitan monostearate.

19. The pharmaceutical composition as claimed in claim 9, wherein said dosage form is supplied as a dry lyophilized powder or water free concentrate in a hermetically sealed container, where the powder or concentrate is to be mixed with sterile water or buffer prior to said parenteral administration.

\* \* \* \* \*

UNITED STATES PATENT AND TRADEMARK OFFICE
CERTIFICATE OF CORRECTION

Page 1 of 1

PATENT NO. : 10,745,406 B2
APPLICATION NO. : 15/336970
DATED : August 18, 2020
INVENTOR(S) : Whitelock et al.

It is certified that error appears in the above-identified patent and that said Letters Patent is hereby corrected as shown below:

On the Title Page

Item (60), Lines 3-4 below the subtitle "Related U.S. Application Data," the phrase "application No. 14/473,751, filed Aug. 18, 2014" should read --application No. 14/473,751, filed Aug. 29, 2014--.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*